(12) United States Patent
Bassaganya-Riera et al.

(10) Patent No.: US 11,117,881 B2
(45) Date of Patent: Sep. 14, 2021

(54) LANTHIONINE C-LIKE PROTEIN 2 LIGANDS, CELLS PREPARED THEREWITH, AND THERAPIES USING SAME

(71) Applicant: Landos Biopharma, Inc., Blacksburg, VA (US)

(72) Inventors: Josep Bassaganya-Riera, Blacksburg, VA (US); Andrew Leber, Blacksburg, VA (US); Raquel Hontecillas, Blacksburg, VA (US)

(73) Assignee: LANDOS BIOPHARMA, INC., Blacksburg, VA (US)

( * ) Notice: Subject to any disclaimer, the term of this patent is extended or adjusted under 35 U.S.C. 154(b) by 0 days.

(21) Appl. No.: 17/127,119

(22) Filed: Dec. 18, 2020

(65) Prior Publication Data

US 2021/0188800 A1   Jun. 24, 2021

Related U.S. Application Data

(60) Provisional application No. 63/031,938, filed on May 29, 2020, provisional application No. 62/951,906, filed on Dec. 20, 2019.

(51) Int. Cl.
| | | |
|---|---|---|
| *C07D 401/04* | (2006.01) | |
| *C07D 413/04* | (2006.01) | |
| *C07D 413/14* | (2006.01) | |
| *C07D 401/14* | (2006.01) | |
| *C07D 403/04* | (2006.01) | |

(52) U.S. Cl.
CPC ......... *C07D 401/04* (2013.01); *C07D 401/14* (2013.01); *C07D 403/04* (2013.01); *C07D 413/04* (2013.01); *C07D 413/14* (2013.01)

(58) Field of Classification Search
CPC .. C07D 401/04; C07D 401/14; C07D 413/04; C07D 413/14; C07D 403/04
USPC ....................................................... 514/385
See application file for complete search history.

(56) References Cited

U.S. PATENT DOCUMENTS

| | | |
|---|---|---|
| 4,983,584 A | 1/1991 | Fukaya et al. |
| 5,633,388 A | 5/1997 | Diana et al. |
| 5,856,326 A | 1/1999 | Anthony et al. |
| 7,427,631 B2 | 9/2008 | Eriksson et al. |
| 7,741,367 B2 | 6/2010 | Bassaganya-Riera et al. |
| 7,754,724 B2 | 7/2010 | Lorsbach et al. |
| 7,842,692 B2 | 11/2010 | Kugimiya et al. |
| 7,956,082 B2 | 6/2011 | Kugimiya et al. |
| 8,143,285 B2 | 3/2012 | Kugimiya et al. |
| 8,354,401 B2 | 1/2013 | Ishibuchi et al. |
| 8,993,763 B2 | 3/2015 | Kugimiya et al. |
| 9,556,146 B2 | 1/2017 | Bassaganya-Riera |
| 9,839,635 B2 | 12/2017 | Bassaganya-Riera |
| 10,028,950 B2 | 7/2018 | Bassaganya-Riera |
| 10,201,537 B2 | 2/2019 | May |
| 10,201,538 B2 | 2/2019 | Bassaganya-Riera et al. |
| 10,493,072 B2 | 12/2019 | Bassaganya-Riera |
| 10,682,349 B2 | 6/2020 | Bassaganya-Riera et al. |
| 2006/0046977 A1 | 3/2006 | Nunes et al. |
| 2006/0093580 A1 | 5/2006 | Iwashima et al. |
| 2007/0004750 A1 | 1/2007 | Lorsbach et al. |
| 2007/0203236 A1 | 8/2007 | Smith et al. |
| 2010/0160166 A1 | 6/2010 | Abrams et al. |
| 2010/0160355 A1 | 6/2010 | Degoey et al. |
| 2010/0216883 A1 | 8/2010 | Bassaganya-Riera et al. |
| 2011/0275558 A1 | 11/2011 | Bassaganya-Riera |
| 2012/0286254 A1 | 11/2012 | Stoessel et al. |
| 2013/0142825 A1 | 6/2013 | Bassaganya-Riera et al. |
| 2015/0087673 A1 | 3/2015 | Hitoshi et al. |
| 2015/0093694 A1 | 4/2015 | Watariguchi et al. |
| 2017/0119762 A1 | 5/2017 | Bassaganya-Riera |
| 2019/0160100 A1 | 5/2019 | Bassaganya-Riera et al. |

FOREIGN PATENT DOCUMENTS

| | | |
|---|---|---|
| CN | 100434419 C | 11/2008 |
| CN | 103709115 A | 4/2014 |
| JP | 2008/056615 | 3/2008 |
| JP | 2008056615 A | 3/2008 |
| JP | 2011246461 A | 12/2011 |
| KR | 2012035285 A | 4/2012 |
| MY | 146643 A | 10/2012 |
| WO | 9630343 A1 | 10/1996 |
| WO | 1997/036866 A1 | 10/1997 |
| WO | WO 1997/036866 A1 | 10/1997 |
| WO | 1999/033822 A1 | 7/1999 |
| WO | 99/38514 A1 | 8/1999 |
| WO | 2001/000587 A1 | 1/2001 |

(Continued)

OTHER PUBLICATIONS

Aurora Fine Chemicals. 3-(1-hydroxy-4-oxycyclohexyl)benzoic acid. http://online.aurorafinechemicals.com/StrSearch.asp. Downloaded Mar. 19, 2014.
Barba, G., et al., Recurrent pancreatitis revealing Crohn's disease. *Arch Pediatr*, 2002. 9(10): p. 1053-5.
Bassaganya-Riera et al., Peroxisome Proliferator-Activated Receptors: the Nutritionally Controlled Molecular Networks that Integrate Inflammation, Immunity and Metabolism. *Current Nutrition & Food Science*. 2005. 1: p. 179-187.
Al-Jarallah A, Oriowo MA, Khan I. Mechanism of reduced colonic contractility in experimental colitis: role of sarcoplasmic reticulum pump isoform-2. *Mol Cell Biochem* 2007;298:169-78.
Bassaganya-Riera J, Carbo A, Gandour RD, et al. An N,N-Bis(benzimidazolylpicolinoyl)piperazine (BT-11): A Novel Lanthionine Synthetase C-Like 2-Based Therapeutic for Inflammatory Bowel Disease, *J Med Chem*. Nov. 23, 2016;59(22):10113-10126.

(Continued)

*Primary Examiner* — Kahsay Habte
(74) *Attorney, Agent, or Firm* — Daniel A. Blasiole; DeWitt LLP

(57) ABSTRACT

Provided are compounds that target the lanthionine synthetase C-like protein 2 pathway. The compounds can be used to treat a number of conditions, including autoimmune diseases, inflammatory diseases, chronic inflammatory diseases, diabetes, and infectious diseases, such as lupus, Sjögren's syndrome, rheumatoid arthritis, type 1 diabetes, inflammatory bowel disease, viral diseases, and nonalcoholic steatohepatitis. The compounds can also be used to generate cells, such as immune cells, for treating the conditions.

38 Claims, 21 Drawing Sheets

(56) References Cited

FOREIGN PATENT DOCUMENTS

| | | | |
|---|---|---|---|
| WO | 02/34745 A1 | 5/2002 | |
| WO | 2003/087098 A1 | 10/2003 | |
| WO | 2004/002992 A1 | 1/2004 | |
| WO | 2005/037269 A1 | 4/2005 | |
| WO | 2005/082905 A1 | 9/2005 | |
| WO | 2006/053109 A1 | 5/2006 | |
| WO | WO 2006/053109 A1 | 5/2006 | |
| WO | 2006/080821 A1 | 8/2006 | |
| WO | WO 2006/080821 A1 | 8/2006 | |
| WO | 2006/114264 A1 | 11/2006 | |
| WO | 2007/019417 A1 | 2/2007 | |
| WO | WO 2007/019417 A1 | 2/2007 | |
| WO | 2007/040438 A2 | 4/2007 | |
| WO | 2008/061373 A1 | 5/2008 | |
| WO | 2008/079277 A1 | 7/2008 | |
| WO | 2008/092006 A2 | 7/2008 | |
| WO | WO 2008/079277 A1 | 7/2008 | |
| WO | 2009/067600 A2 | 5/2009 | |
| WO | 2009/067621 A1 | 5/2009 | |
| WO | WO 2009/067600 A2 | 5/2009 | |
| WO | WO 2009/067621 A1 | 5/2009 | |
| WO | 2009/076618 A2 | 6/2009 | |
| WO | 2010/075376 A | 7/2010 | |
| WO | 2010/121046 A1 | 10/2010 | |
| WO | 2011/066898 A1 | 6/2011 | |
| WO | WO 2011/066898 A1 | 6/2011 | |
| WO | 2011/156554 A1 | 12/2011 | |
| WO | 2011/159854 A1 | 12/2011 | |
| WO | 2012/016217 A1 | 2/2012 | |
| WO | 2013/097773 A1 | 7/2013 | |
| WO | 2016/064445 A1 | 4/2016 | |
| WO | 2018/141854 A1 | 8/2018 | |
| WO | 2019/108418 A1 | 6/2019 | |

OTHER PUBLICATIONS

Bassaganya-Riera J, Reynolds K, Martino-Catt S, et al. Activation of PPAR gamma and delta by conjugated linoleic acid mediates protection from experimental inflammatory bowel disease. *Gastroenterology* 2004;127:777-91.

Bassaganya-Riera, J. et al, Abscisic acid regulates inflammation via ligand-binding domain-independent activation of peroxisome proliferator-activated receptor gamma. *J Biol Chem* 2011. 286(4):p. 2504-16.

Bassaganya-Riera, J., et al., Mechanisms of action and medicinal applications of abscisic Acid. *Curr Med Chem*, 2010. 17(5): p. 467-78.

Bissel P, Boes K, Hinckley J, et al. Exploratory Studies With BT-11: A Proposed Orally Active Therapeutic for Crohn's Disease. *Int J Toxicol* 2016;35:521-9.

Bouzidi A, Mesbah-Amroun H, Boukercha A, et al. Association between MDR1 gene polymorphisms and the risk of Crohn's disease in a cohort of Algerian pediatric patients. *Pediatr Res* 2016;80:837-843.

Braverman, I.M., Skin signs of gastrointestinal disease. *Gastroenterology*, 2003. 124(6): p. 1595-614.

Bruzzone, S., et al., Abscisic Acid Is an Endogenous Stimulator of Insulin Release from Human Pancreatic Islets with Cyclic ADP Ribose as Second Messenger. *J Biol Chem*, 2008. 283(47): p. 32188-32197.

Buffie, C.G. et al., Precision microbiome reconstitution restores bile acid mediated resistance to Clostridium difficile. Nature (2014) 517(7533): p. 205-208.

Butler D. Cheaper approaches to flu divide researchers. *Nature*. Aug. 30, 2007; 448(7157):976-7.

Butterworth, S.A., et al., Recent trends in diagnosis and treatment of Clostridium difficile in a tertiary care facility. *Am J Surg*, (1998) 175(5): p. 403-7.

Camilleri, M., GI clinical research 2002-2003: The year in review. *Clinical Gastroenterology and Hepatology*, 2003. 1: p. 415-420.

Canavan et al., Developing in vitro expanded CD45RA+ regulatory T cells as an adoptive cell therapy for Crohn's disease. *Gut.* Apr. 2016;65(4):584-94.

Cantarini L, Pucino V, Vitale A, et al. Immunometabolic biomarkers of inflammation in Behcet's disease: relationship with epidemiological profile, disease activity and therapeutic regimens. *Clin Exp Immunol* 2016;184:197-207.

CAS Registry No. 1173038-16-8, entered into the Registry File on Aug. 5, 2009, supplied by Ambinter Chemical Supplier.

CAS Registry No. 1389465-82-0, entered into the Registry File on Aug. 12, 2012, supplied by Ukrorgsyntez LTD. Chemical Supplier.

Casteele N, Ferrante M, Van Assche G, et al. Trough concentrations of infliximab guide dosing for patients with inflammatory bowel disease. *Gastroenterology* 2015;148:1320-9 e3.

CDC. National Diabetes Fact Sheet: general information and national estimates on diabetes in the United States, 2005. In U. S. Department of Health and Human Services, *Center for Disease Control and Prevention*, 2005. Atlanta, Georgia.

Chang CH, Curtis JD, Maggi LV, Jr., et al. Posttranscriptional control of T cell effector function by aerobic glycolysis. *Cell* 2013;153:1239-51.

Chemical Abstracts Service: Columbus, OH; RN 1541129-28-5, https://scifinder.cas.org (accessed Apr. 28, 2014).

Chemical Abstracts Service: Columbus, OH; RN 1557590-30-3, https://scifinder.cas.org (accessed Mar. 10, 2014).

Chemical Abstracts Service: Columbus, OH; RN 182807-30-3, https://scifinder.cas.org (accessed Apr. 28, 2014).

Chen, X. et al., A Mouse Model of Clostridium difficile—Associated Disease. *Gastroenterology* (2008) 135: 1984-1992.

Cheng SM, Li JC, Lin SS, et al. HIV-1 transactivator protein induction of suppressor of cytokine signaling-2 contributes to dysregulation of IFN {gamma} signaling. *Blood* 2009;113:5192-201.

Chiriac MT, Buchen B, Wandersee A, et al. Activation of Epithelial Signal Transducer and Activator of Transcription 1 by Interleukin 28 Controls Mucosal Healing in Mice With Colitis and Is Increased in Mucosa of Patients With Inflammatory Bowel Disease. *Gastroenterology* 2017;153:123-138 e8.

Chua P C et al., "Cyclohexenyl- and Dehydropiperidinyl-Alkynyl Pyridines as Potent Metabotropic Glutamate Subtype 5 (mGlu5) Receptor Antagonists," *Bioorganic & Medicinal Chemistry Letters*, Pergamon, Amsterdam, NL, vol. 15, No. 20, Oct. 15, 2005, pp. 4589-4593.

Cohen, R.D., et al., the cost of hospitalization in Crohn's disease. *Am J Gastroenterol*, 2000. 95(2): p. 524-30.

Colombel JF, Mahadevan U. Inflammatory Bowel Disease 2017: Innovations and Changing Paradigms. *Gastroenterology* 2017;152:309-312.

Danese S, Fiocchi C, Panes J. Drug development in IBD: from novel target identification to early clinical trials. *Gut* 2016;65:1233-9.

Dawood FS, et al. Estimated global mortality associated with the first 12 months of 2009 pandemic influenza A H1N1 virus circulation: a modelling study. *Lancet Infect Dis*. Sep. 2012; 12(9):687-95.

De Rosa V, Galgani M, Porcellini A, et al. Glycolysis controls the induction of human regulatory T cells by modulating the expression of FOXP3 exon 2 splicing variants. *Nat Immunol* 2015;16:1174-84.

Delgoffe GM, Woo SR, Turnis ME, et al. Stability and function of regulatory T cells is maintained by a neuropilin-1-semaphorin-4a axis. *Nature* 2013;501:252-6.

Do JS, Visperas A, Sanogo YO, et al. An IL-27/Lag3 axis enhances Foxp3+ regulatory T cell-suppressive function and therapeutic efficacy. *Mucosal Immunol* 2016;9:137-45.

Eastaff-Leung N, Mabarrack N, Barbour A, et al. Foxp3+ regulatory T cells, Th17 effector cells, and cytokine environment in inflammatory bowel disease. *J Clin Immunol* 2010;30:80-9.

Enserink M. Infectious disease. Old drugs losing effectiveness against flu; could statins fill gap? *Science*. Sep. 23, 2005; 309(5743):1976-7.

Fedson DS. Confronting an influenza pandemic with inexpensive generic agents: can it be done? *Lancet Infect Dis*. Sep. 2008; 8(9):571-6.

Fekety, R. et al., Diagnosis and treatment of Clostridium difficile colitis. *JAMA*, (1993) 269(1): p. 71-5.

(56) References Cited

OTHER PUBLICATIONS

Fullerton MD, Steinberg GR, Schertzer JD. Immunometabolism of AMPK in insulin resistance and atherosclerosis. *Mol Cell Endocrinol* 2013;366:224-34.
G.A. Patani et al., *Chem. Rev.*, 96, 1996, pp. 31-47-3176.
Guri et al., Abscisic acid ameliorates atherosclerosis by suppressing macrophage and CD4+ T cell recruitment into the aortic wall. *J Nutr Biochem*, 2010. 21(12): p. 1178-85.
Guri et al., Abscisic acid ameliorates experimental IBD by downregulating cellular adhesion molecule expression and suppressing immune cell infiltration. *Clin Nutr*, 2010. 29(6): p. 824-31.
Guri et al., Abscisic acid synergizes with rosiglitazone to improve glucose tolerance and down-modulate macrophage accumulation in adipose tissue: possible action of the cAMP/PKA/PPAR gamma axis. *Clin Nutr*, 2010. 29(5): p. 646-53.
Guri et al., Dietary abscisic acid ameliorates glucose tolerance and obesity-related inflammation in db/db mice fed high-fat diets. *Clin Nutr*, 2007. 26(1): p. 107-16.
Guri et al., Loss of PPAR gamma in immune cells impairs the ability of abscisic acid to improve insulin sensitivity by suppressing monocyte chemoattractant protein-1 expression and macrophage infiltration into white adipose tissue. *J Nutr Biochem*, 2008. 19(4): p. 216-28.
Guri, A.J., et al., T cell PPAR gamma is required for the anti-inflammatory efficacy of abscisic acid against experimental inflammatory bowel disease. *Journal of Nutritional Biochemistry*, 2011. 22(9): p. 812-9.
Guri, A.J., et al., The role of T cell PPAR gamma in mice with experimental inflammatory bowel disease. *BMC Gastroenterology*, 2010. 10:60: p. 1-13.
Haarberg KM, Wymore Brand MJ, Overstreet AM, et al. Orally administered extract from Prunella vulgaris attenuates spontaneous colitis in mdrla(-/-) mice. *World J Gastrointest Pharmacol Ther*. Nov. 6, 2015;6(4):223-37.
Hacer Karatas et al., "Synthesis and Potent In Vitro Activity of Novel 1H-Benzimidazoles as Anti-MRSA Agents," *Chemical Biology & Drug Design*, vol. 80, No. 2, Apr. 30, 2012, pp. 237-244.
Hanauer, S.B. et al., The state of the art in the management of inflammatory bowel disease. *Rev Gastroenterol Disord*, 2003. 3(2): p. 81-92.
Ho PC, Bihuniak JD, Macintyre AN, et al. Phosphoenolpyruvate Is a Metabolic Checkpoint of Anti-tumor T Cell Responses. *Cell* 2015;162:1217-28.
Holmen N, Lundgren A, Lundin S, et al. Functional CD4+CD25high regulatory T cells are enriched in the colonic mucosa of patients with active ulcerative colitis and increase with disease activity. *Inflamm Bowel Dis* 2006;12:447-56.
Hontecillas, R., et al., Dietary abscisic acid ameliorates influenza-virus-associated disease and pulmonary immunopathology through a PPARgamma-dependent mechanism. *J Nutr Biochem*, 2013. 24(6): p. 1019-27.
Hontecillas, R., et al., Dietary abscisic acid ameliorates influenza virus-associated disease and pulmonary immunopathology through a PPAR g-dependent mechanism. *Journal of Nutritional Biochemistry*, 2012. 24(6): p. 1019-27.
Johnson, S. et al., Clostridium difficile—associated diarrhea, *Clin Infect Dis*. May 1998; 26(5):1027-34.
Kaplan GG. The global burden of IBD: from 2015 to 2025. *Nat Rev Gastroenterol Hepatol* 2015;12:720-7.
Keane J, Gershon S, Wise RP, et al. Tuberculosis associated with infliximab, a tumor necrosis factor alpha-neutralizing agent. *N Engl J Med* 2001;345:1098-104.
Leber A, Hontecillas R, Tubau-Juni N, et al. NLRX1 Regulates Effector and Metabolic Functions of CD4+ T Cells. *J Immunol* 2017;198:2260-2268.
Leber A, Hontecillas R, Tubau-Juni N, et al. Translating nutritional immunology into drug development for inflammatory bowel disease. *Curr Opin Gastroenterol* 2016;32:443-449.
Leber A., et al., Systems Modeling of Interactions between Mucosal Immunity and the Gut Microbiome during Clostridium difficile Infection. *PLoS One* (2015) 10(7): p. e0134849.
Leber et al., Activation of LANCL2 by BT-11 ameliorates IBD by supporting regulatory T Cell stability through immunometabolic mechanisms, *Inflammatory Bowel Diseases*, vol. 24, No. 9, Sep. 2018, pp. 1978-1991.
Leber et al., Tu1739—Translation of immunometabolic mechanisms of Bt-11 to humans with Crohn's disease, *Gastroenterology*, vol. 154, No. 6, suppl. 1, TU1739, May 2018.
Leber, A. et al., Modeling new immunoregulatory therapeutics as antimicrobial alternatives for treating Clostridium difficile infection. *Artif Intell Med* (2017) 78: p. 1-13.
Li C, Jiang S, Liu SQ, et al. MeCP2 enforces Foxp3 expression to promote regulatory T cells' resilience to inflammation. *Proc Natl Acad Sci USA* 2014;111:E2807-16.
Li L, Boussiotis VA. The role of IL-17-producing Foxp3+ CD4+ T cells in inflammatory bowel disease and colon cancer. *Clin Immunol* 2013;148:246-53.
Li Z, Arijs I, De Hertogh G, et al. Reciprocal changes of Foxp3 expression in blood and intestinal mucosa in IBD patients responding to infliximab. *Inflamm Bowel Dis* 2010;16:1299-310.
Lichtenstein, G.R. et al., Recent advances in the treatment of Crohn's colitis, 2003, *The Center for Health Care Education, LLC*. No Copy Provided.
Lindsay, J.O. et al., Review article: the immunoregulatory cytokine interleukin-10—a therapy for Crohn's disease? *Aliment Pharmacol Ther*, 2001. 15(11): p. 1709-16.
Lu P, Hontecillas R, Horne WT, et al. Computational modeling-based discovery of novel classes of anti-inflammatory drugs that target lanthionine synthetase C-like protein 2. *PLoS One* 2012;7:e34643.
Lu, P., et al., Computational modeling-based discovery of novel classes of anti-inflammatory drugs that target lanthionine synthetase C-like protein 2. *PLoS One*, 2012. 7(4): p. e34643.
Lu, P., et al., Lanthionine synthetase component C-like protein 2: a new drug target for inflammatory diseases and diabetes. *Curr Drug Targets*, 2014. 15(6): p. 565-72.
Lu, P., et al., Molecular modeling of lanthionine synthetase component C-like protein 2: a potential target for the discovery of novel type 2 diabetes prophylactics and therapeutics. *J Mol Model*, 2011. 17(3): p. 543-53.
Lung J, Liu KJ, Chang JY, et al. MBP-1 is efficiently encoded by an alternative transcript of the ENO1 gene but post-translationally regulated by proteasome-dependent protein turnover. *FEBS J* 2010;277:4308-21.
Luo Y et al., "Synthesis and In Vitro Cytotoxic Evaluation of Some Thiazolylbenzimidazole Derivatives," *European Journal of Medicinal Chemistry*, Editions Scientifique Elsevier, Paris, FR, vol. 46, No. 1, Jan. 1, 2011, pp. 417-422.
Ma, R.C. et al., Diabetes: incidence of childhood type 1 diabetes: a worrying trend. *Nat Rev Endocrinol*, 2009. 5(10): p. 529-30.
Majowicz et al., Murine CD4+CD25- cells activated in vitro with PMA/ionomycin and anti-CD3 acquire regulatory function and ameliorate experimental colitis in vivo. *BMC Gastroenterol*. Dec. 3, 2012;12:172.
Marri, S.R. et al., The education and employment status of patients with inflammatory bowel diseases. *Inflamm Bowel Dis*, 2005. 11(2): p. 171-7.
Mathis D, Shoelson SE. Immunometabolism: an emerging frontier. *Nat Rev Immunol* 2011;11:81.
Maul J, Loddenkemper C, Mundt P, et al. Peripheral and intestinal regulatory CD4+ CD25(high) T cells in inflammatory bowel disease. *Gastroenterology* 2005;128:1868-78.
Mayer et al., Molecular cloning, characterization, and tissue-specific expression of human LANCL2, a novel member of the LanC-like protein family. *DNA Seq*, 2001. 12(3): p. 161-6.
Mayer, H., et al., Isolation, molecular characterization, and tissue-specific expression of a novel putative G protein-coupled receptor. *Biochim Biophys Acta*, 1998. 1395(3): p. 301-8.
Melo F et al., Assessing protein structures with a non-local atomic interaction energy. *J Mol Biol*. Apr. 17, 1998; 277(5):1141-52.
Mendez-Lucas A, Hyrossova P, Novellasdemunt L, et al. Mitochondrial phosphoenolpyruvate carboxykinase (PEPCK-M) is a pro-survival,

(56) References Cited

OTHER PUBLICATIONS endoplasmic reticulum (ER) stress response gene involved in tumor cell adaptation to nutrient availability. *J Biol Chem* 2014;289:22090-102.
Mirlekar B, Ghorai S, Khetmalas M, et al. Nuclear matrix protein SMAR1 control regulatory T-cell fate during inflammatory bowel disease (IBD). *Mucosal Immunol* 2015;8:1184-200.
Morris, G.M., et al., AutoDock4 and AutoDockTools4: Automated docking with selective receptor flexibility. *J Comput Chem*, 2009. 30(16): p. 2785-91.
Mullard, A., Cancer metabolism pipeline breaks new ground. *Nat Rev Drug Discov.* (2016) 15(11): p. 735-737.
Musher, D.M. et al., Relatively poor outcome after treatment of Clostridium difficile colitis with metronidazole. *Clin Infect Dis* (2005) 40(11): p. 1586-90.
Nakagawa H, Sido JM, Reyes EE, et al. Instability of Helios-deficient Tregs is associated with conversion to a T-effector phenotype and enhanced antitumor immunity. *Proc Natl Acad Sci USA* 2016;113:6248-53.
Nesto, R.W., et al., Thiazolidinedione use, fluid retention, and congestive heart failure: a consensus statement from the American Heart Association and American Diabetes Association. Oct. 7, 2003. *Circulation*, 2003. 108(23): p. 2941-8.
Newton R, Priyadharshini B, Turka LA. Immunometabolism of regulatory T cells. *Nat Immunol* 2016;17:618-25.
Ohkura N, Hamaguchi M, Morikawa H, et al. T cell receptor stimulation-induced epigenetic changes and Foxp3 expression are independent and complementary events required for Treg cell development. *Immunity* 2012;37:785-99.
O'Neill, L.A. et al., A guide to immunometabolism for immunologists. *Nat Rev Immunol.* (2016) 16(9): p. 553-65.
Pepin, J. Increasing risk of relapse after treatment of Clostridium difficile colitis in Quebec, Canada. *Clin Infect Dis* (2005) 40(11): p. 1591-7.
Posselt G, Schwarz H, Duschl A, et al. Suppressor of cytokine signaling 2 is a feedback inhibitor of TLR-induced activation in human monocyte-derived dendritic cells. *J Immunol* 2011;187:2875-84.
Quigley, E., Influenza therapies: vaccines and antiviral drugs. *Drug Discov Today*, 2006. 11(11-12): p. 478-80.
Rabilloud et al., *Chemical Abstracts* vol. 64 : 104885 (1966).
Rothberg, M.B. et al., Complications of viral influenza. *Am J Med.* 2008. 121(4): p. 258-64.
Schwab M, Schaeffeler E, Marx C, et al. Association between the C3435T MDR1 gene polymorphism and susceptibility for ulcerative colitis. *Gastroenterology* 2003;124:26-33.
Shevach EM, Davidson TS, Huter EN, et al. Role of TGF-Beta in the induction of Foxp3 expression and T regulatory cell function. *J Clin Immunol* 2008;28:640-6.
Smiles Translator and Converter. http://cactus.nci.nih.gov/translate.
Souza Co, Teixeira AA, Lima EA, et al. Palmitoleic acid (n-7) attenuates the immunometabolic disturbances caused by a high-fat diet independently of PPARalpha. *Mediators Inflamm* 2014;2014:582197.
Sparre, T., et al., Unraveling the pathogenesis of type 1 diabetes with proteomics: present and future directions. *Mol Cell Proteomics*, 2005. 4(4): p. 441-57.
Spunt, S., et al., Cancer Epidemiology in Older Adolescents and Young Adults 15 to 29 Years of Age, in SEER AYA Monograph. 2008, *National Cancer Institute*: Bethesda, MD. p. 123-133.
Stenson, W.F., Interleukin-4 hyporesponsiveness in inflammatory bowel disease: immune defect or physiological response? *Gastroenterology*, 1995. 108(1): p. 284-6.
STN Registry entry 1580196-32-2/CRN. Methanone, [5-(2benzothiazolyl)-2-thienyl](2,5-dimethyl-1-piperazinyl)-, hydrochloride.
STN Registry entry 1581903-50-5/CRN. Methanone, [5-(2benzothiazolyl)-2-furanyl](2,5-dimethyl-1-piperazinyl)-,hydrochloride.
STN Registry entry 1582503-48-7/CRN. Methanone, [5-(2enzothiazolyl)-2-furanyl]-1-piperazinyl-, hydrochloride.
STN Registry entry 1583915-44-9/CRN. Methanone, [5-(2benzothiazolyl)-2-furanyl](2-methyl-1-piperazinyl)-, hydrochloride.
STN Registry entry 1586233-94-4/CRN. Methanone, [5-(2benzothiazolyl)-2-thienyl](2-methyl-1-piperazinyl)-, hydrochloride.
STN Registry entry 1606349-60-3/CRN. Methanone, [5-(2benzothiazolyl)-2-furanyl](3-methyl-1-piperazinyl)-, hydrochloride.
Strober W, Fuss IJ Proinflammatory cytokines in the pathogenesis of inflammatory bowel diseases. *Gastroenterology* 2011;140:1756-1767.
Sturla, L., et al., Binding of abscisic acid to human LANCL2. *Biochem Biophys Res Commun*, 2011. 415(2): p. 390-5.
Sturla, L., et al., LANCL2 is necessary for abscisic acid binding and signaling in human granulocytes and in rat insulinoma cells. *J Biol Chem*, 2009. 284(41): p. 28045-57.
Suarez-Pinzon et al., Combination therapy with glucagon-like peptide-1 and gastrin induces beta-cell neogenesis from pancreatic duct cells in human islets transplanted in immunodeficient diabetic mice. *Cell Transplant*, 2008. 17(6): p. 631-40.
Takatori H, Kawashima H, Matsuki A, et al. Helios Enhances Treg Cell Function in Cooperation with FoxP3. *Arthritis Rheumatol* 2015;67:1491-502.
Tillack C, Ehmann LM, Friedrich M, et al. Anti-TNF antibody-induced psoriasiform skin lesions in patients with inflammatory bowel disease are characterised by interferon-gamma-expressing Th1 cells and IL-17A/IL-22-expressing Th17 cells and respond to anti-IL-12/IL-23 antibody treatment. *Gut* 2014;63:567-77.
Trott et al., Software News and Update AutoDock Vina: Improving the Speed and Accuracy of Docking with a New Scoring Function, Efficient Optimization, and Multithreading. *Journal of Computational Chemistry*, 2010. 31(2): 455-461.
Uhlig HH, Coombes J, Mottet C, et al. Characterization of Foxp3+ CD4+CD25+ and IL-10-secreting CD4+CD25+ T cells during cure of colitis. *J Immunol* 2006;177:5852-60.
Vehik, K., et al., Increasing incidence of type 1 diabetes in 0- to 17-year-old Colorado youth. *Diabetes Care*, 2007. 30(3): p. 503-9.
Viladomiu, M. et al., Modeling the role of peroxisome proliferator-activated receptor gamma and microRNA-146 in mucosal immune responses to Clostridium difficile. *PLoS One* (2012) 7: e47525.
Vincent EE, Sergushichev A, Griss T, et al. Mitochondrial Phosphoenolpyruvate Carboxykinase Regulates Metabolic Adaptation and Enables Glucose-Independent Tumor Growth. *Mol Cell* 2015;60:195-207.
Wang Z, Zheng Y, Hou C, et al. DNA methylation impairs TLR9 induced Foxp3 expression by attenuating IRF-7 binding activity in fulminant type 1 diabetes. *J Autoimmun* 2013;41:50-9.
Wolf AJ, Reyes CN, Liang W, et al. Hexokinase Is an Innate Immune Receptor for the Detection of Bacterial Peptidoglycan. *Cell* 2016;166:624-36.
Wysowski, D.K. et al., Rapid increase in the use of oral antidiabetic drugs in the United States, 1990-2001. *Diabetes Care*, 2003. 26(6): p. 1852-5.
Yajnik V, Khan N, Dubinsky M, et al. Efficacy and Safety of Vedolizumab in Ulcerative Colitis and Crohn's Disease Patients Stratified by Age. *Adv Ther* 2017;34:542-559.
Yang QF, Chen BL, Zhang QS, et al. Contribution of MDR1 gene polymorphisms on IBD predisposition and response to glucocorticoids in IBD in a Chinese population. *J Dig Dis* 2015;16:22-30.
Zefirova O.N. et al., Vestnik Moscovskogo Universiteta, Issue 2, *Chemistry*, vol. 43, 4, 2002, p. 251-256. (Translation provided.).
Zenewicz LA, Antov A, Flavell RA. CD4 T-cell differentiation and inflammatory bowel disease. *Trends Mol Med* 2009;15:199-207.
Zocchi E, Hontecillas R, Leber A, et al. Abscisic Acid: A Novel Nutraceutical for Glycemic Control. *Front Nutr* 2017;4:24.
Bissel P, et al. Exploratory Studies With BT-11: A Proposed Orally Active Therapeutic for Crohn's Disease. *Int J Toxicol*. Sep. 2016;35(5):521-9.

(56) References Cited

OTHER PUBLICATIONS

Canavan JB, et al., Developing in vitro expanded CD45RA+ regulatory T cells as an adoptive cell therapy for Crohn's disease. *Gut*. Apr. 2016;65(4):584-94.

Carbo A, et al., An N,N-Bis(benzimidazolylpicolinoyl)piperazine (BT-11): A Novel Lanthionine Synthetase C-Like 2-Based Therapeutic for Inflammatory Bowel Disease. *J Med Chem*. Nov. 23, 2016;59(22):10113-10126.

Leber A. et al., Activation of LANCL2 by BT-11 Ameliorates IBD by Supporting Regulatory T Cell Stability Through Immunometabolic Mechanisms. *Inflamm Bowel Dis*. Aug. 16, 2018;24(9):1978-1991.

Leber A, et al., Nonclinical Toxicology and Toxicokinetic Profile of an Oral Lanthionine Synthetase C-Like 2 (LANCL2) Agonist, BT-11. *Int J Toxicol*. Mar./Apr. 2019;38(2):96-109.

Leber A, et al., Oral Treatment with BT-11 Ameliorates Inflammatory Bowel Disease by Enhancing Regulatory T Cell Responses in the Gut. *J Immnunol*. Apr. 1, 2019;202(7):2095-2104.

Leber A, et al., The Safety, Tolerability, and Pharmacokinetics Profile of BT-11, an Oral, Gut-Restricted Lanthionine Synthetase C-Like 2 Agonist Investigational New Drug for Inflammatory Bowel Disease: A Randomized, Double-Blind, Placebo-Controlled Phase I Clinical Trial. *Inflamm Bowel Dis*. Mar. 4, 2020;26(4):643-652.

Majowicz A, et al., Murine CD4+CD25- cells activated in vitro with PMA/ionomycin and antiCD3 acquire regulatory function and ameliorate experimental colitis in vivo. *BMC Gastroenterol*. Dec. 3, 2012;12:172.

Written Opinion of the International Searching Authority for PCT/US2020/066063, dated Mar. 31, 2021.

| ID | Structure | Affinity (kcal/mol) |
|---|---|---|
| BT-63 | 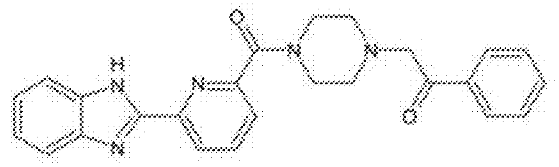 | -7.8 |
| BT-64 | 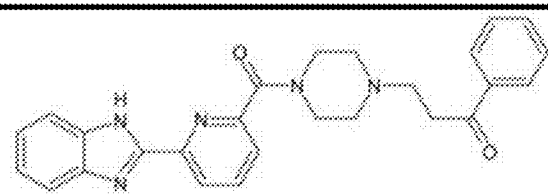 | -7.7 |
| BT-65 | 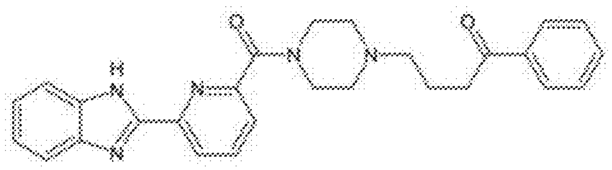 | -7.5 |

FIG. 1A

| ID | Structure | Affinity (kcal/mol) |
|---|---|---|
| BT-71 | 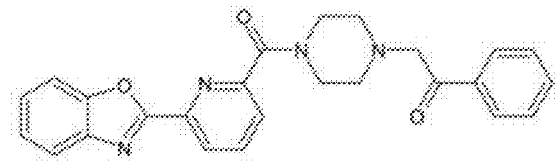 | -7.9 |
| BT-72 | 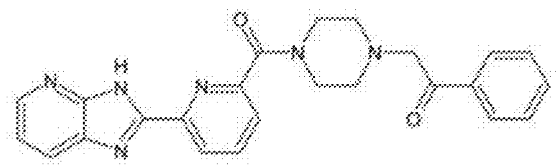 | -7.7 |
| BT-73 | 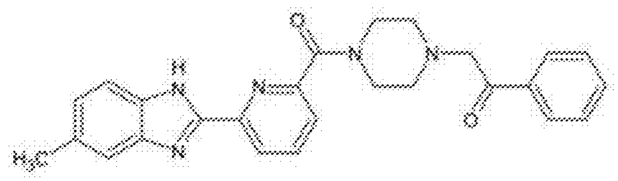 | -7.9 |
| BT-74 | 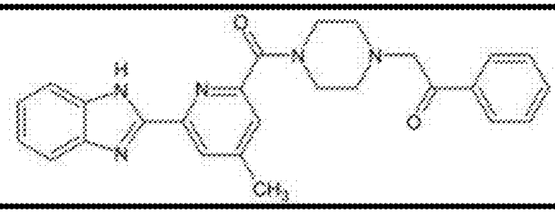 | -8.0 |
| BT-75 | 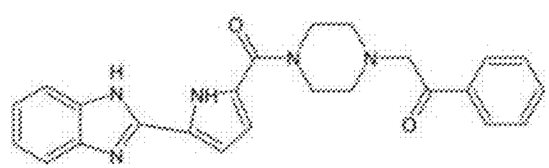 | -7.5 |

FIG. 1B

| ID | Structure | Affinity (kcal/mol) |
|---|---|---|
| BT-95 | 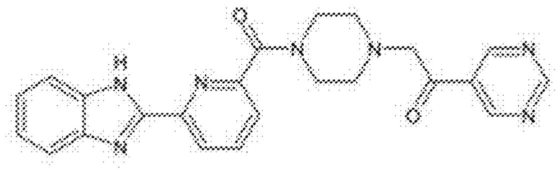 | -8.1 |
| BT-96 | 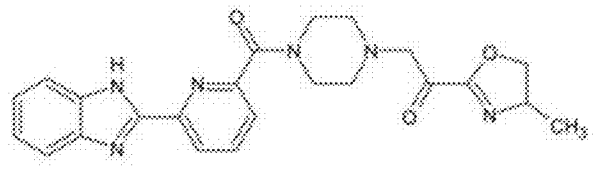 | -7.7 |
| BT-99 | 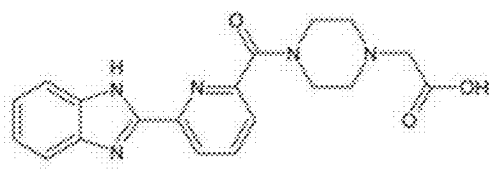 | -7.2 |

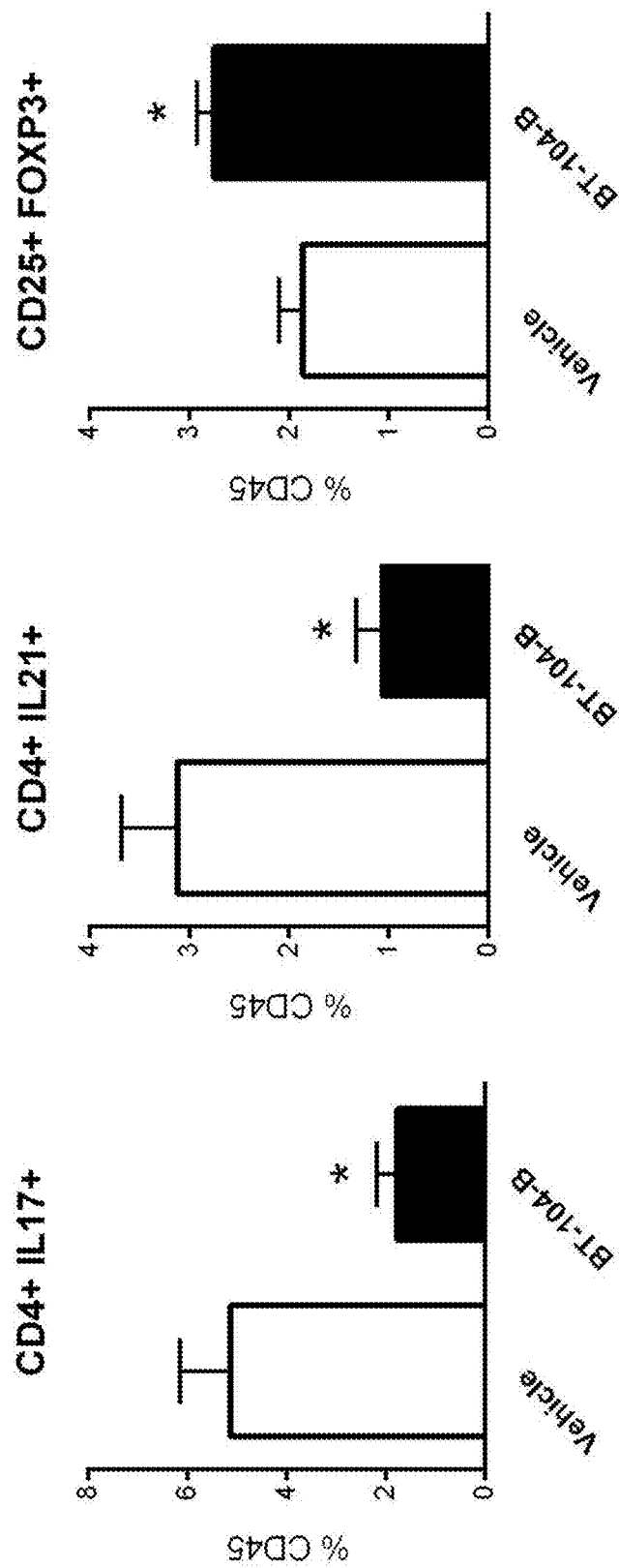

LANTHIONINE C-LIKE PROTEIN 2 LIGANDS, CELLS PREPARED THEREWITH, AND THERAPIES USING SAME

FIELD OF THE INVENTION

The present invention relates to the field of medical treatments for diseases and disorders. More specifically, the present invention relates to classes of biologically active compounds that treat and prevent inflammatory and immune mediated diseases such as inflammatory bowel disease, type 1 diabetes, lupus, Sjögren's syndrome, rheumatoid arthritis, psoriasis, and multiple sclerosis, as well as chronic inflammatory diseases and disorders such as insulin resistance, impaired glucose tolerance, prediabetes, type 2 diabetes, and obesity-related inflammation, among others.

BACKGROUND

Lanthionine C-like protein 2 (LANCL2) (also called "lanthionine synthetase C-like protein 2" or "lanthionine synthetase component C-like protein 2") is a membrane receptor expressed in immune and epithelial cells of various mucosa, including respiratory and GI, as well as reproductive and neural tissues that can be controlled by direct binding of ligands. Activation of the LANCL2 pathway has proven beneficial in multiple autoimmune, inflammatory and metabolic disorders ranging from glycemic control and insulin sensitivity in diabetes to promotion of survival and regulatory effects in viral and bacterial infectious disease to suppression of inflammation in inflammatory bowel disease.

Autoimmune disorders such as inflammatory bowel disease (IBD), systemic lupus erythematosus, rheumatoid arthritis, type 1 diabetes, psoriasis, and multiple sclerosis, are rising in incidence throughout the world. Meanwhile, other chronic diseases of metabolic origin, including prediabetes, type 2 diabetes and metabolic syndrome, are estimated to afflict nearly half of the adult population in the United States. Across these disorders, current treatments have mild efficacy with the potential for severe side effects such as heart attack and stroke (TZDs for type 2 diabetes) or increased rates of cancer and infection (biologics for inflammatory bowel diseases and other autoimmune diseases) and without much increase in overall quality of life. Type 1 diabetes has no approved medications other than life-long insulin therapy. Other diseases such as multiple sclerosis and systemic lupus erythematosus have very limited options to slow the progression of disease towards debilitating physical conditions that require organ transplants and complete living care. The LANCL2 pathway offers an innovative solution to these diseases normalizing metabolism, restoring immunological tolerance, and suppressing the inflammation contributing to a worsened prognosis in many of these diseases.

Abscisic acid ("ABA") is one of the natural compounds found that binds to LANCL2. There is an enormous number of compounds described in the field of synthetic organic chemistry. Various compounds are provided by the following references: WO1997/036866 to Diana et al., WO 2006/053109 to Sun et al., WO 2006/080821 to Kim et al., WO 2007/019417 to Nunes et al., WO 2009/067600 and WO 2009/067621 to Singh et al., WO 2008/079277 to Adams et al., JP 2008/056615 to Urasoe et al., WO 2011/066898 to Stoessel et al., US 2013/0142825 to Bassaganya-Riera et al., and U.S. Pat. No. 7,741,367 to Bassaganya-Riera et al. Some of the compounds described in these references are known to activate the LANCL2 pathway and others are not.

Previous LANCL2 targeting compounds, such as BT-11, are highly restricted to the gastrointestinal tract with limited systemic exposure. While this localization can be advantageous for the treatment of gastrointestinal disorders and infections, further classes of LANCL2 based therapeutics are needed for the treatment of systemic diseases and non-GI disorders with varying pharmacokinetic properties and potency. BT-11 and its therapeutic uses are described in U.S. Pat. No. 9,556,146 to Bassaganya-Riera et al.; U.S. Pat. No. 9,839,635 to Bassaganya-Riera et al.; U.S. Pat. No. 10,028,950 to Bassaganya-Riera et al.; U.S. Pat. No. 10,201,538 to Bassaganya-Riera et al.; U.S. Pat. No. 10,493,072 to Bassaganya-Riera et al.; U.S. Pat. No. 10,682,349 to Bassaganya-Riera et al.; US 2019/0160100 A1 to Bassaganya-Riera et al.; Bissel et al 2016 (Bissel P, Boes K, Hinckley J, Jortner B S, Magnin-Bissel G, Werre S R, Ehrich M, Carbo A, Philipson C, Hontecillas R, Philipson N, Gandour R D, Bassaganya-Riera J. Exploratory Studies With BT-11: A Proposed Orally Active Therapeutic for Crohn's Disease. *Int J Toxicol*. 2016 September; 35(5):521-9); and Carbo et al. 2016 (Carbo A, Gandour R D, Hontecillas R, Philipson N, Uren A, Bassaganya-Riera J. An N,N-Bis(benzimidazolylpicolinoyl)piperazine (BT-11): A Novel Lanthionine Synthetase C-Like 2-Based Therapeutic for Inflammatory Bowel Disease. *J Med Chem*. 2016 Nov. 23; 59(22):10113-10126); Leber et al. 2018 (Leber A, Hontecillas R, Zoccoli-Rodriguez V, Bassaganya-Riera J. Activation of LANCL2 by BT-11 Ameliorates IBD by Supporting Regulatory T Cell Stability Through Immunometabolic Mechanisms. *Inflamm Bowel Dis*. 2018 Aug. 16; 24(9):1978-1991); Leber et al. 2019 *Int J Toxicol*. (Leber A, Hontecillas R, Zoccoli-Rodriguez V, Ehrich M, Davis J, Chauhan J. Bassaganya-Riera J. Nonlinical Toxicology and Toxicokinetic Profile of an Oral Lanthionine Synthetase C-Like 2 (LANCL2) Agonist, BT-11. *Int J Toxicol*. 2019 March/April; 38(2):96-109); Leber et al. 2019 *J Immunol*. (Leber A, Hontecillas R, Zoccoli-Rodriguez V, Chauhan J, Bassaganya-Riera J. Oral Treatment with BT-11 Ameliorates Inflammatory Bowel Disease by Enhancing Regulatory T Cell Responses in the Gut. *J Immunol*. 2019 Apr. 1; 202(7):2095-2104); and Leber et al 2020 (Leber A, Hontecillas R, Zoccoli-Rodriguez V, Colombel J F, Chauhan J, Ehrich M, Farinola N Bassaganya-Riera J The Safety, Tolerability, and Pharmacokinetics Profile of BT-11, an Oral, Gut-Restricted Lanthionine Synthetase C-Like 2 Agonist Investigational New Drug for Inflammatory Bowel Disease: A Randomized, Double-Blind, Placebo-Controlled Phase I Clinical Trial. *Inflamm Bowel Dis*. 2020 Mar. 4; 26(4):643-652).

The invention provides compounds that have been developed by novel medicinal chemistry approaches, and screened using in silico, in vitro, and in vivo techniques, to balance an ability to selectively bind to the LANCL2 protein with systemic bioavailability and potency. These compounds can affect a beneficial response in various disease conditions, including but not limited to, autoimmune, chronic inflammatory, inflammatory, metabolic, and infectious diseases.

SUMMARY OF THE INVENTION

The invention provides compounds of formula Z—Y-Q-Y' or pharmaceutically acceptable salts or esters thereof, wherein:

Z is:

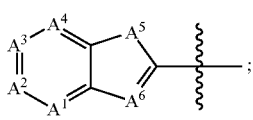

Y is:

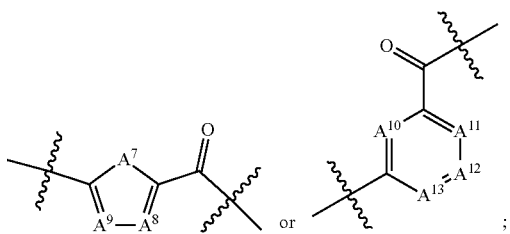

Q is piperazine-1,4-diyl; 2,5-diazabicyclo[2,2,1]heptane-2,5-diyl; 2,5-diazabicyclo[2,2,2]octane-2,5-diyl; 1,4-diazepane-1,4-diyl; benzene-1,4-diamine-$N^1,N^4$-diyl; ethane-1,2-diamine-$N^1,N^2$-diyl; $N^1,N^2$-dialkylethane-1,2-diamine-$N^1,N^2$-diyl; propane-1,3-diamine-$N^1,N^3$-diyl; $N^1,N^3$-dialkylpropane-1,3-diamine-$N^1,N^3$-diyl; 1,4-diaminoanthracene-9,10-dione-1,4-diyl; substituted piperazine-1,4-diyl, or substituted C6 arene-1,4-diamine-$N^1,N^4$-diyl;

Y' is:

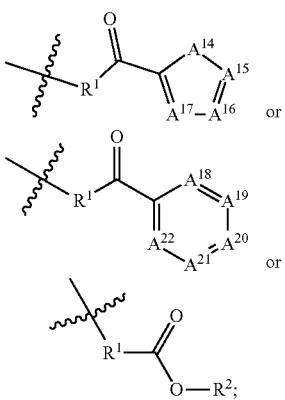

--- between $A^{15}$ and $A^{16}$ is a bond or absent;

$A^1, A^2, A^3, A^4, A^6, A^8, A^9, A^{10}, A^{11}, A^{12}, A^{13}, A^{17}, A^{18}, A^{19}, A^{20}, A^{21}$, and $A^{22}$ are each independently $C(R^3)$ or N.

$A^5, A^7$, and $A^{14}$ are each independently $N(R^3), C(R^3)_2$, O, or S;

$A^{15}$ and $A^{16}$ are each independently N or $C(R^3)$ when --- is a bond, and are each independently $N(R^3), C(R^3)_2$, O, or S when --- is absent;

$R^1$ is optionally substituted alkylene optionally containing one or two heteroatom(s), optionally substituted alkenylene optionally containing one or two heteroatom(s), optionally substituted alkynylene optionally containing one or two heteroatom(s), an oxygen atom, a sulfur atom, or $N(R^4)$;

$R^2$ is an electron pair, a hydrogen atom, optionally substituted alkyl, optionally substituted alkenyl, optionally substituted alkynyl, optionally substituted cycloalkyl, optionally substituted cycloalkenyl, optionally substituted aryl, optionally substituted heteroaryl, or an optionally substituted non-aromatic heterocyclic group;

$R^3$ in each instance is independently a hydrogen atom, a halogen atom, optionally substituted alkyl, optionally substituted alkenyl, optionally substituted alkynyl, optionally substituted cycloalkyl, optionally substituted cycloalkenyl, hydroxy, carboxy, optionally substituted alkyloxy, optionally substituted alkenyloxy, optionally substituted alkynyloxy, optionally substituted cycloalkyloxy, optionally substituted cycloalkenyloxy, mercapto, optionally substituted alkylthio, optionally substituted alkenylthio, optionally substituted alkynylthio, optionally substituted alkylsulfinyl, optionally substituted alkylsulfonyl, optionally substituted alkylsulfonyloxy, optionally substituted cycloalkylthio, optionally substituted cycloalkylsulfinyl, optionally substituted cycloalkylsulfonyl, optionally substituted cycloalkylsulfonyloxy, optionally substituted cycloalkenylthio, optionally substituted cycloalkenylsulfinyl, optionally substituted cycloalkenylsulfonyl, optionally substituted cycloalkenylsulfonyloxy, optionally substituted amino, acyl, optionally substituted alkyloxycarbonyl, optionally substituted alkenyloxycarbonyl, optionally substituted alkynyloxycarbonyl, optionally substituted aryloxycarbonyl, optionally substituted carbamoyl, optionally substituted sulfamoyl, cyano, nitro, optionally substituted aryl, optionally substituted aryloxy, optionally substituted arylthio, optionally substituted arylsulfinyl, optionally substituted arylsulfonyl, optionally substituted arylsulfonyloxy, optionally substituted heteroaryl, optionally substituted heteroaryloxy, optionally substituted heteroarylthio, optionally substituted heteroarylsulfinyl, optionally substituted heteroarylsulfonyl, optionally substituted heteroarylsulfonyloxy, or an optionally substituted non-aromatic heterocyclic group; and $R^4$ is a hydrogen atom, optionally substituted alkyl, optionally substituted alkenyl, optionally substituted alkynyl, optionally substituted cycloalkyl, acyl, optionally substituted alkyloxy, optionally substituted aryl, optionally substituted heteroaryl, or an optionally substituted non-aromatic heterocyclic group.

In some versions, $A^1$ is $C(R^3)$. In some versions, $A^1$ is N. In some versions, $A^2$ is $C(R^3)$. In some versions, $A^2$ is N. In some versions, $A^3$ is $C(R^3)$. In some versions, $A^3$ is N. In some versions, $A^4$ is $C(R^3)$. In some versions, $A^4$ is N. In some versions, $A^5$ is $N(R^3)$. In some versions, $A^5$ is O. In some versions, $A^6$ is $C(R^3)$. In some versions, $A^6$ is N. In some versions, $A, A^2$, and $A^3$ are $C(R^3)$; $A^5$ is $N(R^3)$; and $A^6$ is N. In some versions, $A, A^2, A^3$, and $A^4$ are $C(R^3)$; $A^5$ is $N(R^3)$; and $A^6$ is N.

In some versions, Y is:

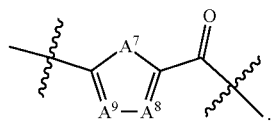

In some versions, $A^7$ is $N(R^3)$. In some versions, $A^7$ is $N(R^3)$, wherein the $R^3$ in the $N(R^3)$ is hydrogen or halogen. In some versions, $A^7$ is O. In some versions, $A^8$ is $C(R^3)$. In some versions, $A^8$ is N. In some versions, $A^9$ is $C(R^3)$. In some versions, $A^9$ is N.

In some versions, Y is:

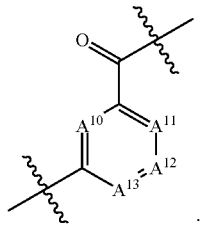

In some versions, $A^{10}$ is $C(R^3)$. In some versions, $A^{10}$ is N. In some versions, A is $C(R^3)$. In some versions, $A^{11}$ is N. In some versions, $A^{12}$ is $C(R^3)$. In some versions, $A^{12}$ is N. In some versions, $A^{13}$ is $C(R^3)$. In some versions, $A^{13}$ is N. In some versions, A, $A^{12}$, and $A^{13}$ are $C(R^3)$. In some versions, $A^{10}$ is N, and A, $A^{12}$, and $A^{13}$ are $C(R^3)$.

In some versions, Q is piperazine-1,4-diyl or substituted piperazine-1,4-diyl. In some versions, Q is piperazine-1,4-diyl. In some versions, Q is substituted piperazine-1,4-diyl. In some versions, the substituted piperazine-1,4-diyl is:

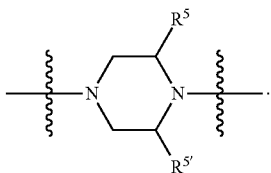

In some versions one or both of $R^5$ and $R^{5'}$ are independently alkyl optionally substituted at one to three position(s) with a substituent independently selected from a halogen atom and alkyloxy; oxo; cycloalkyl; alkenyl; alkynyl; hydroxy; alkyloxy optionally substituted at one to three position(s) with a substituent independently selected from a halogen atom and phenyl optionally substituted with one to three substituent(s) independently selected from a halogen atom, alkyl, alkyloxy, cyano, and nitro; aryloxy optionally substituted at one to three positions with a substituent independently selected from a halogen atom, alkyl, alkyloxy, cyano, and nitro; mercapto; alkylthio; a halogen atom; nitro; cyano; carboxy; alkyloxycarbonyl; acyl; alkylsulfonyl; optionally substituted amino; optionally substituted carbamoyl; aryl optionally substituted with one to three substituent(s) independently selected from a halogen atom, alkyl, alkyloxy, cyano, and nitro; heteroaryl optionally substituted at one to three position(s) with a substituent independently selected from a halogen atom and alkyl; and non-aromatic heterocyclic group optionally substituted at one to three position(s) with a substituent independently selected from a halogen atom and alkyl. In some versions, one or both of $R^5$ and $R^{5'}$ are independently oxo, hydroxy, or optionally substituted alkyloxy. In some versions, one or both of $R^5$ and $R^{5'}$ are oxo. In some versions, $R^5$ and $R^{5'}$ are each oxo.

In some versions, Y' is:

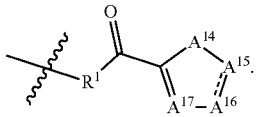

In some versions, $A^{14}$ is $N(R^3)$. In some versions, $A^{14}$ is $N(R^3)$, wherein the $R^3$ in the $N(R^3)$ is hydrogen or halogen. In some versions, $A^{14}$ is O. In some versions, --- is a bond, and $A^{15}$ is $C(R^3)$. In some versions, --- is a bond, and $A^{15}$ is N. In some versions, --- is a bond, and $A^{16}$ is $C(R^3)$. In some versions, --- is a bond, and $A^{16}$ is N. In some versions, --- is absent, and $A^{15}$ is $C(R^3)_2$. In some versions, --- is absent, and $A^{15}$ is $N(R^3)$. In some versions, --- is absent, and $A^{16}$ is $C(R^3)_2$. In some versions, --- is absent, and $A^{16}$ is —C(H)(C1-C3 alkyl)-. In some versions, --- is absent, and $A^{16}$ is $N(R^3)$. In some versions, $A^{17}$ is $C(R^3)$. In some versions, $A^{17}$ is N.

In some versions, Y' is:

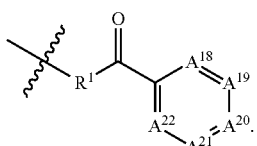

In some versions, $A^{18}$ is $C(R^3)$. In some versions, $A^{18}$ is N. In some versions, $A^{19}$ is $C(R^3)$. In some versions, $A^{19}$ is N. In some versions, $A^{20}$ is $C(R^3)$. In some versions, $A^{20}$ is N. In some versions, $A^{21}$ is $C(R^3)$. In some versions, $A^{21}$ is N. In some versions, $A^{22}$ is $C(R^3)$. In some versions, $A^{22}$ is N. In some versions, $A^{18}$, $A^{20}$, and $A^{22}$ are $C(R^3)$. In some versions, $A^{18}$, $A^{19}$, $A^{20}$, $A^{21}$, and $A^{22}$ are $C(R^3)$. In some versions, $A^{19}$ is N. In some versions, $A^{21}$ is N. In some versions, $A^{19}$ and $A^{21}$ are both N. In some versions, $A^{18}$, $A^{20}$, and $A^{22}$ are $C(R^3)$, and one or both of $A^{19}$ and $A^{21}$ is N. In some versions, $A^{18}$, $A^{20}$, and $A^{22}$ are $C(R^3)$ and both of $A^{19}$ and $A^{21}$ are N. In some versions, $A^{20}$ is $C(R^3)$, and the $R^3$ on the $C(R^3)$ of $A^{20}$ is any substituent described herein for $R^3$ except hydrogen. In some versions, $A^{20}$ is $C(R^3)$, and the $R^3$ on the $C(R^3)$ of $A^{20}$ is any substituent described herein for $R^3$ except hydrogen and halogen. In some versions, $A^{20}$ is $C(R^3)$, and the $R^3$ on the $C(R^3)$ of $A^{20}$ is cyano. In some versions, $A^{18}$, $A^{19}$, $A^{21}$, $A^{22}$ are each CH, $A^{20}$ is $C(R^3)$, and the $R^3$ on the $C(R^3)$ of $A^{20}$ is cyano.

In some versions, Y' is:

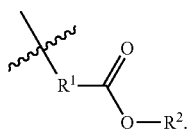

In some versions, $R^2$ is an electron pair. In some versions, $R^2$ is a hydrogen atom.

In some versions, $R^1$ is optionally substituted alkylene optionally containing one or two heteroatom(s). In some versions, $R^1$ is optionally substituted alkylene. In some versions, $R^1$ is optionally substituted C, C2, or C3 alkylene. In some versions, $R^1$ is unsubstituted C1, C2, or C3 alkylene. In some versions, $R^1$ is unsubstituted C1 alkylene.

In some versions, $R^1$ is C1, C2, or C3 alkylene substituted with one or more alkyl groups. In some versions, $R^1$ is C1 alkylene substituted with one or two alkyl groups. In some versions, $R^1$ is C1 alkylene substituted with two alkyl groups.

In some versions, Z—Y-Q-Y' is:

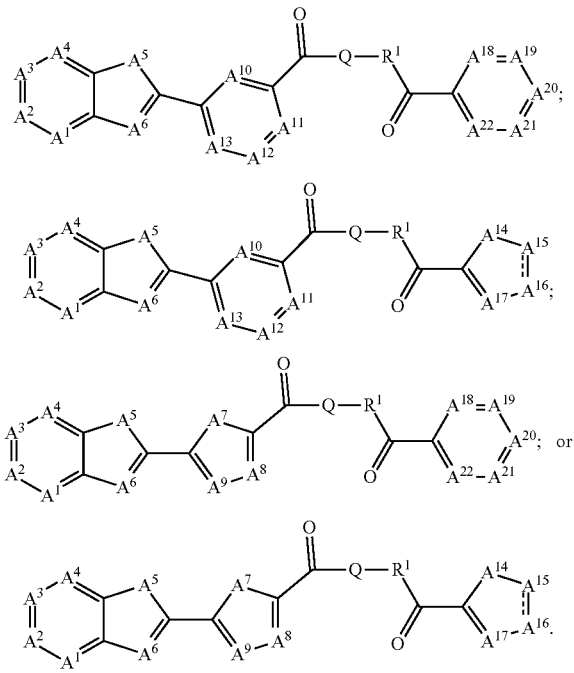

In some versions, Z—Y-Q-Y' is:

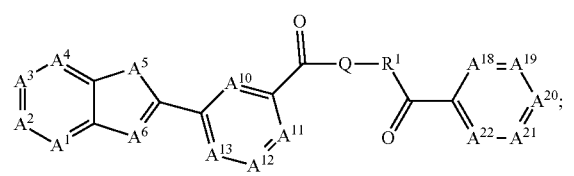

Q is piperazine-1,4-diyl or substituted piperazine-1,4-diyl; $A^1$, $A^2$, $A^3$, $A^4$, $A^{11}$, $A^{12}$, $A^{13}$, $A^{18}$, $A^{20}$, and $A^{22}$ are $C(R^3)$; $A^5$ is $N(R^3)$; $A^6$ and $A^{10}$ are N; and $R^1$ is optionally substituted alkylene.

In some versions, $R^3$ in each instance, unless otherwise defined, is independently a hydrogen atom, a halogen atom, C1-C6 alkyl, hydroxy, methoxy, carboxyl, acetyl, trifluoromethyl, amino, cycloalkyl, a non-aromatic heterocyclic group, aryl, or heteroaryl.

In some versions the compound is selected from.

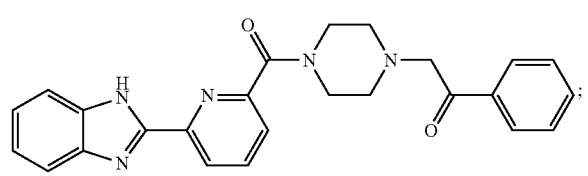 [SMILES: CC(C)(C(=O)c1ccccc1)N1CCN(C(=O)c2cccc(-c3nc4ccccc4[nH]3)n2)CC1]

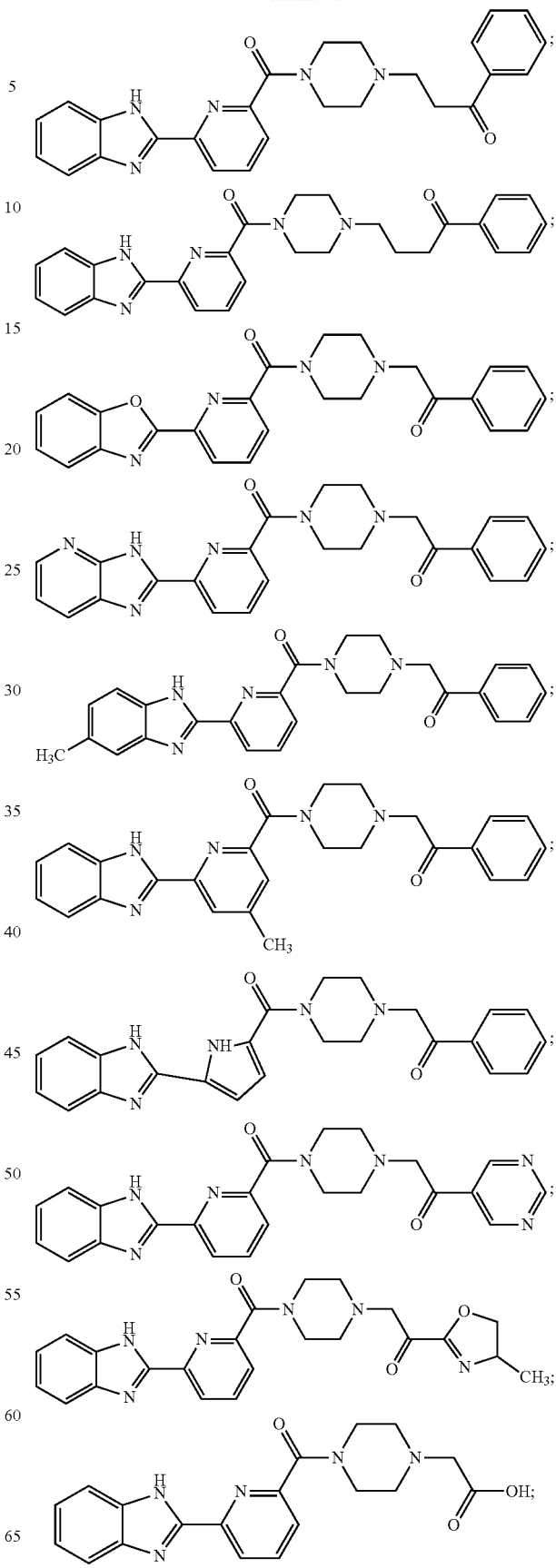

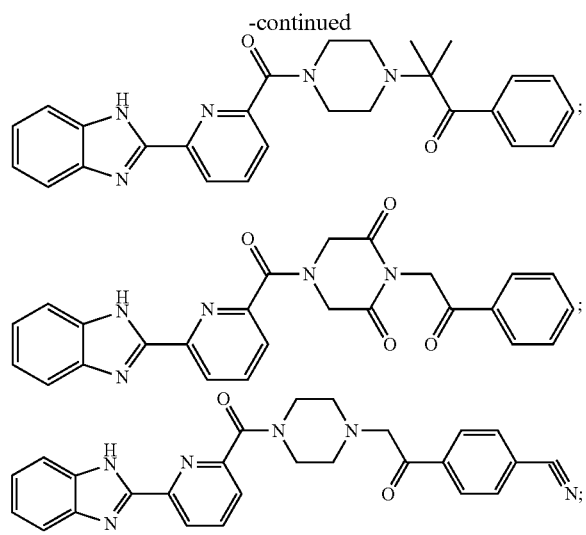

or a salt or ester of any of the foregoing.

Any version described above or elsewhere herein can be combined with any one or more other non-mutually exclusive versions described above or elsewhere herein.

The invention provides methods of treating a condition in an animal with any one or more of the compounds described herein. The methods may comprise administering an effective amount of one or more of the compounds described herein to the animal. The effective amount is an amount effective to treat the condition in the animal. The condition can comprise any one or more of the conditions described herein. In some versions, the condition comprises an autoimmune disease. In some versions, the condition comprises an inflammatory disease. In some versions, the condition comprises a chronic inflammatory disease. In some versions, the condition comprises inflammatory bowel disease, such as ulcerative colitis and/or Crohn's disease. In some versions, the condition comprises diabetes. In some versions, the condition comprises an infectious disease. In some versions, the condition comprises lupus, such as systemic lupus erythematosus. In some versions, the condition comprises Sjögren's syndrome. In some versions, the condition comprises rheumatoid arthritis. In some versions, the condition comprises type 1 diabetes. In some versions, the condition comprises a viral disease such as influenza, Zika virus infection, and coronavirus infection. In some versions, the condition comprises nonalcoholic steatohepatitis.

In some versions, the condition comprises a hyperproliferative disorder, an inborn error of metabolism, a chronic immunometabolic disease, organ transplant rejection, and/or chronic pain. In some versions, the hyperproliferative disorder comprises cancer. In some versions, the cancer comprises a cancer of the gastrointestinal tract. In some versions, the cancer of the gastrointestinal tract comprises colorectal cancer. In some versions, the hyperproliferative disorder comprises familial adenomatous polyposis. In some versions, the inborn error of metabolism comprises a glycogen storage disease. In some versions, the glycogen storage disease comprises Andersen disease. In some versions, the chronic immunometabolic disease comprises cardiovascular disease. In some versions, the cardiovascular disease comprises atherosclerosis. In some versions, the chronic immunometabolic disease comprises hypertension. In some versions, the autoimmune disease comprises a cancer-immunotherapy-induced autoimmune disease. In some versions, the cancer-immunotherapy-induced autoimmune disease comprises a cancer immunotherapy-induced rheumatic disease. In some versions, the inflammatory disorder comprises acute colonic diverticulitis. In some versions, the inflammatory disorder comprises radiation-induced inflammation of the gastrointestinal tract. In some versions, the radiation-induced inflammation of the gastrointestinal tract comprises at least one of radiation proctitis, radiation enteritis, and radiation proctosigmoiditis. In some versions, the chronic pain comprises fibromyalgia.

The invention also provides methods of generating a prepared cell from a precursor cell with the compounds described herein. The methods may comprise contacting the precursor cell, in vitro, with one or more of the compounds described herein to generate the prepared cell. The precursor cell can be contacted with the compound in an amount and for a time effective to induce a compound-dependent difference in the prepared cells with respect to the precursor cells. In some versions, the contacting comprises contacting the precursor cells with the compound and an agent comprising one or more of all-trans-retinoic acid, TGF-β, phorbol myristate acetate, ionomycin, rapamycin, and IL-2. In some versions, the precursor cells comprise immune cells. In some versions, the precursor cells comprise white blood cells. In some versions, the precursor cells comprise cells selected from the group consisting of peripheral blood mononuclear cells and lamina propria mononuclear cells. In some versions, the precursor cells comprise T cells. In some versions, the precursor cells comprise naïve CD4+ T cells. In some versions, the prepared cells comprise Treg cells. In some versions, the prepared cell is differentiated from the precursor cell. In some versions, the compound-dependent difference comprises a difference in gene expression in the prepared cells with respect to the precursor cells. In some versions, the compound-dependent difference comprises at least one of an increase in expression of IL-10 or an ortholog thereof, an increase in expression of FOXP3 or an ortholog thereof, a decrease in expression of TNFα or an ortholog thereof, a decrease in expression of IFNγ or an ortholog thereof, a decrease in expression of Tbet or an ortholog thereof, an increase in expression of Lag3 or an ortholog thereof, an increase in expression of Socs2 or an ortholog thereof, an increase in expression of Irf7 or an ortholog thereof, an increase in expression of P2rx7 or an ortholog thereof, an increase in expression of Capn3 or an ortholog thereof, an increase in expression of Ikzf2 or an ortholog thereof, an increase in expression of Stat5a or an ortholog thereof, an increase in expression of Pten or an ortholog thereof, an increase in expression of Foxo1 or an ortholog thereof, an increase in expression of Phlpp1 or an ortholog thereof, an increase in phosphorylation of STAT5a or an ortholog thereof, an increase in FOXO1 phosphorylation or an ortholog thereof, and an increase in pyruvate kinase activity.

The invention also provides isolated cells generated by contacting a precursor cell, in vitro, with one or more of the compounds described herein to generate a prepared cell.

The invention also provides methods of treating a condition in an animal with a prepared cell as described herein. The methods comprise administering the prepared cell to the animal in an amount sufficient to treat the condition. The condition can comprise any condition described above or elsewhere herein.

The objects and advantages of the invention will appear more fully from the following detailed description of the preferred embodiment of the invention made in conjunction with the accompanying drawings.

BRIEF DESCRIPTION OF THE DRAWINGS

Figure 1A:
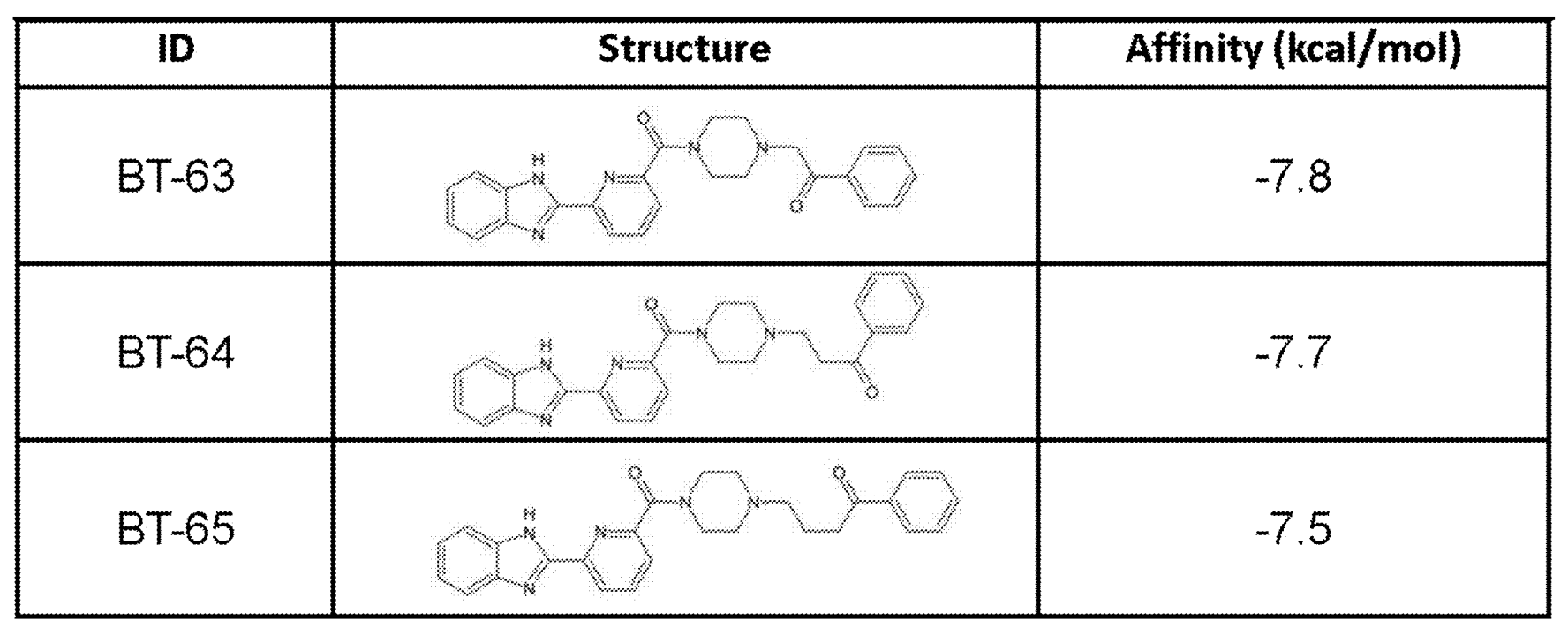

FIGS. 1A-1C. Computational prediction of binding of selected compounds to LANCL2 in kcal/mol.

FIGS. 18A-18C. In vivo validation of BT-104-B efficacy in an NZB/W F1 model of SLE. Percentages of IL17+(FIG. 18A), IL21+(FIG. 18B), and CD25+ FOXP3+ CD4+ T cells (FIG. 18C) in the spleens of NZB/W F1 mice after 12 weeks of daily oral treatment with vehicle or BT-104-B (20 mg/kg). Statistical significance (P<0.05) is marked by asterisks.

DETAILED DESCRIPTION OF THE INVENTION

Figure 1C:
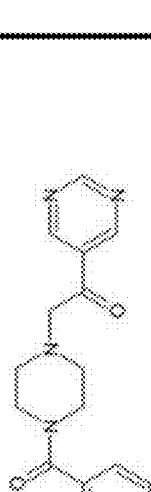

Unless otherwise stated, the following definitions are used throughout the present application:

Analysis of Variance (ANOVA): Arithmetic process for partitioning the overall variation in data sets into specific components based on sources of variation. It has been used to determine whether numerical differences between treatment groups are statistically significant.

Conjugated diene: A molecule containing two double bonds separated by a single bond.

Enantiomer: Optical isomer; chemical classification of molecules based on their ability to rotate the plain of polarization clockwise (+) or anti-clockwise (−).

Substantially pure: Having a purity of at least 90% by weight, preferably at least 95% by weight such as at least 98%, 99% or about 100% by weight.

IBD: Inflammatory bowel disease (IBD) involves chronic inflammation of all or part of your digestive tract. IBD primarily includes ulcerative colitis and Crohn's disease. Both usually involve severe diarrhea, pain, fatigue and weight loss. IBD can be debilitating and sometimes leads to life-threatening complications.

Ulcerative colitis (UC): UC is an IBD that causes long-lasting inflammation and sores (ulcers) in the innermost lining of your large intestine (colon) and rectum. Crohn's Disease: Crohn's disease is an IBD that cause inflammation of the lining of your digestive tract. In Crohn's disease, inflammation often spreads deep into affected tissues. The inflammation can involve different areas of the digestive tract—the large intestine, small intestine or both.

IL-10: Interleukin-10 (IL-10), also known as human cytokine synthesis inhibitory factor (CSIF), is an anti-inflammatory cytokine. In humans, IL-10 is encoded by the IL10 gene.

FOXP3: FOXP3 (forkhead box P3) also known as scurfin is a protein involved in immune system responses. A member of the FOX protein family, FOXP3 appears to function as a master regulator (transcription factor) in the development and function of regulatory T cells.

TNF-alpha: Tumor necrosis factor (TNF, cachexin, or cachectin, and formerly known as tumor necrosis factor alpha or TNFα) is cytokine involved in systemic inflammation and is a member of a group of cytokines that stimulate the acute phase reaction.

MCP1: Monocyte chemoattractant protein-1. An older term for a CC cytokine which is critical for development of atherosclerotic lesions, found in endothelial cells, macrophages and in vascular smooth muscle cells of patients undergoing coronary artery bypass procedures. The officially preferred term is now chemokine (C—C motif) ligand 2.

Interferon gamma: Interferon gamma is a pro-inflammatory dimerized soluble cytokine that is the only member of the type II class of interferons.

Leukocytic infiltration: Leukocyte infiltration refers to the process of moving or infiltrating of the leukocytes into the injured tissue to begin the repair process.

Type 1 diabetes: An autoimmune disease characterized as a chronic condition in which the pancreas produces little to no insulin as a result of immunological destruction of insulin-producing beta cells within pancreatic islets. The insulin deficiency leads to chronic hyperglycemia that can cause organ damage, shortened lifespan and reduced quality of life. The disease is also referred to as juvenile diabetes or insulin-dependent diabetes.

Systemic lupus erythematosus: An autoimmune disease in which the immune system reacts to nuclear antigens and forms immune complexes that can aggregate or cause damage to multiple organ systems including skin, joints, kidneys, brain, the heart and cardiovascular systems and other organs.

The term "halogen atom" refers to a fluorine atom, a chlorine atom, a bromine atom and an iodine atom. A fluorine atom, a chlorine atom, and a bromine atom are preferred.

The term "hetero atom" refers to an oxygen atom, a sulfur atom, and a nitrogen atom.

The term "alkyl" includes a monovalent straight or branched hydrocarbon group having one to eight carbon atom(s). Examples include methyl, ethyl, n-propyl, isopropyl, n-butyl, isobutyl, sec-butyl, tert-butyl, n-pentyl, isopentyl, neo-pentyl, n-hexyl, isohexyl, n-heptyl, n-octyl, and the like. C1-C6 alkyl is preferred. C1-C4 alkyl or C1-C3 alkyl is further preferred. When a number of carbons is specified, it means "alkyl" having the carbon number within the range.

The term "alkenyl" includes a monovalent straight or branched hydrocarbon group having two to eight carbon atoms and one or more double bond(s). Examples include vinyl, allyl, 1-propenyl, 2-butenyl, 2-pentenyl, 2-hexenyl, 2-heptenyl, 2-octenyl, and the like. C2-C6 alkenyl is preferred. C2-C4 alkenyl is further preferred.

The term "alkynyl" includes a monovalent straight or branched hydrocarbon group having two to eight carbon atoms and one or more triple bond(s). Examples include ethynyl, 1-propynyl, 2-propynyl, 2-butynyl, 2-pentynyl, 2-hexynyl, 2-heptynyl, 2-octynyl, and the like. C2-C6 alkynyl is preferred. C2-C4 alkynyl is further preferred.

The term "cycloalkyl" includes a cycloalkyl having three to eight carbon atoms. Examples include cyclopropyl, cyclobutyl, cyclopentyl, cyclohexyl, cycloheptyl, cyclooctyl, and the like. C3-C6 cycloalkyl is preferred.

The term "cycloalkenyl" includes a cycloalkenyl having three to eight carbon atoms. Examples include cyclopropenyl, cyclobutenyl, cyclopentenyl, cyclohexenyl, cycloheptenyl, cyclooctenyl, and the like. C3-C6 cycloalkenyl is preferred.

The term "alkyloxy" includes a group wherein an oxygen atom is substituted with one "alkyl" as described herein. Examples include methyloxy, ethyloxy, n-propyloxy, isopropyloxy, n-butyloxy, isobutyloxy, sec-butyloxy, tert-butyloxy, n-pentyloxy, isopentyloxy, 2-pentyloxy, 3-pentyloxy, n-hexyloxy, isohexyloxy, 2-hexyloxy, 3-hexyloxy, n-heptyloxy, n-octyloxy, and the like. C1-C6 alkyloxy is preferred. C1-C4 alkyloxy or C1-C3 alkyloxy is further preferred. When a number of carbons is specified, it means "alkyloxy" having the carbon number within the range.

The term "alkenyloxy" includes a group wherein an oxygen atom is substituted with one "alkenyl" as described herein. Examples include vinyloxy, allyloxy, 1-propenyloxy, 2-butenyloxy, 2-pentenyloxy, 2-hexenyloxy, 2-heptenyloxy, 2-octenyloxy, and the like. C2-C6 alkenyloxy is preferred. Moreover, C2-C4 alkenyloxy is further preferred. When a number of carbons is specified, it means "alkenyloxy" having the carbon number within the range.

The term "alkynyloxy" includes a group wherein an oxygen atom is substituted with one "alkynyl" as described herein. Examples include ethynyloxy, 1-propynyloxy, 2-propynyloxy, 2-butynyloxy, 2-pentynyloxy, 2-hexynyloxy, 2-heptynyloxy, 2-octynyloxy, and the like. C2-C6 alkynyloxy is preferred. C2-C4 alkynyloxy is further preferred. When a number of carbons is specified, it means "alkynyloxy" having the carbon number within the range.

The term "cycloalkyloxy" includes a group wherein an oxygen atom is substituted with one "cycloalkyl" as described herein. Examples include cyclopropyloxy, cyclobutyloxy, cyclopentyloxy, cyclohexyloxy, cycloheptyloxy, and cyclooctyloxy. C3-C6 cycloalkyloxy is preferred. When a number of carbons is specified, it means "cycloalkyloxy" having the carbon number within the range.

The term "cycloalkenyloxy" includes a group wherein an oxygen atom is substituted with one "cycloalkenyl" as described herein. Examples include cyclopropenyloxy, cyclobutenyloxy, cyclopentenyloxy, cyclohexenyloxy, cycloheptenyloxy, and cyclooctenyloxy. C3-C6 cycloalkenyloxy is preferred. When a number of carbons is specified, it means "cycloalkenyloxy" having the carbon number within the range.

The term "alkylthio" includes a group wherein a sulfur atom is substituted with one "alkyl" as described herein. Examples include methylthio, ethylthio, n-propylthio, isopropylthio, n-butylthio, isobutylthio, sec-butylthio, tert-butylthio, n-pentylthio, isopentylthio, 2-pentylthio, 3-pentylthio, n-hexylthio, isohexylthio, 2-hexylthio, 3-hexylthio, n-heptylthio, n-octylthio, and the like. C1-C6 Alkylthio is preferred. C1-C4 alkylthio is further preferred. When a number of carbons is specified, it means "alkylthio" having the carbon number within the range.

The term "alkenylthio" includes a group wherein a sulfur atom is substituted with one "alkenyl" as described herein. Examples include vinylthio, allylthio, 1-propenylthio, 2-butenylthio, 2-pentenylthio, 2-hexenylthio, 2-heptenylthio, 2-octenylthio, and the like. C2-C6 Alkenylthio is preferred. C2-C4 alkenylthio is further preferred. When a number of carbons is specified, it means "alkenylthio" having the carbon number within the range.

The term "alkynylthio" includes a group wherein a sulfur atom is substituted with one "alkynyl" as described herein. Examples include ethynylthio, 1-propynylthio, 2-propynylthio, 2-butynylthio, 2-pentynylthio, 2-hexynylthio, 2-heptynylthio, 2-octynylthio, and the like. C2-C6 alkynylthio is preferred. C2-C4 alkynylthio is further preferred. When a number of carbons is specified, it means "alkynylthio" having the carbon number within the range.

The term "alkylsulfinyl" includes a group wherein sulfinyl is substituted with one "alkyl" as described herein. Examples include methylsulfinyl, ethylsulfinyl, n-propylsulfinyl, isopropylsulfinyl, n-butylsulfinyl, isobutylsulfinyl, sec-butylsulfinyl, tert-butylsulfinyl, n-pentylsulfinyl, isopentylsulfinyl, 2-pentylsulfinyl, 3-pentylsulfinyl, n-hexylsulfinyl, isohexylsulfinyl, 2-hexylsulfinyl, 3-hexylsulfinyl, n-heptylsulfinyl, n-octylsulfinyl, and the like. C1-C6 alkylsulfinyl is preferred. C1-C4 alkylsulfinyl is further preferred.

The term "alkylsulfonyl" includes a group wherein sulfonyl is substituted with one "alkyl" as described herein. Examples include methylsulfonyl, ethylsulfonyl, n-propylsulfonyl, isopropylsulfonyl, n-butylsulfonyl, isobutylsulfonyl, sec-butylsulfonyl, tert-butylsulfonyl, n-pentylsulfonyl, isopentylsulfonyl, 2-pentylsulfonyl, 3-pentylsulfonyl, n-hexylsulfonyl, iso hexylsulfonyl, 2-hexylsulfonyl, 3-hexylsulfonyl, n-heptylsulfonyl, n-octylsulfonyl, and the like. C1-C6 alkylsulfonyl is preferred. C1-C4 alkylsulfonyl is further preferred.

The term "alkylsulfonyloxy" includes a group wherein an oxygen atom is substituted with one "alkylsulfonyl" as described herein. Examples include methylsulfonyloxy, ethylsulfonyloxy, n-propylsulfonyloxy, isopropylsulfonyloxy, n-butylsulfonyloxy, isobutylsulfonyloxy, sec-butylsulfonyloxy, tert-butylsulfonyloxy, n-pentylsulfonyloxy, isopentylsulfonyloxy, 2-pentylsulfonyloxy, 3-pentylsulfonyloxy, n-hexylsulfonyloxy, isohexylsulfonyloxy, 2-hexylsulfonyloxy, 3-hexylsulfonyloxy, n-heptylsulfonyloxy, n-octylsulfonyloxy, and the like. C1-C6 alkylsulfonyl is preferred. C1-C4 alkylsulfonyl is further preferred.

The term "cycloalkylthio" includes a group wherein a sulfur atom is substituted with one "cycloalkyl" as described herein. Examples include cyclopropylthio, cyclobutylthio, cyclopentylthio, cyclohexylthio, cycloheptylthio, cyclooctylthio, and the like. C3-C6 cycloalkylthio is preferred. When a number of carbons is specified, it means "cycloalkylthio" having the carbon number within the range.

The term "cycloalkylsulfinyl" includes a group in which sulfinyl is substituted with one "cycloalkyl" as described herein. Examples include cyclopropylsulfinyl, cyclobutylsulfinyl, cyclopentylsulfinyl, cyclohexylsulfinyl, cycloheptylsulfinyl, and cyclooctylsulfinyl are exemplified. Preferably C3-C6 cycloalkylsulfinyl.

The term "cycloalkylsulfonyl" includes a group in which sulfonyl is substituted with one "cycloalkyl" as described herein. Examples include cyclopropylsulfonyl, cyclobutylsulfonyl, cyclopentylsulfonyl, cyclohexylsulfonyl, cycloheptylsulfonyl, and cyclooctylsulfonyl. C3-C6 cycloalkylsulfonyl is preferred.

The term "cycloalkylsulfonyloxy" includes a group in which an oxygen atom is substituted with one "cycloalkylsulfonyl" as described herein. Examples include cyclopropylsulfonyloxy, cyclobutylsulfonyloxy, cyclopentyl sulfonyloxy, cyclohexyl sulfonyloxy, cycloheptylsulfonyloxy, and cyclooctylsulfonyloxy. C3-C6 cycloalkylsulfonyloxy is preferred.

The term "cycloalkenylthio" includes a group in which a sulfur atom is substituted with one "cycloalkenyl" as described herein. Examples include cyclopropenylthio, cyclobutenylthio, cyclopentenylthio, cyclohexenylthio, cycloheptenylthio, and cyclooctenylthio. C3-C6 cycloalkenylthio is preferred. When a number of carbons is specified, it means "cycloalkenylthio" having the carbon number within the range.

The term "cycloalkenylsulfinyl" includes a group in which sulfinyl is substituted with one "cycloalkenyl" as described herein. Examples include cyclopropenylsulfinyl, cyclobutenylsulfinyl, cyclopentenylsulfinyl, cyclohexenylsulfinyl, cycloheptenylsulfinyl, and cyclooctenylsulfinyl. C3-C6 cycloalkenylsulfinyl is preferred.

The term "cycloalkenylsulfonyl" includes a group in which sulfonyl is substituted with one "cycloalkenyl" as described herein. Examples include cyclopropenylsulfonyl, cyclobutenylsulfonyl, cyclopentenylsulfonyl, cyclohexenylsulfonyl, cycloheptenylsulfonyl, and cyclooctenylsulfonyl. Preferably C3-C6 cycloalkenylsulfonyl is preferred.

The term "cycloalkenylsulfonyloxy" includes a group in which an oxygen atom is substituted with one "cycloalkenylsulfonyl" described as described herein. Examples include cyclopropenylsulfonyloxy, cyclobutenylsulfonyloxy, cyclopentenylsulfonyloxy, cyclohexenylsulfonyloxy, cycloheptenylsulfonyloxy, and cyclooctenylsulfonyloxy. C3-C6 cycloalkenylsulfonyloxy is preferred.

The term "alkyloxycarbonyl" includes a group in which carbonyl is substituted with one "alkyloxy" as described herein. Examples include methyloxycarbonyl, ethyloxycarbonyl, n-propyloxycarbonyl, isopropyloxycarbonyl, n-butyloxycarbonyl, tert-butyloxycarbonyl, and n-pentyloxycarbonyl. C1-C6 or C1-C4 alkyloxycarbonyl is preferred. C1-C2 alkyloxycarbonyl is further preferred.

The term "alkenyloxycarbonyl" includes a group in which carbonyl is substituted with one "alkenyloxy" as described herein. Examples include vinyloxycarbonyl, allyloxycarbonyl, 1-propenyloxycarbonyl, 2-butenyloxycarbonyl, and 2-pentenyloxyarbonyl. C2-C6 or C2-C4 alkyloxycarbonyl is preferred.

The term "alkynyloxycarbonyl" includes a group in which carbonyl is substituted with one "alkynyloxy" as described herein. Examples include ethynyloxycarbonyl, 1-propynyloxycarbonyl, 2-propynyloxycarbonyl, 2-butynyloxyarbonyl, and 2-pentynyloxycarbonyl. C2-C6 or C2-C4 alkynyloxycarbonyl is preferred.

The term "acyl" includes alkylcarbonyl wherein the part of alkyl is "alkyl" as described herein, alkenylcarbonyl wherein the part of alkenyl is "alkenyl" as described herein, alkynylcarbonyl wherein the part of alkynyl is "alkynyl" as described herein, cycloalkylcarbonyl wherein the part of cycloalkyl is "cycloalkyl" as described herein, arylcarbonyl wherein the part of aryl is "aryl" as described herein, heteroarylcarbonyl wherein the part of heteroaryl is "heteroaryl" as described herein, and non-aromatic heterocyclic-carbonyl wherein the part of non-aromatic heterocyclic group is "non-aromatic heterocyclic group" as described herein. "Alkyl," "alkenyl," "alkynyl," "cycloalkyl," "aryl," "heteroaryl," and "non-aromatic heterocyclic group" may be substituted respectively with substituent groups exemplified in "optionally substituted alkyl," "optionally substituted alkenyl," "optionally substituted alkynyl," "optionally substituted cycloalkyl," "optionally substituted aryl," "optionally substituted heteroaryl," and "optionally substituted non-aromatic heterocyclic group" as described herein.

Examples of the acyl group include acetyl, propionyl, butyroyl, cyclohexylcarbonyl, benzoyl, pyridinecarbonyl, and the like.

The term "optionally substituted amino" includes an amino group which may be substituted with one or two group(s) of "alkyl" as described herein, "alkenyl" as described herein, "alkynyl" as described herein, "cycloalkyl" as described herein, "cycloalkynyl" as described herein, "aryl" as described herein, "heteroaryl" as described herein, "acyl" as described herein, "alkyloxycarbonyl" as described herein, "alkenyloxycarbonyl" as described herein, "alkynyloxycarbonyl" as described herein, "alkyl sulfonyl," "alkenylsulfonyl," "alkynylsulfonyl," "arylsulfonyl," and/or "heteroarylsulfonyl" as described herein. Examples of the optionally substituted amino group include amino, methylamino, dimethylamino, ethylamino, diethylamino, ethylmethylamino, benzylamino, acetylamino, benzoylamino, methyloxycarbonylamino, and methanesulfonylamino.

Amino, methylamino, dimethylamino, ethylmethylamino, diethylamino, acetylamino, and methanesulfonylamino are preferred.

The term "optionally substituted carbamoyl" includes an aminocarbonyl group wherein the part of optionally substituted amino is "optionally substituted amino" as described herein. Examples of the optionally substituted carbamoyl group includes carbamoyl, N-methylcarbamoyl, N,N-dimethylcarbamoyl, N-ethyl-N-methylcarbamoyl, N,N-diethylcarbamoyl, N-phenylcarbamoyl, N-benzylcarbamoyl, N-acetylcarbamoyl, and N-methylsulfonylcarbamoyl etc. Carbamoyl, N-methylcarbamoyl, N,N-dimethylcarbamoyl, and N-methylsulfonylcarbamoyl etc. are preferred.

The term "optionally substituted sulfamoyl" includes an aminosulfonyl group wherein the part of optionally substituted amino is "optionally substituted amino" as described herein. Examples of the optionally substituted sulfamoyl group include sulfamoyl, N-methylsulfamoyl, N,N-dimethylsulfamoyl, N-ethyl-N-methyl sulfamoyl, N,N-diethylsulfamoyl, N-phenylsulfamoyl, N-benzylsulfamoyl, N-acetylsulfamoyl, and N-methylsulfonylsulfamoyl etc. Sulfamoyl, N-methylsulfamoyl, N,N-dimethylsulfamoyl, and N-methylsulfonylsulfamoyl etc. are preferred.

The term "alkylene" means a straight or branched alkylene group having one to eight carbon atom(s). Examples include methylene, ethylene, 1-methylethylene, trimethylene, 1-methyltrimethylene, pentamethylene, hexamethylene, and the like. C1-C4 or C1-3 alkylenes are preferred. C1-C2 alkylene is further preferred.

The term "aryl" includes an aromatic monocyclic or aromatic fused cyclic hydrocarbons. It may be fused with "cycloalkyl" as described herein, "cycloalkenyl" as described herein or "non-aromatic heterocyclic group" as described herein at any possible position. Both of monocyclic ring and fused ring may be substituted at any position. Examples include phenyl, 1-naphthyl, 2-naphthyl, anthryl, tetrahydronaphthyl, 1,3-benzodioxolyl, 1,4-benzodioxanyl etc. Phenyl, 1-naphthyl, and 2-naphthyl are preferred. Phenyl is further preferred.

The term "non-aromatic heterocyclic group" includes a 5- to 7-membered non-aromatic heterocyclic ring containing one or more of heteroatom(s) selected independently from oxygen, sulfur, and nitrogen atoms or a multicyclic ring formed by fusing the two or more rings thereof. Examples include pyrrolidinyl (e.g., 1-pyrrolidinyl, 2-pyrrolidinyl), pyrrolinyl (e.g., 3-pyrrolinyl), imidazolidinyl (e.g., 2-imidazolidinyl), imidazolinyl (e.g., imidazolinyl), pyrazolidinyl (e.g., 1-pyrazolidinyl, 2-pyrazolidinyl), pyrazolyl (e.g., pyrazolinyl), piperidyl (e.g., piperidino, 2-piperidyl), piperazinyl (e.g., 1-piperazinyl), indolinyl (e.g., 1-indolinyl), isoindolinyl (e.g., isoindolinyl), morpholinyl (e.g., morpholino, 3-morpholinyl) etc.

The term "heteroaryl" includes a 5- to 6-membered aromatic ring containing one or more of heteroatom(s) selected independently from oxygen, sulfur, and nitrogen atoms. It may be fused with "cycloalkyl" as described herein, "aryl" as described herein, "non-aromatic heterocyclic group" as described herein, or other heteroaryl at any possible position. The heteroaryl group may be substituted at any position whenever it is a monocyclic ring or a fused ring. Examples include pyrrolyl (e.g., 1-pyrrolyl, 2-pyrrolyl, 3-pyrrolyl), furyl (e.g., 2-furyl, 3-furyl), thienyl (e.g., 2-thienyl, 3-thienyl), imidazolyl (e.g., 2-imidazolyl, 4-imidazolyl), pyrazolyl (e.g., 1-pyrazolyl, 3-pyrazolyl), isothiazolyl (e.g., 3-isothiazolyl), isoxazolyl (e.g., 3-isoxazolyl), oxazolyl (e.g., 2-oxazolyl), thiazolyl (e.g., 2-thiazolyl), pyridyl (e.g., 2-pyridyl, 3-pyridyl, 4-pyridyl), pyrazinyl (e.g., 2-pyrazinyl), pyrimidinyl (e.g., 2-pyrimidinyl, 4-pyrimidinyl), pyridazinyl (e.g., 3-pyridazinyl), tetrazolyl (e.g., 1H-tetrazolyl), oxadiazolyl (e.g., 1,3,4-oxadiazolyl), thiadiazolyl (e.g., 1,3,4-thiadiazolyl), indolidinyl (e.g., 2-indolidinyl, 6-indolidinyl), isoindolynyl (e.g., 2-isoindolynyl), indolyl (e.g., 1-indolyl, 2-indolyl, 3-indolyl), indazolyl (e.g., 3-indazolyl), purinyl (e.g., 8-purinyl), quinolidinyl (e.g., 2-quinolidinyl), isoquinolyl (e.g., 3-isoquinolyl), quinolyl (e.g., 2-quinolyl, 5-quinolyl), phtharazinyl (e.g., 1-phtharazinyl), naphthylidinyl (e.g., 2-naphthylidinyl), quinolanyl (e.g., 2-quinolanyl), quinazolinyl (e.g., 2-quinazolinyl), cinnolinyl (e.g., 3-cinnolinyl), pteridinyl (e.g., 2-pteridinyl), carbazolyl (e.g., 2-carbazolyl, 4-carbazolyl), phenanthridinyl (e.g., 2-phenanthridinyl, 3-phenanthridinyl), acridinyl (e.g., 1-acridinyl, 2-acridinyl), dibenzofuranyl (e.g., 1-dibenzofuranyl, 2-dibenzofuranyl), benzoimidazolyl (e.g., 2-benzoimidazolyl), benzoisoxazolyl (e.g., 3-benzoisoxazolyl), benzooxazolyl (e.g., 2-benzooxazolyl), benzooxadiazolyl (e.g., 4-benzooxadiazolyl), benzoisothiazolyl (e.g., 3-benzoisothiazolyl), benzothiazolyl (e.g., 2-benzothiazolyl), benzofuryl (e.g., 3-benzofuryl), benzothienyl (e.g., 2-benzothienyl), dibenzothienyl (e.g., 2-dibenzothienyl), and benzodioxolyl (e.g., 1,3-benzodioxolyl), etc.

The term "aryloxy" includes a group in which an oxygen atom is substituted with one "aryl" as described herein. Examples include phenyloxy and naphthyloxy, etc.

The term "arylthio" includes a group in which a sulfur atom is substituted with one "aryl" as described herein. Examples include phenylthio and naphthylthio, etc.

The term "arylsulfinyl" includes a group in which sulfinyl is substituted with one "aryl" as described herein. Examples include phenylsulfinyl and naphthylsulfinyl, etc.

The term "arylsulfonyl" includes a group in which sulfonyl is substituted with one "aryl" as described herein. Examples include phenylsulfonyl and naphthylsulfoinyl, etc.

Examples of "arylsulfonyloxy" include phenylsulfonyloxy and naphthylsulfonyloxy, etc.

The term "aryloxycarbonyl" includes a group in which carbonyl is substituted with one "aryloxy" as described herein. Examples include phenyloxycarbonyl, 1-naphthyloxycarbonyl and 2-naphthyloxycarbonyl, etc.

The term "heteroaryloxy" includes a group in which an oxygen atom is substituted with one "heteroaryl" as described herein. Examples include pyrrolyloxy, furyloxy, thienyloxy, imidazolyloxy, pyrazolyloxy, isothiazolyloxy, isoxazolyloxy, oxazolyloxy, thiazolyloxy, pyridyloxy, pyrazinyloxy, pyrimidinyloxy, pyridazinyloxy, tetrazolyloxy, oxadiazolyloxy, thiadiazolyloxy, indolidinyloxy, isoindolynyloxy, indolyloxy, indazolyloxy, purinyloxy, quinolidinyloxy, isoquinolyloxy, quinolyloxy, phtharazinyloxy, naphthylidinyloxy, quinolanyloxy, quinazolinyloxy, cinnolinyloxy, pteridinyloxy, carbazolyloxy, phenanthridinyloxy, acridinyloxy, dibenzofuranyloxy, benzoimidazolyloxy, benzoisoxazolyloxy, benzooxazolyloxy, benzooxadiazolyloxy, benzoisothiazolyloxy, benzothiazolyloxy, benzofuryloxy, benzothienyloxy, dibenzothienyloxy, and benzodioxolyloxy are exemplified. Preferably furyloxy, thienyloxy, imidazolyloxy, pyrazolyloxy, isothiazolyloxy, isoxazolyloxy, oxazolyloxy, thiazolyloxy, pyridyloxy, pyrazinyloxy, pyrimidinyloxy, and pyridazinyloxy, etc.

The term "heteroarylthio" includes a group in which a sulfur atom is substituted with one "heteroaryl" as described herein. Examples include pyrrolylthio, furylthio, thienylthio, imidazolylthio, pyrazolylthio, isothiazolylthio, isoxazolylthio, oxazolylthio, thiazolylthio, pyridylthio, pyrazinylthio, pyrimidinylthio, pyridazinylthio, tetrazolylthio, oxadiazolylthio, thiadiazolylthio, indolidinylthio, isoindolynylthio, indolylthio, indazolylthio, purinylthio, quinolidinylthio, isoquinolylthio, quinolylthio, phtharazinylthio, naphthylidinylthio, quinolanylthio, quinazolinylthio, cinnolinylthio, pteridinylthio, carbazolylthio, phenanthridinylthio, acridinylthio, dibenzofuranylthio, benzoimidazolylthio, benzoisoxazolylthio, benzooxazolylthio, benzooxadiazolylthio, benzoisothiazolylthio, benzothiazolylthio, benzofurylthio, benzothienylthio, dibenzothienylthio, and benzodioxolylthio etc. are exemplified. Preferably furylthio, thienylthio, imidazolylthio, pyrazolylthio, isothiazolylthio, isoxazolylthio, oxazolylthio, thiazolylthio, pyridylthio, pyrazinylthio, pyrimidinylthio, and pyridazinylthio, etc.

The term "heteroarylsulfinyl" includes a group in which sulfinyl is substituted with one "heteroaryl" as described herein. Examples include pyrrolylsulfinyl, furylsulfinyl, thienylsulfinyl, imidazolylsulfinyl, pyrazolylsulfinyl, isothiazolylsulfinyl, isoxazolylsulfinyl, oxazolylsulfinyl, thiazolylsulfinyl, pyridylsulfinyl, pyrazinylsulfinyl, pyrimidinylsulfinyl, pyridazinylsulfinyl, tetrazolylsulfinyl, oxadiazolylsulfinyl, thiadiazolylsulfinyl, indolidinylsulfinyl, isoindolylsulfinyl, indolylsulfinyl, indazolylsulfinyl, purinylsulfinyl, quinolidinylsulfinyl, isoquinolylsulfinyl, quinolylsulfinyl, phtharazinylsulfinyl, naphthylidinylsulfinyl, quinolanylsulfinyl, quinazolinylsulfinyl, cinnolinylsulfinyl, pteridinylsulfinyl, carbazolylsulfinyl, phenanthridinylsulfinyl, acridinylsulfinyl, dibenzofuranylsulfinyl, benzoimidazolylsulfinyl, benzoisoxazolylsulfinyl, benzooxazolylsulfinyl, benzooxadiazolylsulfinyl, benzoisothiazolylsulfinyl, benzothiazolylsulfinyl, benzofurylsulfinyl, benzothienylsulfinyl, dibenzothienylsulfinyl, and benzodioxolylsulfinyl etc. are exemplified. Preferably furylsulfinyl, thienylsulfinyl, imidazolylsulfinyl, pyrazolylsulfinyl, isothiazolylsulfinyl, isoxazolylsulfinyl, oxazolylsulfinyl, thiazolylsulfinyl, pyridylsulfinyl, pyrazinylsulfinyl, pyrimidinylsulfinyl, and pyridazinylsulfinyl, etc.

The term "heteroarylsulfonyl" includes a group in which sulfonyl is substituted with one "heteroaryl" as described herein. Examples include pyrrolylsulfonyl, furylsulfonyl, thienylsulfonyl, imidazolylsulfonyl, pyrazolylsulfonyl, isothiazolylsulfonyl, isoxazolylsulfonyl, oxazolylsulfonyl, thiazolylsulfonyl, pyridylsulfonyl, pyrazinylsulfonyl, pyrimidinylsulfonyl, pyridazinylsulfonyl, tetrazolylsulfonyl, oxadiazolylsulfonyl, thiadiazolylsulfonyl, indolizinylsulfonyl, isoindolylsulfonyl, indolylsulfonyl, indazolylsulfonyl, purinylsulfonyl, quinolidinylsulfonyl, isoquinolylsulfonyl, quinolylsulfonyl, phtharazinylsulfonyl, naphthilidinylsulfonyl, quinolanylsulfonyl, quinazolinylsulfonyl, cinnolinyl sulfonyl, pteridinyl sulfonyl, carbazolylsulfonyl, phenanthridinylsulfonyl, acridinylsulfonyl, dibenzofuranylsulfonyl, benzoimidazolylsulfonyl, benzoisoxazolylsulfonyl, benzooxazolylsulfonyl, benzooxadiazolylsulfonyl, benzoisothiazolylsulfonyl, benzothiazolylsulfonyl, benzofurylsulfonyl, benzothienylsulfonyl, dibenzothienylsulfonyl, and benzodioxolylsulfonyl, etc. Furylsulfonyl, thienylsulfonyl, imidazolylsulfonyl, pyrazolylsulfonyl, isothiazolylsulfonyl, isoxazolylsulfonyl, oxazolylsulfonyl, thiazolylsulfonyl, pyridylsulfonyl, pyrazinylsulfonyl, pyrimidinylsulfonyl, and pyridazinylsulfonyl are preferred.

The term "heteroarylsulfonyloxy" includes a group in which an oxygen atom is substituted with one "heteroarylsulfonyl" as described herein. Examples include pyrrolylsulfonyloxy, furylsulfonyloxy, thienylsulfonyloxy, imidazolylsulfonyloxy, pyrazolylsulfonyloxy, isothiazolylsulfonyloxy, isoxazolylsulfonyloxy, oxazolylsulfonyloxy, thiazolylsulfonyloxy, pyridylsulfonyloxy, pyrazinylsulfonyloxy, pyrimidinylsulfonyloxy, pyridazinylsulfonyloxy, tetrazolylsulfonyloxy, oxadiazolylsulfonyloxy, thiadiazolylsulfonyloxy, indolizinylsulfonyloxy, isoindolylsulfonyloxy, indolylsulfonyloxy, indazolylsulfonyloxy, purinylsulfonyloxy, quinolidinylsulfonyloxy, isoquinolylsulfonyloxy, quinolylsulfonyloxy, phtharazinylsulfonyloxy, naphthilidinylsulfonyloxy, quinolanyl sulfonyloxy, quinazolinylsulfonyloxy, cinnolinylsulfonyloxy, pteridinylsulfonyloxy, carbazolylsulfonyloxy, phenanthridinylsulfonyloxy, acridinylsulfonyloxy, dibenzofuranylsulfonyloxy, benzoimidazolylsulfonyloxy, benzoisoxazolylsulfonyloxy, benzooxazolylsulfonyloxy, benzooxadiazolylsulfonyloxy, benzoisothiazolylsulfonyloxy, benzothiazolylsulfonyloxy, benzofuryl sulfonyloxy, benzothienylsulfonyloxy, dibenzothienylsulfonyloxy, and benzodioxolylsulfonyloxy etc. are exemplified.

Preferably, furylsulfonyloxy, thienylsulfonyloxy, imidazolylsulfonyloxy, pyrazolylsulfonyloxy, isothiazolylsulfonyloxy, isoxazolylsulfonyloxy, oxazolylsulfonyloxy, thiazolylsulfonyloxy, pyridylsulfonyloxy, pyrazinylsulfonyloxy, pyrimidinylsulfonyloxy, and pyridazinylsulfonyloxy, etc.

The term "aromatic carbocyclic ring" includes an aromatic monocyclic or aromatic fused carbocyclic ring. Examples include a benzene ring, a naphthalene ring, and an anthracene ring. A benzene ring is preferred.

The term "aromatic heterocyclic ring" includes an aromatic monocyclic or aromatic fused heterocyclic ring. Examples include a pyrrole ring, a furan ring, a thiophen ring, a pyrazole ring, an imidazole ring, an isothiazole ring, an isoxazole ring, an oxazole ring, a thiazole ring, a pyrazine ring, a pyrimidine ring, a pyridazine ring, a tetrazole ring, an oxadiazole ring, a thiadiazole ring, an indolizine ring, an isoindole ring, an indole ring, an indazole ring, a purine ring, a quinolidine ring, an isoquinoline ring, a quinoline ring, a phtharazine ring, a naphthyridine ring, a quinolane ring, a quinazoline ring, a cinnoline ring, a pteridine ring, a carbazole ring, a phenanthridine ring, an acridine ring, a dibenzofuran ring, a benzoimidazole ring, a benzoisoxazole ring, a benzooxazole ring, a benzooxadiazole ring, a benzoisothiazole ring, a benzothiazole ring, a benzofuran ring, a benzothiophen ring, a dibenzothiophen ring, and a benzodixolane ring. A pyridine ring, a furan ring, and a thiophen ring are preferred.

The term "C1-C6 alkylene" includes a straight or branched alkylene group having one to six carbon atom(s). Examples include —$CH_2$—, —$CH(CH_3)$—, —$C(CH_3)_2$—, —$CH_2CH_2$—, —$CH(CH_3)CH_2$—, —$C(CH_3)_2CH_2$—, —$CH_2CH_2CH_2$—, —$CH_2CH_2CH_2CH_2$—, —$CH_2CH_2CH_2$ CH₂CH₂—, and —CH₂CH₂CH₂CH₂CH₂CH₂—. Preferred are —CH₂—, —CH₂CH₂—, —CH₂CH₂CH₂—, and —CH₂CH₂CH₂CH₂—.

The term "alkylene optionally containing one or two heteroatom(s)" of "optionally substituted alkylene optionally containing one or two heteroatom(s)" includes a straight or branched alkylene group having one to six carbon atoms, optionally containing one or two heteroatom(s) which may be substituted with "alkyl" as described herein. Examples include —CH₂—, —CH(CH₃)—, —C(CH₃)₂—, —CH₂CH₂—, —CH₂CH₂CH₂—, —CH₂CH₂CH₂CH₂—, —CH₂CH₂CH₂CH₂CH₂—, —CH₂CH₂CH₂CH₂CH₂CH₂—, —CH₂O—, —OCH₂—, —CH₂CH₂O—, —OCH₂CH₂—, —CH₂S—, —SCH₂—, —CH₂CH₂S—, —SCH₂CH₂—, —CH₂CH₂OCH₂CH₂—, —OCH₂CH₂O—, —OCH₂O—, —NHCH₂—, —N(CH₃)CH₂—, —N⁺(CH₃)₂CH₂—, —NHCH₂CH₂CH₂—, and N(CH₃)CH₂CH₂CH₂—, etc. Preferred are —CH₂—, —CH₂CH₂—, —CH₂CH₂CH₂—, —CH₂CH₂CH₂CH₂—, —OCH₂CH₂O—, —OCH₂O—, and —N(CH₃)CH₂CH₂CH₂—.

The term "alkenylene optionally containing one or two heteroatom(s)" of "optionally substituted alkenylene optionally containing one or two heteroatom(s)" includes a straight or branched alkenylene group having two to six carbon atoms, optionally containing one or two heteroatom(s) which may be substituted with "alkyl" as described herein. Examples include —CH=CHCH=CH—, —CH=CHO—, —OCH=CH—, —CH=CHS—, —SCH=CH—, —CH=CHNH—, —NHCH=CH—, —CH=CH—CH=N—, and —N=CH—CH=CH—. Preferred are, —CH=CHCH=CH—, —CH=CHCH=N—, and —N=CHCH=CH—.

The term "alkynylene optionally containing one or two heteroatom(s)" includes a straight or branched alkynylene group having two to six carbon atoms, optionally containing one or two heteroatom(s) which may be substituted with "alkyl" as described herein. Examples include —C≡CCH₂—, —CH₂C≡CCH₂—, —CH₂C≡CCH₂O—, —OCH₂C≡CH—, —CH₂C≡CCH₂S—, —SCH₂C≡CH—, —CH₂C≡CCH₂NH—, —NHCH₂C≡CH—, —CH₂C≡CCH₂N(CH₃)—, and —N(CH₃)CH₂C≡CH—. Especially, —CH₂C≡CCH₂—, and OCH₂C≡CH— are preferred.

The term "3- to 8-membered nitrogen-containing non-aromatic heterocyclic ring" includes a ring of any of the formulas described as such in U.S. Pat. No. 8,143,285, which is incorporated herein by reference in its entirety.

The term "3- to 8-nitrogen-containing aromatic heterocyclic ring" includes a 3- to 8-membered aromatic heterocyclic ring containing one or more of nitrogen atom(s), and further optionally an oxygen atom and/or sulfur atom in the ring. Examples include pyrrolyl (e.g., 1-pyrrolyl, 2-pyrrolyl, 3-pyrrolyl), imidazolyl (e.g., 2-imidazolyl, 4-imidazolyl), pyrazolyl (e.g., 1-pyrazolyl, 3-pyrazolyl), isothiazolyl (e.g., 3-isothiazolyl), isoxazolyl (e.g., 3-isoxazolyl), oxazolyl (e.g., 2-oxazolyl), thiazolyl (e.g., 2-thiazolyl), pyridyl (e.g., 2-pyridyl, 3-pyridyl, 4-pyridyl), pyrazinyl (e.g., 2-pyrazinyl), pyrimidinyl (e.g., 2-pyrimidinyl, 4-pyrimidinyl), pyridazinyl (e.g., 3-pyridazinyl), tetrazolyl (e.g., 1H-tetrazolyl), oxadiazolyl (e.g., 1,3,4-oxadiazolyl), and thiadiazolyl (e.g., 1,3,4-thiadiazolyl).

The term "4- to 8-membered nitrogen-containing heterocyclic ring containing one or two nitrogen atom(s)" means a ring of any of the formulas described as such in U.S. Pat. No. 8,143,285, which is incorporated herein by reference in its entirety.

"Optionally substituted" is used interchangeably herein with "substituted or unsubstituted."

In the present specification, examples of substituents in "optionally substituted alkyl," "optionally substituted alkyloxy," "optionally substituted alkylthio," "optionally substituted alkylsulfinyl," "optionally substituted alkylsulfonyl," "optionally substituted alkylsulfonyloxy," and "the optionally substituted alkyloxycarbonyl" include cycloalkyl, alkylene optionally containing one or two heteroatom(s), hydroxy, oxo, alkyloxy optionally substituted with a substituent group A at one to three position(s), mercapto, alkylthio, a halogen atom, nitro, cyano, carboxy, alkyloxycarbonyl, optionally substituted amino, optionally substituted carbamoyl, acyl, aryl (e.g., phenyl) optionally substituted with a substituent group B at one to three position(s), heteroaryl (e.g., pyridyl, furyl, thienyl, imidazolyl, oxazolyl, thiazolyl, pyrazolyl) optionally substituted with a substituent group C at one to three position(s), an optionally substituted non-aromatic heterocyclic ring group (e.g., morpholinyl, pyrrolidinyl, piperazinyl) which may be substituted with a substituent group C at one to three position(s), aryloxy (e.g., phenyloxy) optionally substituted with a substituent group B at one to three position(s), alkylsulfonyl, and the like. The above-referenced "optionally substituted" moieties can be substituted with one to three of the above-referenced substituent(s) at any possible position.

In the present specification, examples of substituents in "optionally substituted alkenyl," "optionally substituted alkynyl," "optionally substituted alkenyloxy," "optionally substituted alkynyloxy," "optionally substituted alkenylthio," "optionally substituted alkynylthio," "optionally substituted alkenyloxycarbonyl," "optionally substituted alkynyloxycarbonyl," "optionally substituted cycloalkyl," "optionally substituted cycloalkenyl," "optionally substituted cycloalkyloxy, "optionally substituted cycloalkenyloxy," "optionally substituted cycloalkylthio," "optionally substituted cycloalkenylthio," "optionally substituted cycloalkylsulfinyl," "optionally substituted cycloalkenylsulfinyl," "optionally substituted cycloalkylsulfonyl," "optionally substituted cycloalkenylsulfonyl," "optionally substituted cycloalkylsulfonyloxy," "optionally substituted cycloalkenylsulfonyloxy," "optionally substituted alkenyloxycarbonyl," "optionally substituted alkylene," "optionally substituted C1-C6 alkylene," "optionally substituted alkylene optionally containing one or two heteroatom(s)," "optionally substituted alkenylene," "optionally substituted alkenylene optionally containing one or two heteroatom(s)," "optionally substituted alkynylene," and "optionally substituted alkynylene optionally containing one or two heteroatom(s)" include alkyl (such as dialkyl) optionally substituted with a substituent group D at one to three position(s), cycloalkyl, hydroxy, oxo, alkyloxy optionally substituted with a substituent group A at one to three position(s), mercapto, alkylthio, a halogen atom, nitro, cyano, carboxy, alkyloxycarbonyl, optionally substituted amino, optionally substituted carbamoyl, acyl acyloxy, aryl (e.g., phenyl) optionally substituted with a substituent group B at one to three position(s), heteroaryl (e.g., pyridyl, furyl, thienyl, imidazolyl, oxazolyl, thiazolyl, pyrazolyl) optionally substituted with a substituent group C at one to three position(s), non-aromatic heterocyclic group (e.g., morpholinyl, pyrrolidinyl, piperazinyl) optionally substituted with a substituent group C at one to three position(s), aryloxy (e.g., phenyloxy) optionally substituted with a substituent group C at one to three position(s), alkylsulfonyl, and the like. The above-referenced "optionally substituted" moieties can be substituted with one or more of the above-referenced substituent(s) at any possible position.

In the present specification, examples of substituents in "optionally substituted aryl," "optionally substituted phenoxy," "optionally substituted aryloxy," "optionally substituted phenylthio," "optionally substituted arylthio," "optionally substituted arylsulfinyl," "optionally substituted arylsulfonyl," "optionally substituted arylsulfonyloxy," "optionally substituted heteroaryl," "optionally substituted heteroaryloxy," "optionally substituted heteroarylthio," "optionally substituted heteroarylsulfinyl," "optionally substituted heteroarylsulfonyl," "optionally substituted heteroarylsulfonyloxy," "optionally substituted non-aromatic heterocyclic group," "optionally substituted piperazine-1,4-diyl," "substituted piperazine-1,4-diyl," "optionally substituted C6 arene-1,4-diamine-$N^1,N^4$-diyl," and substituted C6 arene-1,4-diamine-$N^1,N^4$-diyl," include alkyl optionally substituted with a substituent group D at one to three position(s), oxo, cycloalkyl, alkenyl, alkynyl, hydroxy, alkyloxy optionally substituted with a substituent group A at one to three position(s), aryloxy (e.g., phenoxy) optionally substituted with a substituent group B at one to three position(s), mercapto, alkylthio, a halogen atom, nitro, cyano, carboxy, alkyloxycarbonyl, acyl, alkylsulfonyl, optionally substituted amino, optionally substituted carbamoyl, aryl (e.g., phenyl) optionally substituted with a substituent group B at one to three position(s), heteroaryl (e.g., pyridyl, furyl, thienyl, imidazolyl, oxazolyl, thiazolyl, pyrazolyl) optionally substituted with a substituent group C at one to three position(s), non-aromatic heterocyclic group (e.g., morpholinyl, pyrrolidinyl, piperazinyl) optionally substituted with a substituent group C at one to three position(s), and the like. The above-referenced "optionally substituted" moieties can be substituted with one or more of the above-referenced substituent(s) at any possible position.

Substituent group A is comprised of a halogen atom and phenyl optionally substituted with one to three substituent(s) selected from the Substituent group B.

Substituent group B is comprised of a halogen atom, alkyl, alkyloxy, cyano, and nitro.

Substituent group C is comprised of a halogen atom and alkyl.

Substituent group D is comprised of a halogen atom and alkyloxy.

In compounds in which $R^2$ is an electron pair, the oxygen is negatively charged and may form a salt with a cation.

In some compounds, the $R^3$ on at least 1, at least 2, at least 3 of $A^1$, $A^2$, $A^3$, $A^4$, and $A^5$ is a hydrogen atom or C1-C6 alkyl.

In the course of the methods of the present invention, a therapeutically effective amount of compounds of the invention can be administered to an animal, including mammals and humans, in many ways. While in the preferred embodiment, the compounds of the invention are administered orally, parenterally, or topically, other forms of administration such as through medical compounds or aerosols are also contemplated.

For oral administration, the effective amount of compounds may be administered in, for example, a solid, semi-solid, liquid, or gas state. Specific examples include tablet, capsule, powder, granule, solution, suspension, syrup, and elixir agents. However, the compounds are not limited to these forms.

To formulate the compounds of the invention into tablets, capsules, powders, granules, solutions, or suspensions, the compound is preferably mixed with a binder, a disintegrating agent and/or a lubricant. If necessary, the resultant composition may be mixed with a diluent, a buffer, an infiltrating agent, a preservative and/or a flavor, using known methods. Examples of the binder include crystalline cellulose, cellulose derivatives, cornstarch, cyclodextrins, and gelatin. Examples of the disintegrating agent include cornstarch, potato starch, and sodium carboxymethylcellulose. Examples of the lubricant include talc and magnesium stearate. Further, additives, which have been conventionally used, such as lactose and mannitol, may also be used.

For parenteral administration, the compounds of the present invention may be administered rectally or by injection. For rectal administration, a suppository may be used.

The suppository may be prepared by mixing the compounds of the present invention with a pharmaceutically suitable excipient that melts at body temperature but remains solid at room temperature. Examples include but are not limited to cacao butter, carbon wax, and polyethylene glycol. The resulting composition may be molded into any desired form using methods known to the field.

For administration by injection, the compounds of the present invention may be injected hypodermically, intracutaneously, intravenously, or intramuscularly. Medicinal drugs for such injection may be prepared by dissolving, suspending or emulsifying the compounds of the invention into an aqueous or non-aqueous solvent such as vegetable oil, glyceride of synthetic resin acid, ester of higher fatty acid, or propylene glycol by a known method. If desired, additives such as a solubilizing agent, an osmoregulating agent, an emulsifier, a stabilizer, or a preservative, which has been conventionally used may also be added. While not required, it is preferred that the composition be sterile or sterilized.

To formulate the compounds of the invention into suspensions, syrups, or elixirs, a pharmaceutically suitable solvent may be used. Included among these is the non-limiting example of water.

For topical administration, topical formulations can be in a form of gel, cream, lotion, liquid, emulsion, ointment, spray, solution, suspension, and patches. Inactive ingredients in the topical formulations for example include, but not limited to, lauryl lactate (emollient/permeation enhancer), diethylene glycol monoethylether (emollient/permeation enhancer), DMSO (solubility enhancer), silicone elastomer (rheology/texture modifier), caprylic/capric triglyceride, (emollient), octisalate, (emollient/UV filter), silicone fluid (emollient/diluent), squalene (emollient), sunflower oil (emollient), and silicone dioxide (thickening agent).

The compounds of the invention may also be used together with an additional compound having other pharmaceutically suitable activity to prepare a medicinal drug. A drug, either containing a compound of the invention as a stand-alone compound or as part of a composition, may be used in the treatment of subjects in need thereof.

The compounds of the invention may also be administered in the form of an aerosol or inhalant prepared by charging the compounds in the form of a liquid or fine powder, together with a gaseous or liquid spraying agent and, if necessary, a known auxiliary agent such as an inflating agent, into a non-pressurized container such as an aerosol container or a nebulizer. A pressurized gas of, for example, dichlorofluoromethane, propane or nitrogen may be used as the spraying agent.

The compounds of the invention may be administered to an animal, including mammals and humans, in need thereof as a pharmaceutical composition, such as tablets, capsules, solutions, or emulsions. Administration of other forms of the compounds described in this invention, including but not limited to esters thereof, pharmaceutically suitable salts thereof, metabolites thereof, structurally related compounds thereof, analogs thereof, and combinations thereof, in a single dose or a multiple dose, are also contemplated by the present invention.

The compounds of the invention may also be administered to an animal in need thereof as a nutritional additive, either as a food or nutraceutical supplement.

The terms "preventing," "treating," or "ameliorating" and similar terms used herein, include prophylaxis and full or partial treatment. The terms may also include reducing symptoms, ameliorating symptoms, reducing the severity of symptoms, reducing the incidence of the disease, or any other change in the condition of the patient, which improves the therapeutic outcome.

The compounds described in this invention are preferably used and/or administered in the form of a composition. Suitable compositions are, preferably, a pharmaceutical composition, a foodstuff, or a food supplement. These compositions provide a convenient form in which to deliver the compounds. Compositions of the invention may comprise an antioxidant in an amount effective to increase the stability of the compounds with respect to oxidation or solubility.

The amount of compound that is administered in the method of the invention or that is for administration in the use of the invention is any suitable amount. It is preferably from 1 ng/kg body weight to 20 g/kg body weight, more preferably in the range of 1 µg/kg body weight to 1 g/kg body weight, such as 1 mg/kg body weight to 100 mg/kg body weight of compound per day. Suitable compositions can be formulated accordingly. Those of skill in the art of dosing of biologically active agents will be able to develop particular dosing regimens for various subjects based on known and well understood parameters.

A preferred composition according to the invention is a pharmaceutical composition, such as in the form of tablets, pills, capsules, caplets, multiparticulates (including granules, beads, pellets and micro-encapsulated particles), powders, elixirs, syrups, suspensions, and solutions. Pharmaceutical compositions will typically comprise a pharmaceutically acceptable diluent or carrier. Pharmaceutical compositions are preferably adapted for administration parenterally or orally. Orally administrable compositions may be in solid or liquid form and may take the form of tablets, powders, suspensions, and syrups, among other things. Optionally, the compositions comprise one or more flavoring and/or coloring agents. In general, therapeutic and nutritional compositions may comprise any substance that does not significantly interfere with the action of the compounds on the subject.

Pharmaceutically acceptable carriers suitable for use in such compositions are well known in the art of pharmacy. The compositions of the invention may contain 0.01-99% by weight of the compounds of the invention. The compositions of the invention are generally prepared in unit dosage form. Preferably the unit dosage of compounds described in the present invention is from 0.1 mg to 2000 mg, more preferably from 50 mg to 1000 mg. The excipients used in the preparation of these compositions are the excipients known in the art.

Further examples of product forms for the composition are food supplements, such as in the form of a soft gel or a hard capsule comprising an encapsulating material selected from the group consisting of gelatin, starch, modified starch, starch derivatives such as glucose, sucrose, lactose, and fructose. The encapsulating material may optionally contain cross-linking or polymerizing agents, stabilizers, antioxidants, light absorbing agents for protecting light-sensitive fills, preservatives, and the like. Preferably the unit dosage of compounds described in the present invention is from 0.1 mg to 2000 mg, more preferably from 50 mg to 1000 mg.

In general, the term carrier may be used throughout this application to represent a composition with which the compounds described may be mixed, be it a pharmaceutical carrier, foodstuff, nutritional supplement, or dietary aid. The materials described above may be considered carriers for the purposes of the invention. In certain embodiments of the invention, the carrier has little to no biological activity on the compounds of the invention.

Dose: The methods of the present invention can comprise administering a therapeutically effective amount of compound to an animal in need thereof. The effective amount of compound depends on the form of the compound administered, the duration of the administration, the route of administration (e.g., oral or parenteral), the age of the animal, and the condition of the animal, including mammals and humans.

For instance, an amount of a compound effective to treat or prevent type 1 diabetes, lupus, ulcerative colitis, Crohn's disease, gastrointestinal inflammation, or any other condition described herein in an animal can range from 1 ng/kg/day to 20 g/kg/day.

A preferred effective amount of compound is 50 µg/kg/day to 5 g/kg/day, with a more preferred dose being 1 to 100 mg/kg/day. The effective amount of compound is most effective in treating or preventing type 1 diabetes, lupus, ulcerative colitis, Crohn's disease, gastrointestinal inflammation, or any other condition described herein of an animal when administered to an animal for periods ranging from about 1 to 1000 days, with a preferred period of 7 to 300 days, and a most preferred period of 30 to 90 days, whereby most effective is defined as an identification of the induction of beneficial responses. The effective amount of compound may be continued beyond these periods for maintenance of beneficial responses in chronic diseases.

An amount of compound most effective in preventing over-activation of the immune system can range from 1 ng/kg/day to 20 g/kg/day, with a preferred dose of 1 to 100 mg/kg/day.

When the effective amount of the compound of the present invention is administered in a nutritional, therapeutic, medical, or veterinary composition, the preferred dose ranges from about 0.01 to 2.0% wt/wt to the food or nutraceutical product.

In certain other embodiments, the present invention provides for use of the compounds described herein in the treatment and prevention of type 1 diabetes, lupus, IBD and GI tract inflammation.

In addition, in general, the present invention relates to inhibition or activation of inflammation systemically, wherein the relevant components include the pancreas, spleen, lung, heart, central nervous system, joints, liver, kidneys, or in the GI tract, wherein the relevant components include the esophagus, stomach, small intestine, cecum, large intestine, and rectum. The effect results from the exposure of compound to various cells types in the body that induces a biological effect. The cells may include those from GI tract tissues, immune cells (i.e. macrophages, monocytes, lymphocytes), pancreatic islet cells, endothelial cells, neurons, or epithelial cells. In certain embodiments, the invention provides for treating subjects with a compound of the invention, for example as a dietary supplement, to reduce or prevent inflammation related to type 1 diabetes, lupus or inflammatory bowel disease, either Crohn's disease or ulcerative colitis.

When practiced, the methods of the invention can be by way of administering the compounds to a subject via any acceptable administration route using any acceptable form, as is described above, and allowing the body of the subject to distribute the compounds to the target cell through natural processes. As is described above, administering can likewise be by direct injection to a site (e.g., organ, tissue) containing a target cell (i.e., a cell to be treated).

Furthermore, administering can follow any number of regimens. It thus can comprise a single dose or dosing of experimental compound, or multiple doses or dosings over a period of time. Accordingly, treatment can comprise repeating the administering step one or more times until a desired result is achieved. In certain embodiments, treating can continue for extended periods of time, such as weeks, months, or years. Dosing regimens can preferably entail administration of compound between 6 times daily to once per week, with a more preferred regimen between three times daily to once daily. Those of skill in the art are fully capable of easily developing suitable dosing regimens for individuals based on known parameters in the art. The dosage amounts for compounds of the invention may be used in the methods of these embodiments of the invention. For the treatment of type 1 diabetes, lupus or IBD, it is preferred that the compounds be administered at amounts of about 10 ng/day to 10 g/day.

The amount to be administered will vary depending on the subject, stage of disease or disorder, age of the subject, general health of the subject, and various other parameters known and routinely taken into consideration by those of skill in the medical arts. As a general matter, a sufficient amount of compound will be administered in order to make a detectable change in the amount of inflammation in the pancreas, GI tract or systemically.

Reduction of inflammation may be related to amount of pain experienced by the subject, insulin, anti-nuclear antigen antibodies, TNFα or C-reactive protein levels in the blood, the percent of regulatory T-cells in the blood or concentration of calprotectin in feces. Suitable amounts are disclosed herein, and additional suitable amounts can be identified by those of skill in the art without undue or excessive experimentation, based on the amounts disclosed herein.

It should be evident that the present invention provides LANCL2-binding compound therapy for use in contacting cells, such as in treating cells of a subject. The above discussion focuses on the use of the compounds of the present invention as part of a composition for use in what could generally be considered a pharmaceutical or medical setting.

The compounds described in this invention for the treatment of autoimmune disease including type 1 diabetes, systemic lupus erythematosus, IBD, Sjögren's syndrome, and other conditions described herein may be formulated as a pharmaceutical, nutritional composition, functional food composition, or dietary aid, as are described in greater detail above.

As an alternative or in addition to the methods of treating conditions by administering the compounds directly, the conditions can be treated with prepared cells generated from precursor cells with the compounds.

The term "precursor cell" is used herein to refer generally to any cell that serves as a starting cell that is treated to generate a prepared cell. The cell may be a cell upstream in a differentiation lineage leading to the prepared cell, such as a stem cell, a progenitor cell, or a "precursor cell" (as the term is used in the art to refer to an intermediate between a stem cell and a differentiated cell) with, e.g., totipotent, multipotent or unipotent properties, but does not necessarily have to be so. Accordingly, in some versions, generating the prepared cell from the precursor cell involves differentiating the precursor cell into the prepared cell. In other versions, generating the prepared cell from the precursor cell merely involves inducing changes such as gene expression changes.

The prepared cells can be generated from precursor cells by contacting the precursor cells in vitro with one or more of the compounds of the invention to thereby generate the prepared cells. The terms "in vitro" and "ex vivo" are used interchangeably herein in contrast to "in vivo" and refer to a state of being outside of a living organism.

The precursor and/or prepared cells of the invention may comprise immune cells. Exemplary immune cells include granulocytes, mast cells, monocytes, macrophages, neutrophils, dendritic cells, natural killer cells, T cells, and B cells, among others. Exemplary granulocytes include basophils, eosinophils, and neutrophils.

The precursor and/or prepared cells of the invention may comprise white blood cells (leukocytes). Exemplary white blood cells include neutrophils, eosinophils (acidophiles), basophils, lymphocytes, and monocytes.

The precursor and/or prepared cells of the invention may comprise peripheral blood mononuclear cells (PBMCs) or lamina propria mononuclear cells (LPMCs). Exemplary PBMCs and LPMCs include lymphocytes (T cells, B cells, NK cells) and monocytes.

The precursor and/or prepared cells of the invention may comprise T cells. T cells are divided into two broad categories: CD8+ T cells or CD4+ T cells, based on which protein is present on the cell's surface. T cells carry out multiple functions, including killing infected cells and activating or recruiting other immune cells. CD8+ T cells also are called cytotoxic T cells or cytotoxic lymphocytes (CTLs). They are crucial for recognizing and removing virus-infected cells and cancer cells. The major CD4+ T-cell subsets are naïve CD4+ T cells, TH1 cells, TH2 cells, TH17 cells, and Treg cells, with "TH" referring to "T helper cell." Naïve CD4+ T cells are T cells that are not differentiated into any of TH1 cells, TH2 cells, TH17 cells, and Treg cells. Regulatory T cells (Tregs) monitor and inhibit the activity of other T cells. They prevent adverse immune activation and maintain tolerance, or the prevention of immune responses against the body's own cells and antigens. In some versions, the precursor cells comprise naïve CD4+ T cells, and the prepared cells comprise Treg cells.

Generating the prepared cells from the precursor cells may comprise contacting an amount of one or more compounds of the invention for a time effective to induce a compound-dependent difference in the prepared cells with respect to the precursor cells. As used herein, "compound-dependent difference" refers to a difference in the prepared cell with respect to the precursor cell arising from contacting the precursor cell with one or more compounds of the invention. Compound-dependent differences can be determined by contacting cells with media in the presence or absence the one or more compounds of the invention, wherein the compound-dependent differences are characteristics that appear only with the cells contacted with media in the presence of the one or more compounds of the invention. The compound-dependent differences may be differences not only in kind but also of degree.

The compound-dependent difference in the prepared cells may include a difference in gene expression. Unless explicitly stated otherwise, "gene expression" is used broadly herein to refer to any or all of transcription or translation. Thus, a difference in gene expression can be a difference in mRNA production, a difference in protein production, or both. Unless explicitly stated otherwise, the gene having differential expression may be identified herein by referring to the protein produced from the gene (e.g., FOXP3) or by referring to the gene itself (e.g., Lag3). In various versions of the invention, the compound-dependent differences in gene expression may comprise one or more of an increase in expression of IL-10 or an ortholog thereof, an increase in expression of FOXP3 or an ortholog thereof, a decrease in expression of TNFα or an ortholog thereof, a decrease in expression of IFNγ or an ortholog thereof, a decrease in expression of Tbet or an ortholog thereof, an increase in expression of Lag3 or an ortholog thereof, an increase in expression of Socs2 or an ortholog thereof, an increase in expression of Irf7 or an ortholog thereof, an increase in expression of P2rx7 or an ortholog thereof, an increase in expression of Capn3 or an ortholog thereof, an increase in expression of Ikzf2 or an ortholog thereof, an increase in expression of Stat5a or an ortholog thereof, an increase in expression of Pten or an ortholog thereof, an increase in expression of Foxo1 or an ortholog thereof, and/or an increase in expression of Phlpp1 or an ortholog thereof. The orthologs may include orthologs in animal species. The orthologs may include orthologs in mammalian species. The orthologs (such as for the mouse genes named above) may include orthologs in primates. The orthologs (such as for the mouse genes named above) may include orthologs in humans.

The compound-dependent difference in the prepared cells may include other detectable differences, such as an increase in phosphorylation of STAT5a or an ortholog thereof, an increase in FOXO1 phosphorylation or an ortholog thereof, and/or an increase in pyruvate kinase activity.

In generating the prepared cells, the precursor cells may be contacted with amounts of the compound from about 100 nM, about 10 nM, about 1 nM or less to about 1 μM, about 10 μM, about 100 μM, about 1 mM or more. The precursor cells may be contacted with the compound for a time from about 12 hours, 6 hours, 1 hour, about 30 minutes, or less to about 24 hours, about 48 hours, about 72 hours or more.

In some versions, the PBMCs or LPMCs at large are contacted with the compound of the invention. The PBMCs or LPMCs can be isolated from an animal. In some versions, subtypes of PBMCs or LPMCs, such as T cells, can be isolated from the PBMCs or LPMCs and then contacted with the compound of the invention. In some versions, the PBMCs or LPMCs are contacted with the compound of the invention, and then subtypes of cells, such as T cells or a particular type of T cells are isolated therefrom. Methods for isolating PBMCs, LPMCs, and subtypes thereof are known in the art. See, e.g., Majowicz et al. 2012 (Majowicz A, van der Marel S, te Velde A A, Meijer S L, Petry H, van Deventer S J, Ferreira V. Murine CD4+ CD25- cells activated in vitro with PMA/ionomycin and anti-CD3 acquire regulatory function and ameliorate experimental colitis in vivo. BMC Gastroenterol. 2012 Dec. 3; 12:172) and Canavan et al. 20016 (Canavan J B, Scotti C, Vossenkamper A, Goldberg R, Elder M J, Shoval I, Marks E, Stolarczyk E, Lo J W, Powell N, Fazekasova H, Irving P M, Sanderson J D, Howard J K, Yagel S, Afzali B, MacDonald T T, Hernandez-Fuentes M P, Shpigel N Y, Lombardi G, Lord G M. Developing in vitro expanded CD45RA+ regulatory T cells as an adoptive cell therapy for Crohn's disease. *Gut*. 2016 April; 65(4):584-94). Subsets of PMBCs, for example, can be isolated with anti-CD3 antibodies and anti-CD28 antibodies. Anti-CD3 antibodies and anti-CD28 antibodies can be provided in the form of anti-CD3/anti-CD28 beads, such as Human T-Activator CD3/CD28 DYNABEADS® from ThermoFisher Scientific (Waltham, Mass.).

Generating the prepared cells can comprise differentiating the prepared cells from the precursor cells. For example, prepared cells such as Treg cells can be differentiated from precursor cells such as naïve CD4+ T cells. Such differentiating can comprise contacting the precursor cells with differentiating factors in addition to one or more of the compounds of the invention. Various differentiating factors may include all-trans-retinoic acid, TGF-β, phorbol myristate acetate, ionomycin, rapamycin, and/or IL-2. In some versions, the differentiating can comprise expanding the proportion of Treg cells in the prepared cells with respect to the portion in the precursor cells.

The precursor and prepared cells of the invention can be isolated cells. The term "isolated" or "purified" means a material that is removed from its original environment, for example, the natural environment. A material is said to be "purified" when it is present in a particular composition in a higher or lower concentration than the concentration that exists prior to the purification step(s).

Treating the condition with the prepared cells of the invention can comprise administering the cells to the animal in an amount sufficient to treat the condition. The prepared cells can be administered using any route or method described above for the compounds, including parenterally or enterally. Non-limiting forms of parenteral administration include injection or infusion. The prepared cells can be injected or infused directly into the bloodstream or other parts of the body. Non-limiting forms of enteral administration include oral and rectal administration, such that the prepared cells enter the gastrointestinal tract. The prepared cells may be autologous to the treated animal (i.e., generated from a cell taken from the same animal that the prepared cell is used to treat) or heterologous to the treated animal (i.e., generated from a different animal that the prepared cell is used to treat). A cell prepared as described above can be used in a method of treating any of the conditions described herein. Exemplary conditions include intestinal inflammation. Exemplary types of intestinal inflammation include inflammatory bowel disease. Exemplary types of inflammatory bowel disease include Crohn's disease and ulcerative colitis.

In one embodiment of the invention, the method of treating immunometabolic disease comprises treatment without causing discernable side-effects, such as significant weight gain, systemic immune suppression, cushingoid appearance, osteopenia/osteoporosis, cellular toxicity or pancreatitis that is common of currently available treatments (i.e. statins, antibiotics, corticosteroids, doxorubicin, methotrexate). That is, it has been found that the method of treating according to the present invention, which provides the treatment effect, at least in part, by affecting the expression and/or activation of LANCL2 and/or other immunometabolic pathways in some cells, provides the beneficial effect without causing a significant gain in weight, for example by fluid retention, in the subject being treated, as compared to other similar subjects not receiving the treatment.

As such, the immunometabolic methods of the present invention can provide treatments for reducing inflammation by affecting the metabolism of immune cells. The methods can reduce inflammation systemically (i.e., throughout the subject's body) or locally (e.g., at the site of administration or the site of inflammatory cells, including but not limited to T cells and macrophages). In treating or preventing inflammation through immunometabolism, one effect that may be observed is a shift in the metabolism of glucose. In particular, the shift may be from the production of lactate from pyruvate towards the entrance into the tricarboxylic acid cycle that is tied with immunoinflammatory actions. More specifically, this shift in metabolism can be associated with an increase in the proportion of CD4+ CD25+ FOXP3+ or other regulatory CD4+ T-cells relative to effector CD4+ T-cells such as IL17+ Th17 cells or IFNγ+ Th1 cells. Another observed effect may be decreased cellular proliferation resulting from the combination of decreased anaerobic metabolism and increased immune checkpoint pathways. Another effect of shifts in metabolism triggered therapeutically may be decreased expression of inflammatory chemokines such as MCP-1, IL-8, or CXCL9 resulting from altered processing and storage of fatty acids. The methods can thus also be considered methods of affecting or altering the immune response of a subject to whom the therapy is administered, thereby intercepting inflammation, disease and pathology.

The invention provides methods of inhibiting inflammation in the GI tract, wherein the relevant components include the stomach, small intestine, large intestine, and rectum.

The invention provides methods of treating or preventing a subject suffering from IBD, or otherwise healthy individuals, perhaps with a genetic predisposition for Crohn's Disease or ulcerative colitis, from developing IBD. The methods may also involve treating those with a remissive form of IBD. According to the invention, the term "a subject suffering from IBD" is used to mean a subject (e.g., animal, human) having a disease or disorder showing one or more clinical signs that are typical of IBD. In general, the method of treating or preventing according to this aspect of the invention comprises administering to the subject an amount of compound or cell therapy that is effective in treating or preventing one or more symptoms or clinical manifestations of IBD, or in preventing development of such symptom(s) or manifestation(s).

Thus, according to the methods of the invention, the invention can provide methods of treatment of IBD, inflammation associated with enteric infection and inflammation associated with autoimmune diseases. The methods of treatment can be prophylactic methods. In certain embodiments, the method is a method of treating IBD, inflammation associated with enteric infection and inflammation associated with autoimmune diseases. In other embodiments, the method is a method of preventing IBD.

In embodiments, the method is a method of preventing a remissive form of IBD from becoming active. In still other embodiments, the method is a method of improving the health status of a subject suffering from IBD, inflammation associated with enteric infection and inflammation associated with autoimmune diseases. Organisms causing gastroenteric infections include but are not limited to *Escherichia coli, Shigella, Salmonella*, pathogenic *Vibrios, Campylobacter jejuni, Yersina enterocolitica, Toxoplasma gondii, Entamoeba histolytica* and *Giardia lamblia*. Accordingly, in certain embodiments, the invention provides a method of protecting the health, organs, and/or tissues of a subject suffering from IBD, inflammation associated with enteric infection and inflammation associated with autoimmune diseases or at risk from developing IBD, inflammation associated with enteric infection and inflammation associated with autoimmune diseases.

In one embodiment of the invention, the method of treating IBD comprises treating IBD without causing discernable side-effects, such as significant weight gain, systemic immune suppression, cushingoid appearance, osteopenia/osteoporosis, or pancreatitis that is common of currently available IBD treatments (i.e. corticosteroids, tumor necrosis factor alpha inhibitors). That is, it has been found that the method of treating according to the present invention, which provides the treatment effect, at least in part, by affecting the expression and/or activation of LANCL2 in some cells, provides the beneficial effect without causing a significant gain in weight, for example by fluid retention, in the subject being treated, as compared to other similar subjects not receiving the treatment.

As such, the methods of the present invention can provide methods of reducing inflammation. The methods can reduce inflammation systemically (i.e., throughout the subject's body) or locally (e.g., at the site of administration or the site of inflammatory cells, including but not limited to T cells and macrophages). In treating or preventing inflammation according to the methods of the present invention, one effect that may be seen is the decrease in the number of blood monocytes or macrophages and lymphocytes infiltrating the intestine. Another may be the increase in regulatory immune cell populations, such as $CD4^+$ $CD25^+FoxP3^+$ regulatory T-cells, or an increase in regulatory properties of lymphocytes or macrophages (e.g. increased interleukin 4 (IL-4) or IL-10 or decreased TNF-α and IL-6). Another may be the decreased presence of inflammatory genes and/or adhesion molecules. The methods can thus also be considered methods of affecting or altering the immune response of a subject to whom the therapy is administered. The subject may have inflammatory bowel disease or another condition in which the immunomodulation of T cells or downregulation of cellular adhesion molecules is a desired outcome.

The invention also provides methods of treating an infectious disease with the compounds or cells described herein. Non-limiting examples of such infectious diseases include viral infections, bacterial infections, and fungal infections.

Non-limiting examples of viral infections include infections from viruses in the family adenoviridae, such as adenovirus; viruses in the family herpesviridae such as herpes simplex, type 1, herpes simplex, type 2, varicella-zoster virus, epstein-barr virus, human cytomegalovirus, human herpesvirus, and type 8; viruses in the family papillomaviridae such as human papillomavirus; viruses in the family polyomaviridae such as BK virus and JC virus; viruses in the family poxviridae such as smallpox; viruses in the family hepadnaviridae such as hepatitis B virus; viruses in the family parvoviridae such as human bocavirus and parvovirus B19; viruses in the family astroviridae such as human astrovirus; viruses in the family caliciviridae such as norwalk virus; viruses in the family picornaviridae such as coxsackievirus, hepatitis A virus, poliovirus, and rhinovirus; viruses in the family coronaviridae such as coronavirus; viruses in the family flaviviridae such as hepatitis C virus, Zika virus, yellow fever virus, dengue virus, and West Nile virus, viruses in the family togaviridae such as rubella virus; viruses in the family hepeviridae such as hepatitis E virus; viruses in the family retroviridae such as human immunodeficiency virus (HIV); viruses in the family orthomyxoviridae such as influenza virus; viruses in the family arenaviridae such as guanarito virus, junin virus, lassa virus, machupo virus, and sabia virus; viruses in the family bunyaviridae such as Crimean-Congo hemorrhagic fever virus; viruses in the family filoviridae such as ebola virus and marburg virus; viruses in the family paramyxoviridae such as measles virus, mumps virus, parainfluenza virus, respiratory syncytial virus, human metapneumovirus, hendra virus, and nipah virus; viruses in the family rhabdoviridae such as rabies virus; unassigned viruses such as hepatitis D virus; and viruses in the family reoviridae such as rotavirus, orbivirus, coltivirus, and banna virus; among others.

Non-limiting examples of bacterial infections include infections with the bacteria described above, in addition to *Bacillus anthracis, Bacillus cereus, Bordetella pertussis, Borrelia burgdorferi, Brucella abortus, Brucella canis, Brucella melitensis, Brucella suis Campylobacter jejuni Chlamydia pneumoniae, Chlamydia trachomatis, Chlamydophila psittaci, Clostridium botulinum, Clostridium difficile, Clostridium perfringens, Clostridium tetani, Corynebacterium diphtheriae, Enterococcus faecalis, Enterococcus faecium, Escherichia coli, Francisella tularensis, Haemophilus influenzae, Helicobacter pylori, Legionella pneumophila, Leptospira interrogans, Listeria monocytogenes, Mycobacterium leprae, Mycobacterium tuberculosis, Mycobacterium ulcerans, Mycoplasma pneumoniae, Neisseria gonorrhoeae, Neisseria meningitidis, Pseudomonas aeruginosa, Rickettsia rickettsii, Salmonella typhi, Salmonella typhimurium, Shigella sonnei, Staphylococcus aureus, Staphylococcus epidermidis, Staphylococcus saprophyticus, Streptococcus agalactiae, Streptococcus pneumoniae, Streptococcus pyogenes, Treponema pallidum, Vibrio cholerae, Yersinia pestis, Yersinia enterocolitica, Yersinia pseudotuberculosis*, and other species from the genera of the above-mentioned organisms.

Non-limiting examples of fungal infections include infection with fungi of the genus *Aspergillus*, such as *Aspergillus fumigatus*, which cause aspergillosis; fungi of the genus *Blastomyces*, such as *Blastomyces dermatitidis*, which cause blastomycosis; fungi of the genus *Candida*, such as *Candida albicans*, which cause candidiasis; fungi of the genus *Coccidioides*, which cause coccidioidomycosis (valley fever); fungi of the genus *Cryptococcus*, such as *Cryptococcus neoformans* and *Cryptococcus gattii*, which cause cryptococcosis; dermatophytes fungi, which cause ringworm; fungi that cause fungal keratitis, such as *Fusarium* species, *Aspergillus* species, and *Candida* species; fungi of the genus *Histoplasma*, such as *Histoplasma capsulatum*, which cause histoplasmosis; fungi of the order Mucorales, which cause mucormycosis; fungi of the genus *Saccharomyces*, such as *Saccharomyces cerevisiae*; fungi of the genus *Pneumocystis*, such as *Pneumocystis jirovecii*, which cause pneumocystis pneumonia; and fungi of the genus *Sporothrix*, such as *Sporothrix schenckii*, which cause sporotrichosis.

The invention also provides methods of treating hyperproliferative disorders with the compounds or cells described herein. Hyperproliferative disorders include conditions involving uncontrolled growth of cells, such as cancers or conditions involving the growth of tumors, adenomas, or polyps. Non-limiting examples of hyperproliferative disorders include colorectal cancer, familial adenomatous polyposis (PAP), throat cancer, thyroid cancer, gastric cancer, cancers of the gastrointestinal tract, pancreatic cancer, Hodgkin lymphoma, non-Hodgkin lymphoma, acute myeloid leukemia, hepatocellular cancer, gastrointestinal stromal tumors, acute lymphoblastic leukemia, chronic myeloproliferative disorders, hypereosinophilic syndrome, mastocytosis, among others.

The invention also provides methods of treating an inborn error of metabolism with the compounds or cells described herein. Non-limiting examples of inborn errors of metabolism include Wilson disease, Andersen disease or other glycogen storage diseases, Cystinuria, Fabry disease, adult-onset citrullinemia type II, Zellweger syndrome, branched-chain ketoaciduria, Lesch-Nyhan syndrome, Niemann-Pick disease, Fanconi-Bickel disease, von Gierke's disease, hereditary fructose intolerance, phenylketonuria, medium chain acyl-CoA dehydrogenase deficiency, among others.

The invention also provides methods of treating a chronic immunometabolic disease with the compounds or cells described herein. Non-limiting examples of chronic immunometabolic diseases include cardiovascular disease, such as atherosclerosis, coronary artery disease, peripheral artery disease, pulmonary heart disease, endocarditis, myocarditis, and hypertension.

The invention also provides methods of treating an autoimmune disease, such as an inflammatory autoimmune disease, with the compounds or cells described herein. Non-limiting examples of autoimmune diseases include inflammatory bowel disease (IBD) (e.g., Crohn's disease and ulcerative colitis), lupus, systemic lupus, Sjögren's syndrome, rheumatoid arthritis, type 1 diabetes, psoriasis, multiple sclerosis, and cancer-immunotherapy-induced autoimmune diseases, among others. Non-limiting examples of cancer-immunotherapy-induced autoimmune diseases include cancer immunotherapy-induced rheumatic diseases.

The invention also provides methods of treating chronic inflammatory diseases with the compounds or cells described herein. Non-limiting examples of chronic inflammatory diseases includes metabolic syndrome, obesity, pre-diabetes, cardiovascular disease, and type 2 diabetes, among others.

The invention also provides methods of treating inflammatory disorders such as acute colonic diverticulitis, radiation-induced inflammation of the gastrointestinal tract, and inflammation of the liver, including but limited to nonalcoholic steatohepatitis (NASH), with the compounds or cells described herein. Non-limiting examples of radiation-induced inflammation of the gastrointestinal tract include radiation proctitis, radiation enteritis, and radiation proctosigmoiditis.

The invention also provides methods of treating diabetes with the compounds or cells described herein, including type 1 diabetes, type 2 diabetes, and other types of diabetes. The term "diabetes" or "diabetes mellitus" is used to encompass metabolic disorders in which a subject has high blood sugar (i.e., hyperglycemia). Hyperglycemic conditions have various etiologies, such as the pancreas does not produce enough insulin, or cells do not respond to the insulin that is produced. There are several recognized subtypes of diabetes. Type 1 diabetes is characterized by the complete failure of the body to produce insulin or the failure of the body to produce enough insulin. Type 2 diabetes generally results from insulin resistance, a condition in which cells fail to use insulin properly. Type 2 diabetes sometimes co-presents with an insulin deficiency. Gestational diabetes occurs when pregnant women without a previous diagnosis of diabetes develop hyperglycemia. Less common forms of diabetes include congenital diabetes (due to genetic defects relating to insulin secretion), cystic fibrosis-related diabetes, steroid diabetes induced by high doses of glucocorticoids, and several forms of monogenic diabetes (including maturity onset diabetes of the young). Monogenic diabetes encompasses several hereditary forms of diabetes caused by mutations in a single, autosomal dominant gene (as contrasted to more complex, polygenic etiologies resulting in hyperglycemia).

The invention also provides methods of treating chronic pain with the compounds or cells described herein. Non-limiting examples of chronic pain diseases include fibromyalgia, nerve damage, migraine headaches, back pain, abdominal pain, among others.

The invention also provides methods of treating additional conditions with the compounds or cells described herein. These include chronic inflammatory diseases such as chronic granulomatous disease, graft versus host disease, and tumor necrosis factor receptor associated periodic syndrome; muscle wasting, such as amyotrophic lateral sclerosis, Duchenne muscular dystrophy, scoliosis, and progressive muscular atrophy; and others.

In one aspect, the invention provides methods of treating an autoimmune inflammatory disease with the compounds or cells described herein. Non-limiting examples of autoimmune inflammatory diseases include inflammatory bowel disease (IBD), systemic lupus erythematosus, rheumatoid arthritis, type 1 diabetes, psoriasis, and multiple sclerosis, among others.

The invention also provides a method of treating or ameliorating the symptoms in a subject diagnosed with systemic lupus erythematosus or preventing the development of disease in a subject genetically predisposed to systemic lupus erythematosus. Symptoms and indications of lupus that may be treated with the invention include but are not limited to lupus nephritis, central nervous system inflammation, headaches, scleritis, optic neuritis, fevers, hardening of the arteries, coronary artery disease, joint pain and malar rash. The invention also provides a method of treating additional forms of lupus including cutaneous lupus (discoid), drug-induced lupus, and neonatal lupus.

The conditions that can be treated with the methods described herein include any condition described as capable of being treated with BT-11 in any of U.S. Pat. No. 9,556,146 to Bassaganya-Riera et al.; U.S. Pat. No. 9,839,635 to Bassaganya-Riera et al.; U.S. Pat. No. 10,028,950 to Bassaganya-Riera et al.; U.S. Pat. No. 10,201,538 to Bassaganya-Riera et al.; U.S. Pat. No. 10,493,072 to Bassaganya-Riera et al.; U.S. Pat. No. 10,682,349 to Bassaganya-Riera et al.; US 2019/0160100 A1 to Bassaganya-Riera et al.; Bissel et al. 2016 (Bissel P, Boes K, Hinckley J, Jortner B S, Magnin-Bissel G, Werre S R, Ehrich M, Carbo A, Philipson C, Hontecillas R, Philipson N, Candour R D, Bassaganya-Riera J. Exploratory Studies With BT-11: A Proposed Orally Active Therapeutic for Crohn's Disease. *Int J Toxicol.* 2016 September; 35(5):521-9); and Carbo et al. 2016 (Carbo A, Gandour R D, Hontecillas R, Philipson N, Uren A, Bassaganya-Riera J. An N,N-Bis(benzimidazolylpicolinoyl)piperazine (BT-11): A Novel Lanthionine Synthetase C-Like 2-Based Therapeutic for Inflammatory Bowel Disease. *J Med Chem.* 2016 Nov. 23; 59(22):10113-10126); Leber et al. 2018 (Leber A, Hontecillas R, Zoccoli-Rodriguez V, Bassaganya-Riera J. Activation of LANCL2 by BT-11 Ameliorates 1131) by Supporting Regulatory T Cell Stability Through Immunometabolic Mechanisms. *Inflamm Bowel Dis.* 2018 Aug. 16; 24(9):1978-1991); Leber et al. 2019 Int J Toxicol. (Leber A, Hontecillas R, Zoccoli-Rodriguez V, Ehrich M, Davis J, Chauhan J, Bassaganya-Riera J. Nonclinical Toxicology and Toxicokinetic Profile of an Oral Lanthionine Synthetase C-Like 2 (LANCL2) Agonist, BT-11. *Int J Toxicol.* 2019 March/April; 38(2):96-109); Leber et al. 2019 *J Immunol.* (Leber A, Hontecillas R, Zoccoli-Rodriguez V, Chauhan J, Bassaganya-Riera J. Oral Treatment with BT-11 Ameliorates Inflammatory Bowel Disease by Enhancing Regulatory T Cell Responses in the Gut. *J Immunol.* 2019 Apr. 1; 202(7):2095-2104); and Leber et al. 2020 (Leber A, Hontecillas R, Zoccoli-Rodriguez V, Colombel J F, Chauhan J, Ehrich M, Farinola N, Bassaganya-Riera J. The Safety, Tolerability, and Pharmacokinetics Profile of BT-11, an Oral, Gut-Restricted Lanthionine Synthetase C-Like 2 Agonist Investigational New Drug for Inflammatory Bowel Disease: A Randomized, Double-Blind, Placebo-Controlled Phase I Clinical Trial. *Inflamm Bowel Dis.* 2020 Mar. 4; 26(4):643-652).

The elements and method steps described herein can be used in any combination whether explicitly described or not.

All combinations of method steps as used herein can be performed in any order, unless otherwise specified or clearly implied to the contrary by the context in which the referenced combination is made.

As used herein, the singular forms "a," "an," and "the" include plural referents unless the content clearly dictates otherwise.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, from 5 to 6, from 1 to 9, from 3.6 to 4.6, from 3.5 to 9.9, and so forth.

All patents, patent publications, and peer-reviewed publications (i.e., "references") cited herein are expressly incorporated by reference to the same extent as if each individual reference were specifically and individually indicated as being incorporated by reference. In case of conflict between the present disclosure and the incorporated references, the present disclosure controls.

It is understood that the invention is not confined to the particular construction and arrangement of parts herein illustrated and described, but embraces such modified forms thereof as come within the scope of the claims.

EXAMPLES

Molecular Modeling

Example 1. Molecular Modeling of LANCL2 Ligands

Using previously described ligands of LANCL2 including abscisic acid and NSC61610, we determined the existence of a main small molecule binding pocket on LANCL2. These ligands were docked onto a homology model structure of LANCL2 based on the crystal structure of close family homolog LANCL1 to establish important binding residues.

Figure 1C:
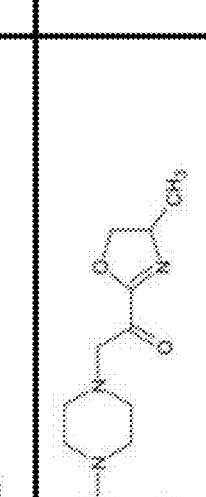
Figure 1C:
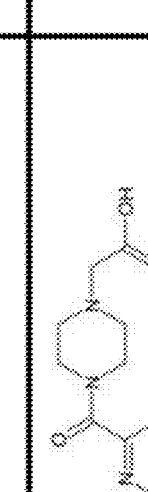

Compound generation. From the identified residues and predicted biochemical interactions, structures were generated for high affinity LANCL2 ligands (FIG. 1).

Structures were generated and chemically optimized using WebMo. Structure files were generated in .pdb format and converted to .pdbqt format through calculation of charges by Gasteiger method. Structures were docked using AutoDock Vina to confirm binding affinity in the defined binding pocket using cuboid search grid of size (21×21×21 angstrom) to provide predicted binding affinities and conformations of ligands. Binding affinity was normalized to molecular weight of the ligand. Top ligands were selected for further examination of binding pose.

Analysis. Compounds were preliminarily ranked by lowest predicted binding affinity normalized to molecular weight representing the most favorable binding pose through a minimization of total intermolecular energy, total internal energy and torsional free energy. Compounds were then prioritized based on favorable distances to critical binding residues on LANCL2.

Results. From the virtual screening and generated compounds (FIG. 1), BT-63 an asymmetric piperazine containing small molecule provided sufficient binding affinity greater than the predicted affinity of ABA (positive control). In addition to binding, BT-63 provided favorable oral drug characteristics and low safety concerns. Similar molecules within the small chemotype provided near equal affinity with slight modifications of chemical properties. These included BT-64, BT-65, BT-95, BT-96 and BT-99. Meanwhile changes on the opposite side of the molecule (BT-71, -72, -73, -74, -75) resulted in similarly small variations in binding affinity. The molecular modeling of this family of molecules supports the claim that the encompassed chemotype has LANCL2-binding properties.

Medicinal Chemistry

Example 2A. Synthesis of BT-63

BT-63, (2-(4-(6-(1H-benzo[d]imidazol-2-yl) picolinoyl) piperazin-1-yl)-1-phenylethanone, can be synthesized through a five-step process. Sulfur powder was added to a mixture of benzene-1, 2-diamine and 2, 6-dimethylpyridine, then heated to 160° C.

Reaction mixture was diluted with methanol, filtered and evaporated under reduced pressure to obtain 2-(6-methylpyridin-2-yl)-1H-benzo[d]imidazole. Selinium dioxide was added to a solution of 2-(6-methylpyridin-2-yl)-1H-benzo[d]imidazole in pyridine and heated to 110° C. Solvent from the reaction mixture was evaporated under reduced pressure and the obtained crude extracted with ethyl acetate. Dried solid was filtered and dried under vacuum to obtain 6-(1H-benzo[d]imidazol-2-yl) picolinic acid. DIPEA was added to a solution of tert-butyl piperazine-1-carboxylate and 2-bromo-1-phenylethanone in DCM at 0° C. and stirred. Reaction mixture was diluted with ice water and organic layer was separated to obtain tert-butyl 4-(2-oxo-2-phenylethyl) piperazine-1-carboxylate. 4N HCl in 1,4-dioxane was added to a solution of tert-butyl 4-(2-oxo-2-phenylethyl) piperazine-1-carboxylate in DCM at 0° C. and stirred at RT. Solvent was evaporated to obtain 1-Phenyl-2-(piperazin-1-yl) ethanone.HCl as off white solid. HATU was added to a solution of 6-(1H-benzo[d]imidazol-2-yl) picolinic acid, 1-Phenyl-2-(piperazin-1-yl) ethanone.HCl and DIPEA in DMF and stirred. Reaction mixture was diluted and extracted with ethyl acetate. The combined organic layer was dried with sodium sulphate and evaporated under reduced pressure. The obtained crude was purified by Grace purification system in silica 40 μm column using methanol-dichloromethane as eluent to obtain 2-(4-(6-(1H-benzo[d]imidazol-2-yl) picolinoyl) piperazin-1-yl)-1-phenylethanone. $^1$H NMR (400 MHz, DMSO): δ 12.98 (s, 1H), 8.37 (d, J=8.00 Hz, 1H), 8.10 (t, J=8.00 Hz, 1H), 7.99 (d, J=6.80 Hz, 2H), 7.72 (d, J=8.40 Hz, 1H), 7.65-7.48 (m, 5H), 7.28-7.18 (m, 2H), 3.95 (s, 2H), 3.74 (t, J=4.80 Hz, 2H), 3.45 (t, J=4.80 Hz, 2H), 2.68 (t, J=4.80 Hz, 2H), 2.55 (t, J=4.80 Hz, 2H).

Example 2B. Synthesis of BT-104-A

BT-104-A, (2-(4-(6-(1H-benzo[d]imidazol-2-yl) picolinoyl) piperazin-1-yl)-2-methyl-1phenylpropan-1-one, can be synthesized through a six-step process.

Dimethyl-2,6-pyridinecarboxylate was stirred in methanol and cooled to 10 to 20° C. Potassium hydroxide was slowly added to reaction mass and stirred for 6 hours. After completion of reaction, solvent was evaporated to obtain 2,6-pyridinedicarboxylic acid monomethyl ester.

2,6-pyridinedicarboxylic acid monomethyl ester was stirred in n-methyl pyrrolidone and cooled to 10 to 20° C. DIPEA, EDC.HCl and HOBt were sequentially added to reaction mixture. Following solvent addition, benzene-1,2-diamine was added and stirred for 24 h. After completion of reaction, solvent was evaporated to obtain 6-(methoxycarbonyl)pyridine-2-(2'-aminoacetanilide).

6-(methoxycarbonyl)pyridine-2-(2'-aminoacetanilide) was stirred in acetic acid for 15 minutes. Reaction mass was heated to 60-65° C. and stirred for 16 h. After completion of reaction, solvent was evaporated to obtain 6-(1H-benzo[d]imidazol-2-yl)methylpicolinate.

6-(1H-benzo[d]imidazol-2-yl)methylpicolinate was added to lithium hydroxide in THF/water and stirred for 7 h. After completion of reaction, solvent was evaporated to obtain 6-(1H-benzo[d]imidazol-2-yl)picolinic acid.

Sodium methoxide was added to a solution of 2-bromo-2-methyl-1-phenylpropan-1-one in dry methanol and heated at 40° C. for 4 h. Crude product was taken in toluene. Piperazine was added to crude product and refluxed for 16 h. After completion of reaction, solvent was evaporated under reduced pressure to obtain 2-methyl-1-phenyl-2-(piperazin-1-yl)propan-1-one.

6-(1H-benzo[d]imidazol-2-yl)picolinic acid in TEA was added to a solution of 2-methyl-1-phenyl-2-(piperazin-1-yl) propan-1-one in THE and stirred for 10 min. T3P in ethyl acetate was added and stirred for 6 h. After completion of reaction, solvent was evaporated under reduced pressure. Product was purified to obtain (2-(4-(6-(1H-benzo[d]imidazol-2-yl) picolinoyl) piperazin-1-yl)-2-methyl-1phenylpropan-1-one (BT-104-A). $^1$H NMR (400 MHz, DMSO-d6): δ 10.34 (s, 1H), 8.51 (d, J=8.0 Hz, 2H), 8.45 (d, J=7.6 Hz, 1H), 7.95 (t, J=8.0 Hz, 1H), 7.85 (d, J=6.4 Hz, 1H), 7.59 (d, J=6.4 Hz, 1H), 7.57-7.50 (m, 2H), 7.42 (t, J=7.6 Hz, 2H), 7.35-7.30 (m, 2H), 3.88 (br s, 2H), 3.53 (t, J=4.80 Hz, 2H), 2.77 (t, J=4.80 Hz, 2H), 2.57 (t, J=4.80 Hz, 2H), 1.37 (s, 6H).

Example 2C. Synthesis of BT-104-B

BT-104-B, 4-(6-(1H-benzo[d]imidazol-2-yl)picolinoyl)-1-(2-oxo-2-phenylethyl)piperazine-2,6-dione, can be synthesized through a six-step process.

Dimethyl-2,6-pyridinecarboxylate was stirred in methanol and cooled to 10 to 20° C. Potassium hydroxide was slowly added to reaction mass and stirred for 6 hours. After completion of reaction, solvent was evaporated to obtain 2,6-pyridinedicarboxylic acid monomethyl ester.

2,6-pyridinedicarboxylic acid monomethyl ester was stirred in n-methyl pyrrolidone and cooled to 10 to 20° C. DIPEA, EDC.HCl and HOBt were sequentially added to reaction mixture. Following solvent addition, benzene-1,2-diamine was added and stirred for 24 h. After completion of reaction, solvent was evaporated to obtain 6-(methoxycarbonyl)pyridine-2-(2'-aminoacetanilide).

6-(methoxycarbonyl)pyridine-2-(2'-aminoacetanilide) was stirred in acetic acid for 15 minutes. Reaction mass was heated to 60-65° C. and stirred for 16 h. After completion of reaction, solvent was evaporated to obtain 6-(1H-benzo[d]imidazol-2-yl)methylpicolinate.

6-(1H-benzo[d]imidazol-2-yl)methylpicolinate was added to lithium hydroxide in THF/water and stirred for 7 h. After completion of reaction, solvent was evaporated to obtain 6-(1H-benzo[d]imidazol-2-yl)picolinic acid.

Piperazine-2,6-dione in TEA was added to a solution of 6-(1H-benzo[d]imidazol-2-yl) picolinic acid in THE and stirred for 10 min. T3P in ethyl acetate was then added and stirred for 2 h. After completion of reaction, reaction mixture was extracted with ethyl acetate and washed with water to obtain 1-(6-(1H-benzo[d]imidazol-2-yl)picolinoyl)-piperazine-2,6-dione.

2-bromo-1-phenylethan-1-one in DIPEA was added to a solution of 1-(6-(1H-benzo[d]imidazol-2-yl)picolinoyl)-piperazine-2,6-dione in dry DCM:DMF and stirred for 2 h. After completion of reaction, reaction mixture was extracted with ethyl acetate and washed with water. Material was dried and purified to obtain 4-(6-(1H-benzo[d]imidazol-2-yl)picolinoyl)-1-(2-oxo-2-phenylethyl)piperazine-2,6-dione (BT-104-B). $^1$H NMR (400 MHz, DMSO-d6): δ 12.88 (s, 1H), 8.46 (d, J=7.60 Hz, 1H), 8.20 (t, J=8.00 Hz, 1H), 8.07 (d, J=8.00 Hz, 2H), 7.84 (d, J=7.60 Hz, 1H), 7.75-7.71 (m, 2H), 7.60-7.56 (m, 3H), 7.30-7.24 (m, 2H), 5.25 (s, 2H), 4.86 (d, J=4.40 Hz, 4H). Purity by HPLC: 98.82%; MS: m/z 452.26 (M-H).

Receptor Binding

Example 3. Surface Plasmon Resonance Binding to LANCL2

Introduction

Virtual screening and in silico experimentation are valuable means to identify and prioritize scaffolds of interest when designing new small molecule ligands for a therapeutic target. To validate these findings, numerous in vitro methods exist to determine the affinity of a small molecule to the protein of interest. One particular method is surface plasmon resonance, which is ability to estimate steady state binding by flowing a suspension of ligand over immobilized purified protein. This method was used to evaluate prospective LANCL2 ligands.

Methods LANCL2 production and purification. LANCL2 was cloned into *E. coli*, amplified and transfected in *Pichia pastoris*. *P. pastoris* was plated onto adenine selective media. Stable transfected colonies were selected and grown within YPD broth at 30° C. for 24 hours, 240 RPM shaking. Starter culture was used to inoculate base media (1% yeast extract, 2% peptone, 1% sorbitol, 2% yeast nitrogen base) containing biotin and buffered with potassium phosphate. Inoculated base media was incubated for 48 hours at 30° C., 240 RPM. *P. pastoris* was then pelleted by centrifugation and resuspended in expression media (1% sorbitol, 2% yeast nitrogen base) containing biotin and buffered with potassium phosphate. Culture was induced daily for protein production through addition of methanol and incubated for a total of 4 days at 28° C., 240 RPM. After incubation, cells were pelleted by centrifugation and lysed by sonication. Recombinant LANCL2 protein was purified by fast protein liquid chromatography (AktaPrime) using immobilized metal affinity chromatography. Fractions of protein were eluted in 1 mL aliquots and evaluated for LANCL2 content.

Surface plasmon resonance. A Biacore T200 was used to evaluate binding to the LANCL2 protein. Protein was immobilized onto the CM5 sensor chip. LANCL2 was diluted in 10 mM sodium acetate buffer at pH 4.0 and immobilized onto the flow cell to a level of ~3700 RU, using standard amine coupling chemistry. Based on the immobilized response values, theoretical $R_{max}$ values were calculated. The $R_{max}$ values assume 1:1 interaction mechanism. Overnight kinetics were performed for all analytes binding to the immobilized proteins. The kinetics experiments were performed in the presence of running buffer+1% DMSO. The flow rate of all solutions was maintained at 50 L/min. Analyte concentrations were 0 μM, 2.5 μM, 5 μM, 10 μM, 20 μM, and 40 μM.

Results

BT-63 bound to the LANCL2 protein with a $K_D$ of 2.74 μM. Surface plasmon resonance validates the predicted binding of this family of molecules of the described Markush structure to LANCL2. In comparison, BT-62, a molecule identical to BT-63 except for the methylene between the piperazine and carbonyl in BT-63, had a $K_D$ of 18.0 μM. The addition of the methylene provides increased affinity for LANCL2 with a $K_D$ in similar range to that of BT-11, an LANCL2 targeting therapeutic.

Experimental Studies

Example 4. Pharmacokinetics of BT-63

Introduction

In addition to induction of immune effects, a pharmaceutical compound must also reach compartments within the body at adequate concentrations to provide therapeutic benefit. Further, early evaluation of the pharmacokinetics is needed to determine the desired route of administration.

Methods

C57BL/6 mice were dosed orally with 10 and 40 mg/kg of BT-63 by oral gavage of methylcellulose solution containing BT-63. After gavage, blood was collected at 0.5, 1, 2, 4, 6, 8, 12 and 24 hours after treatment. Plasma was collected from blood by centrifugation. BT-63 was extracted from plasma and quantified by LC-MS/MS.

Results

Figure 2:
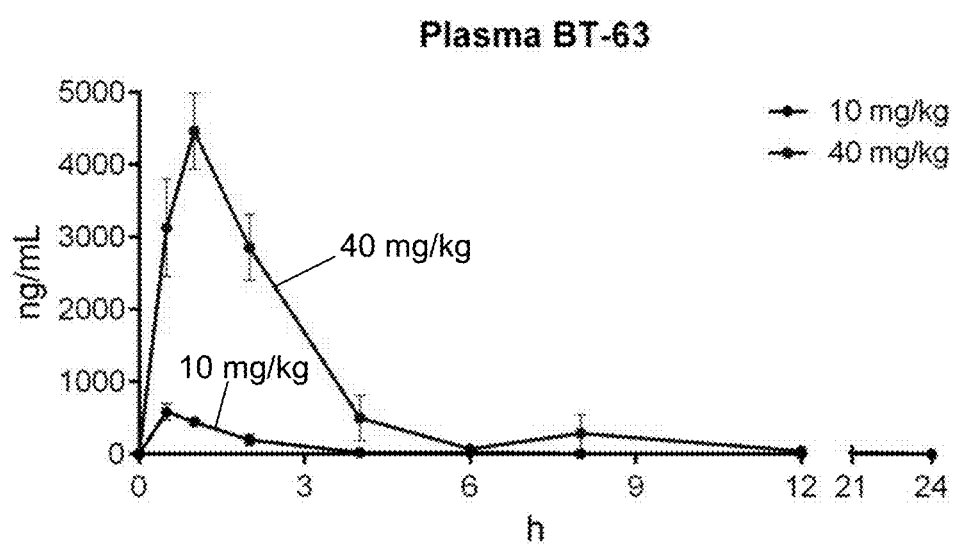
FIG. 2. Pharmacokinetics of BT-63 after oral dosing with 10 and 40 mg/kg.

Oral BT-63 (10 mg/kg) resulted in a maximum plasma concentration of 585 ng/mL and an area under the curve exposure of 1055 hr*ng/mL (FIG. 2). Oral dosing with 40 mg/kg resulted in a sharp increase in maximum plasma concentration (4465 ng/mL) as well as exposure (11552 ng/mL). The results indicate that BT-63 is viable as an oral therapeutic small molecule. Based on these results, BT-63 is a highly bioavailable compound in contrast to other LANCL2 targeting compounds such as BT-11. Notably, at equal oral doses BT-63 has a >100-fold increase in maximum plasma concentration in mice compared to BT-11 (4.9 ng/mL at dose of 10 mg/kg).

Example 5. Identification of Immune Effects in CD4+ T Cells

Introduction

Figure 15:
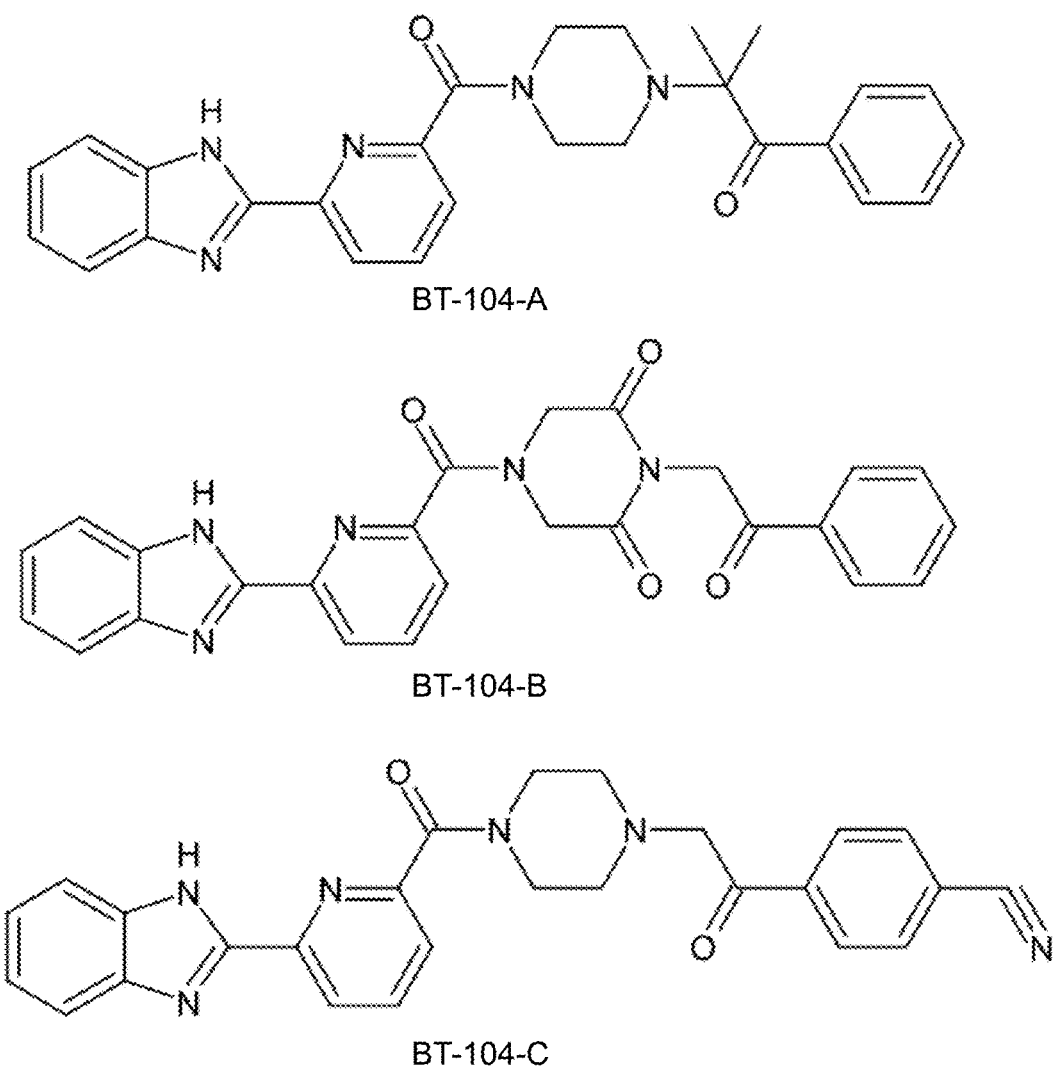
FIG. 15. Additional exemplary compounds of the invention (BT-104-A, BT-104-B, BT-104-C) that bind to LANCL2 and that can be used in any method described herein. The conversion of the piperazine in BT-63 to piperazine-2,6-dione, as present in BT-104-A, or the addition of the gem-dimethyl or nitrile groups to BT-63, as present in BT-104-B or BT-104-C, respectively, serve to improve the systemic half-life of the target compound through the improvement of the resistance of the methylene group in BT-63 to enzymatic metabolism.

Central to the pathogenesis of many autoimmune diseases is the dysfunction of CD4+ T helper cells. These cells are important in maintaining the health of an individual, amplifying immune responses and promoting homeostasis. However, in the case of autoimmune and inflammatory disease, CD4+ T helper cells can become overactive, activated in the absence of stimuli or unable to resolve inflammation. In these scenarios, therapeutics that can mitigate or prevent inflammation are valuable treatments for the management of disease. In this end, we validated the functional therapeutic potential of BT-63, BT-104-A (see FIG. 15), BT-104-B (see FIG. 15), and BT-104-C (see FIG. 15), LANCL2-binding ligands, in this cell type.

Methods

Cell culture. Spleens were excised from C57BL/6 mice and assessed in wild-type and LANCL2 deficient states. Spleens were crushed between the frosted ends of microscope slides and filtered to provide a cellular suspension. Red blood cells were lysed through hypotonic lysis. Remaining cells were washed and filtered. CD4+ T cells were enriched within the suspension using magnetic sorting based negative selection. Cells were collected and plated within 96 well plates coated with anti-CD3 and cultured in the presence of BT-63 at 0, 0.1, 1 and 10 micromolar or BT-104A, BT-104B, or BT-104C at 0.1 micromolar for 48 h. During the last 6 h of culture, cells were stimulated with phorbol 12-myristate-13-acetate (PMA) and ionomycin.

Immunological analysis. Cells were collected from 96 well plates and stained with a cocktail of antibodies for immunophenotyping by flow cytometry. Culture supernatant was collected and assayed for cytokine concentrations by cytometric bead array. Data was captured on a BD FACS Celesta and analyzed using FacsDiva.

Results

Figure 3:
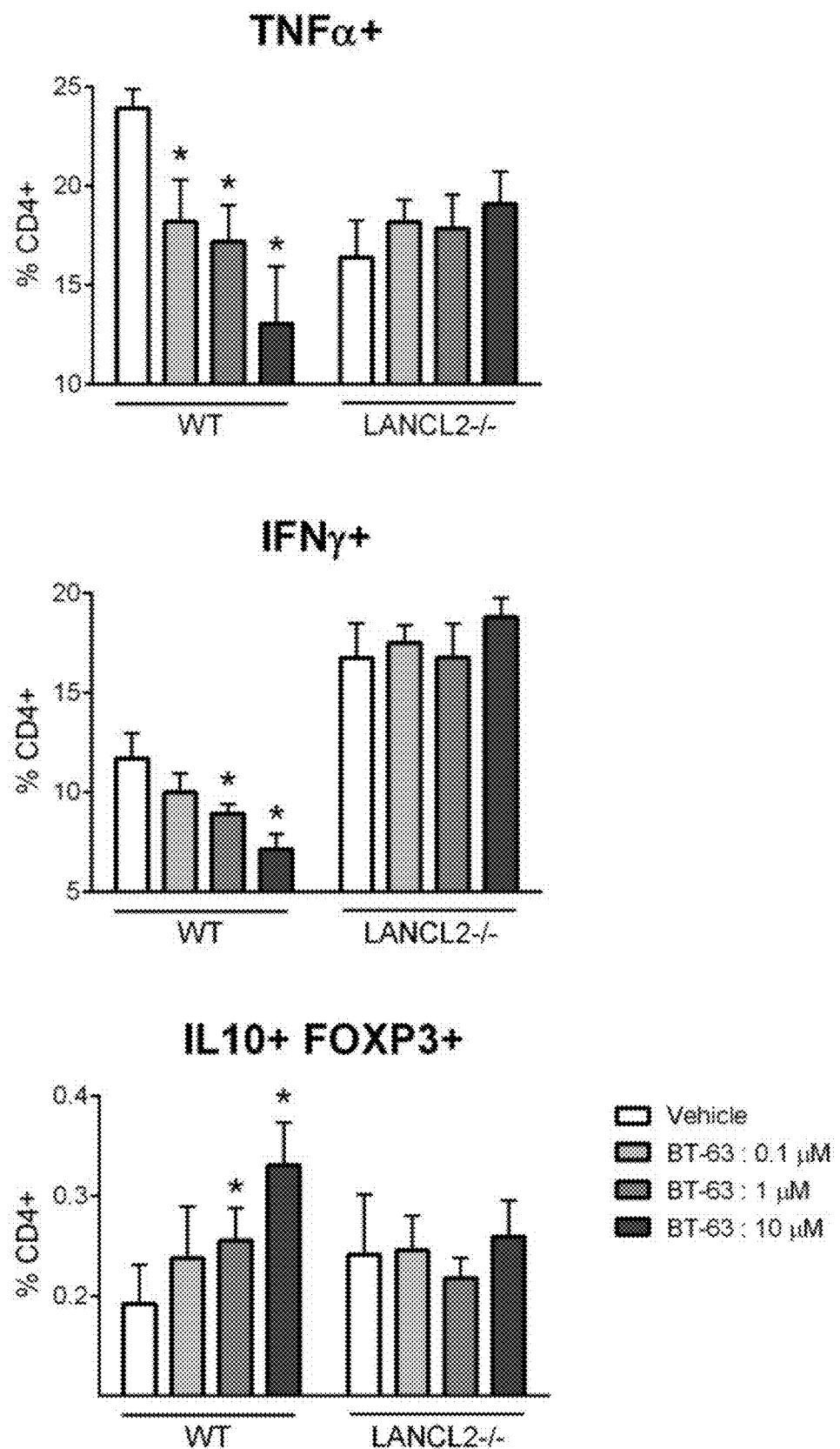
FIG. 3. Immunological validation of BT-63 activity in CD4+ splenocytes. Percentages of IFNγ+, TNFα+, and IL10+ FOXP3+ CD4+ T cells were measured by flow cytometry after in vitro treatment of cells with BT-63 at concentrations of 0.1, 1 and 10 μM in wild type and LANCL2 deficient cells. Statistical significance (p<0.05) is marked by asterisks.

BT-63 reduced proportions of IFNγ-producing and TNFα-producing CD4+ T cells within wild-type cell culture and increased proportions of IL10+ FOXP3+ CD4+ T cells (FIG. 3). In the absence of LANCL2, these effects were lost. From a downregulation of inflammatory cytokines, these results indicate that BT-63 may function as an activator of LANCL2. Given the loss of activity in LANCL2 deficient cells, BT-63 has dominant mechanistic actions through the LANCL2 pathway. Combined with results of in silico and in vitro binding, the actions through the LANCL2 pathway are likely a result of direct binding to LANCL2.

Figure 4A:
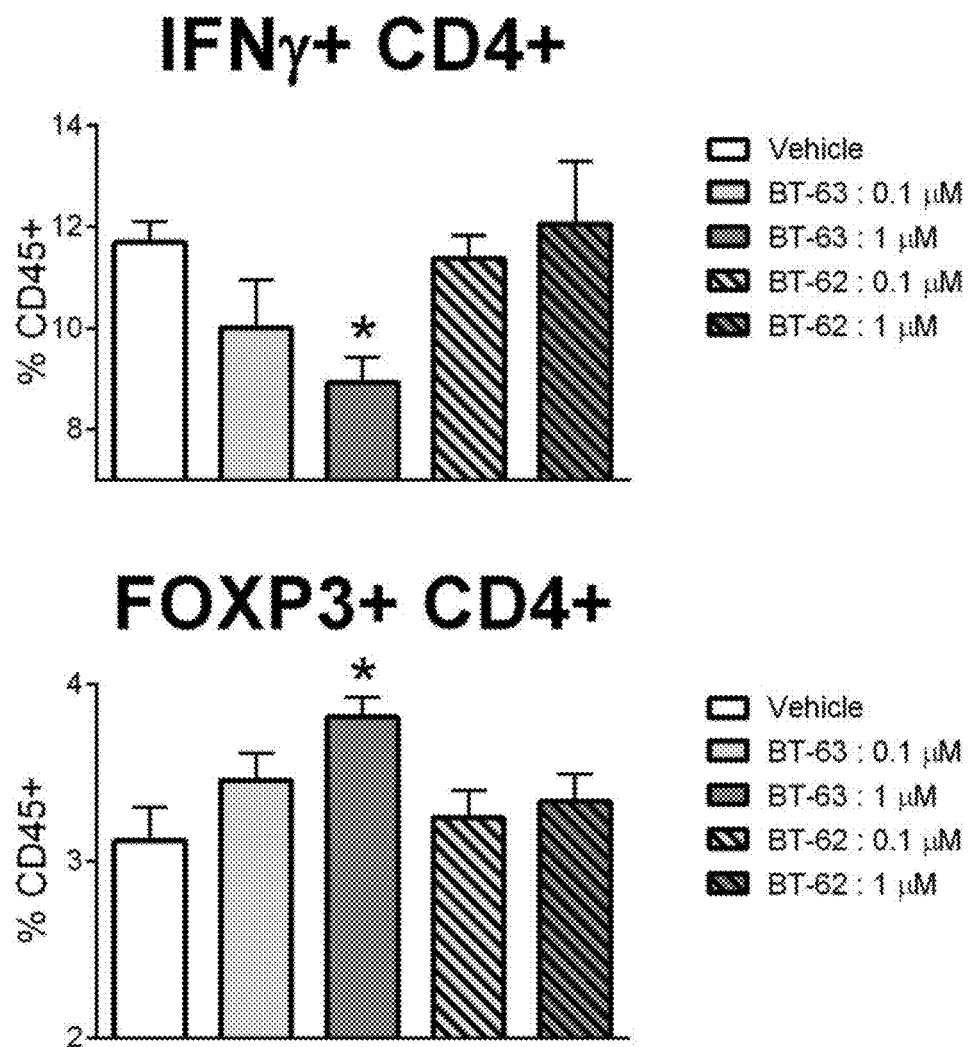
FIGS. 4A and 4B. Activity of compounds in CD4+ splenocytes. Percentages of IFNγ+ and FOXP3+ CD4+ T cells were measured by flow cytometry after in vitro treatment of cells with BT-63 and BT-62 at concentrations of 0.1, 1 and 10 micromolar (FIG. 4A). Percentages of IFNγ+ and TNF+ CD4+ T cells were measured by flow cytometry after in vitro treatment of cells with BT-104-A, BT-104-B and BT-104-C at a concentrations of 0.1 micromolar (FIG. 4B). Statistical significance (p<0.05) is marked by asterisks.

Additionally, BT-63 provides greater immune effects compared to BT-62 (FIG. 4A). While BT-63 provides a significant increase in FOXP3+ cells and a significant decrease of IFNγ+ cells, BT-62 does not induce either change at the tested concentrations. Therefore, the alkylene linker between the piperazine and carbonyl groups is critical for higher binding affinity to LANCL2 and greater immunological efficacy.

Figure 4B:
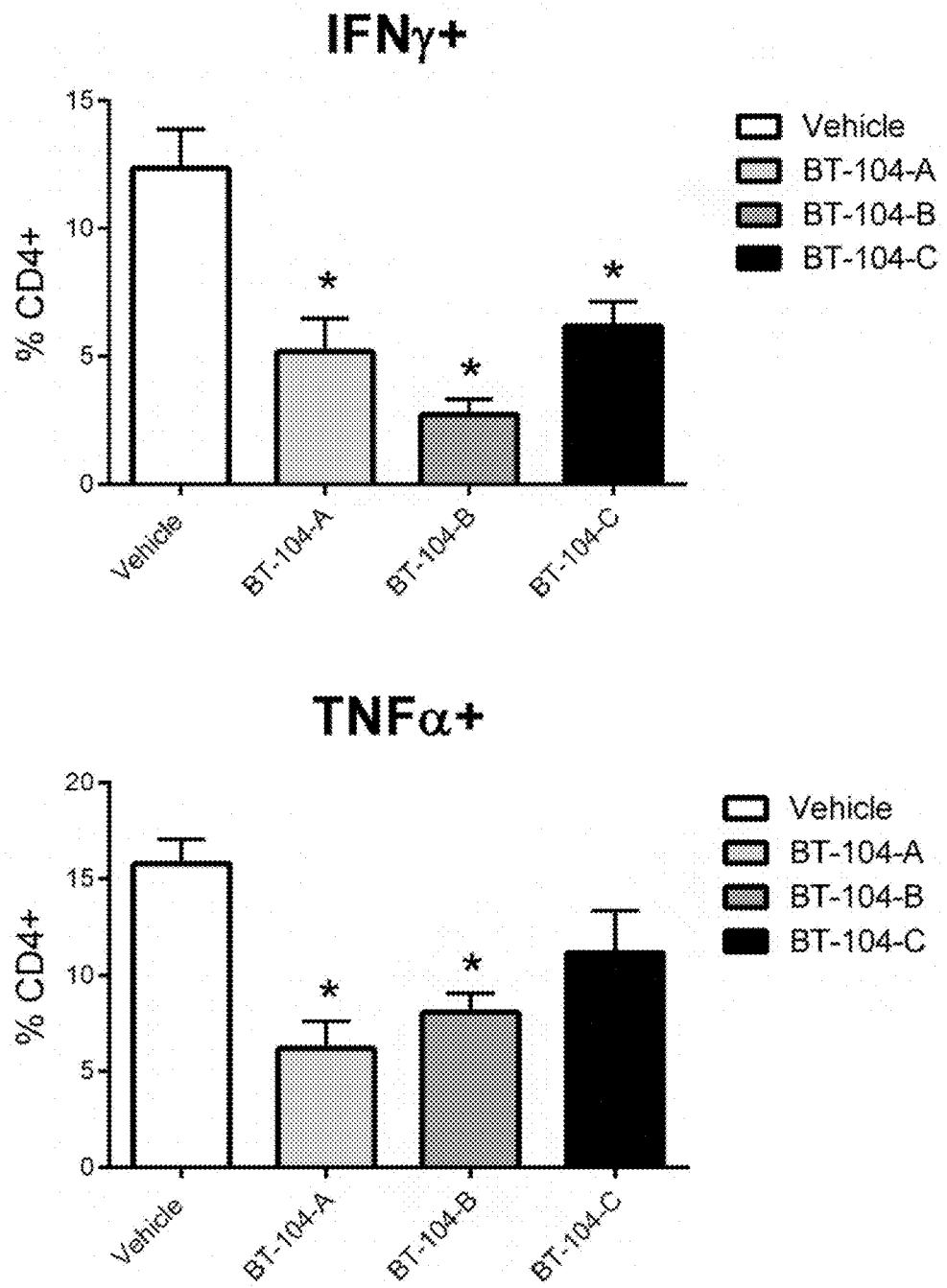

BT-104-A, BT-104-B, and BT-104-C were observed to significantly decrease the proportions of IFNγ+ CD4+ T cells, with BT-104-A and BT-104-B also significantly decreasing TNFα+ CD4+ T cells (FIG. 4B). Out of the three compounds, BT-104-B was observed to have the greatest numerical effect on IFNγ+ cells, and BT-104-A was observed to have the greatest numerical effect on TNFα+ cells, though the only statistical differences observed were relative to vehicle.

Example 6. Use of BT-63 in a NOD Mouse Model of T1D

Introduction

Type 1 Diabetes (T1D) is an autoimmune disease in which the immune system destroys insulin-producing pancreatic cells necessitating life-long insulin therapy through injections or pumps. With current treatments, glycemic control is difficult resulting in prolonged periods of hyperglycemia and dysregulated glucose metabolism that contribute to organ damage and co-morbidities (blindness, kidney failure, cardiovascular disease, loss of extremities). Currently no treatments are approved for the prevention of disease progression at onset (i.e. restoring immunological tolerance to diabetes-associated antigens to allow regrowth of pancreatic beta cells) and very few are approved to assist in glycemic control. LANCL2 is a potent receptor that contributes to immune responses, cellular metabolism and survival of cells. With this three-fold mechanism, LANCL2 is an attractive target for acute and long-term maintenance therapy in T1D.

Methods

NOD model. Non-obese diabetic (NOD) ShiLt mice were used in this study. NOD mice have numerous genetic mutations that enable the spontaneous onset of hyperglycemia and pancreatic pathologies associated with T1D. Mice entered into the experiment at 9 weeks of age and were monitored for a 12 period. Mice were treated daily with vehicle, 10 mg/kg BT-63, or 20 mg/kg BT-63 by oral gavage. Once weekly blood samples were collected from the tail vein to be tested for glucose concentration by glucometer. Mice were euthanized after 12 weeks for collection of blood and organs for immunological testing.

Treatment administration. BT-63 was prepared within a 0.5% methylcellulose (12-15 cP) solution. Dosage used was 10 or 20 mg/kg delivered once daily. Mice were weighed on a weekly basis to update dosage formulation. Dosage was calculated based off mean body weights for each gender. Oral dosage was delivered by orogastric gavage of dosage in 0.2 mL volume.

Immunological analysis. Blood was collected by cardiac puncture into heparinized tube. Plasma was separated following centrifugation and assayed by Luminex for cytokine and hormones related to the development of T1D. Spleens were excised, crushed and filtered to provide a cellular suspension. Red blood cells were lysed. Cells were labeled with mixtures of extracellular (CD45, CD3, CD4, CD8, CD19, NK1.1, CD25, F4/80, CD11b, Gr1, CX3CR1, CD64) and intracellular (Tbet, BCL6, FOXP3, IFNγ, IL21, IL10) antibodies in a sequential live staining in 96-well plates in preparation for flow cytometry. Data was captured on a BD FACS Celesta and analyzed using FacsDiva.

Results

Figure 5:
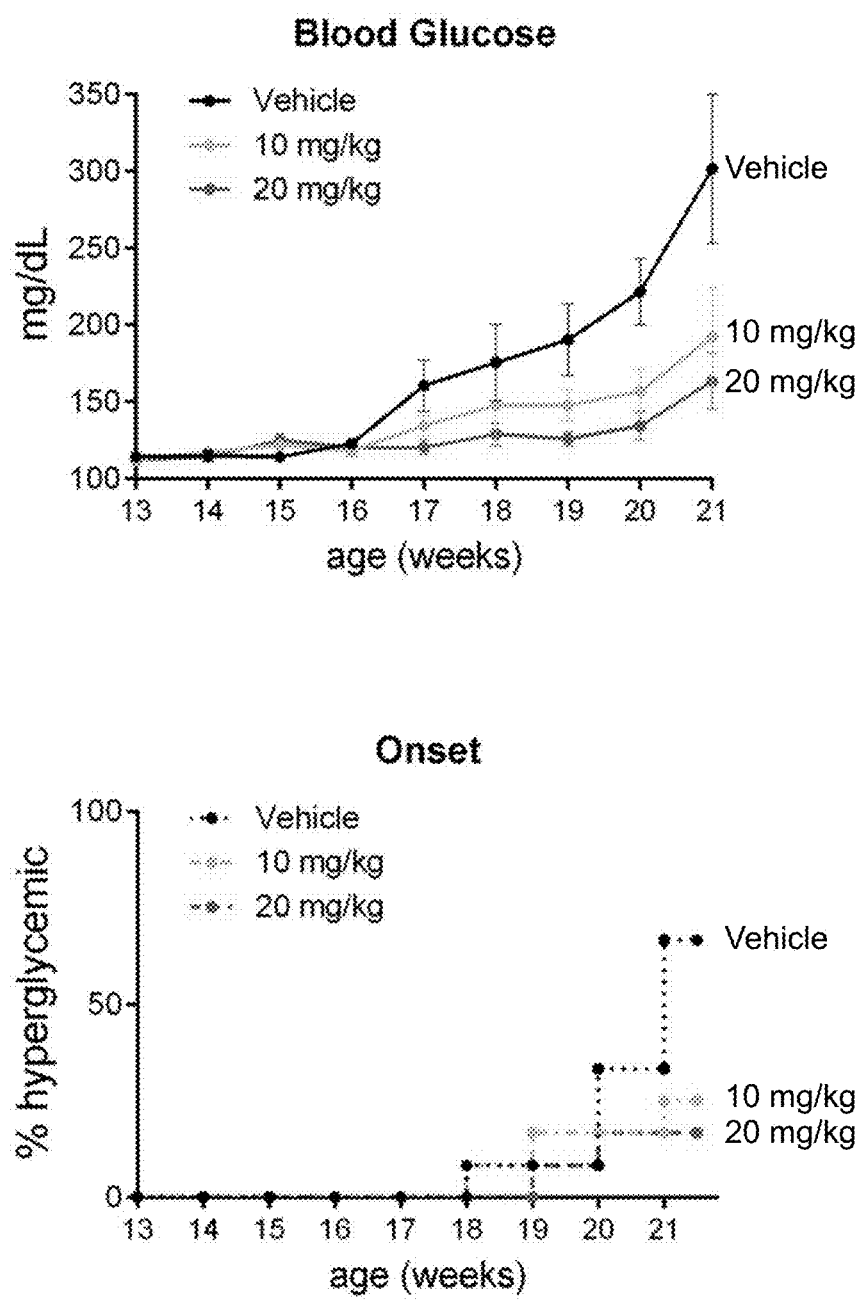
FIG. 5. Efficacy of BT-63 in a NOD model of T1D. Weekly blood glucose and percent hyperglycemic monitoring of NOD mice treated with vehicle or 10 or 20 mg/kg BT-63 daily.
Figure 6:
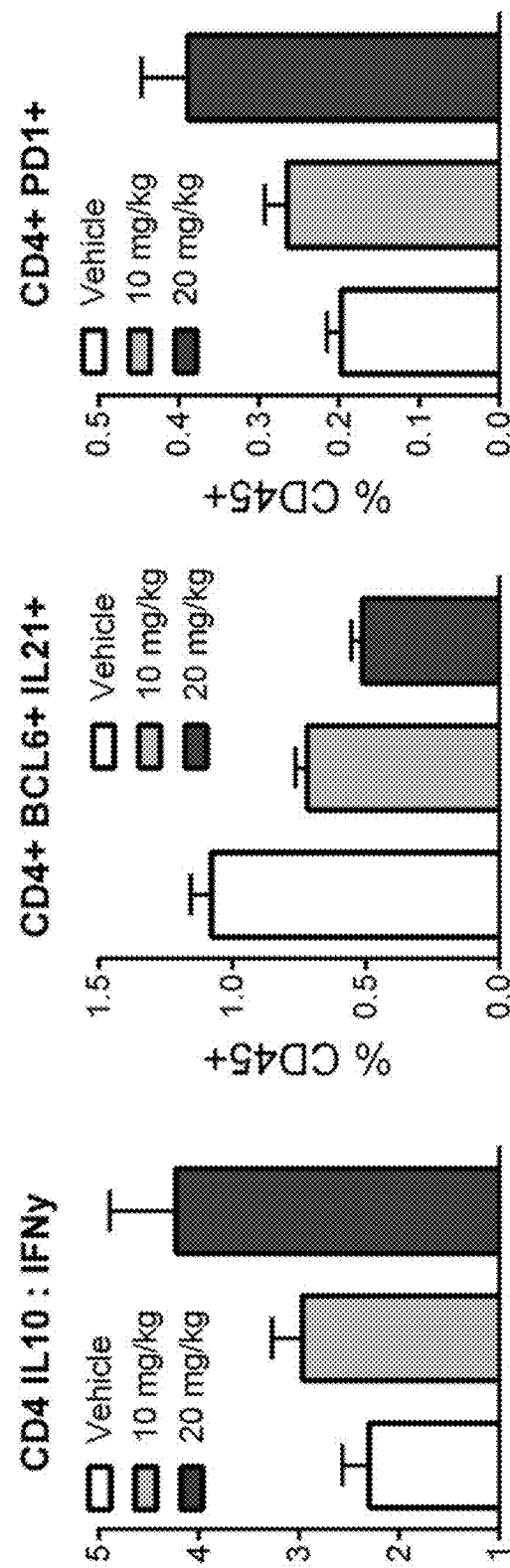
FIG. 6. Immune effects of BT-63 in vivo in a NOD model of type 1 diabetes (T1D). Ratio of splenic IL10 producing cells to IFNγ producing cells, splenic BCL6+IL21+ CD4+ T helper cells and CD4+ PD1+ T cells at 21 weeks of age with oral treatment of vehicle or 10 or 20 mg/kg BT-63 daily.
Figure 7:
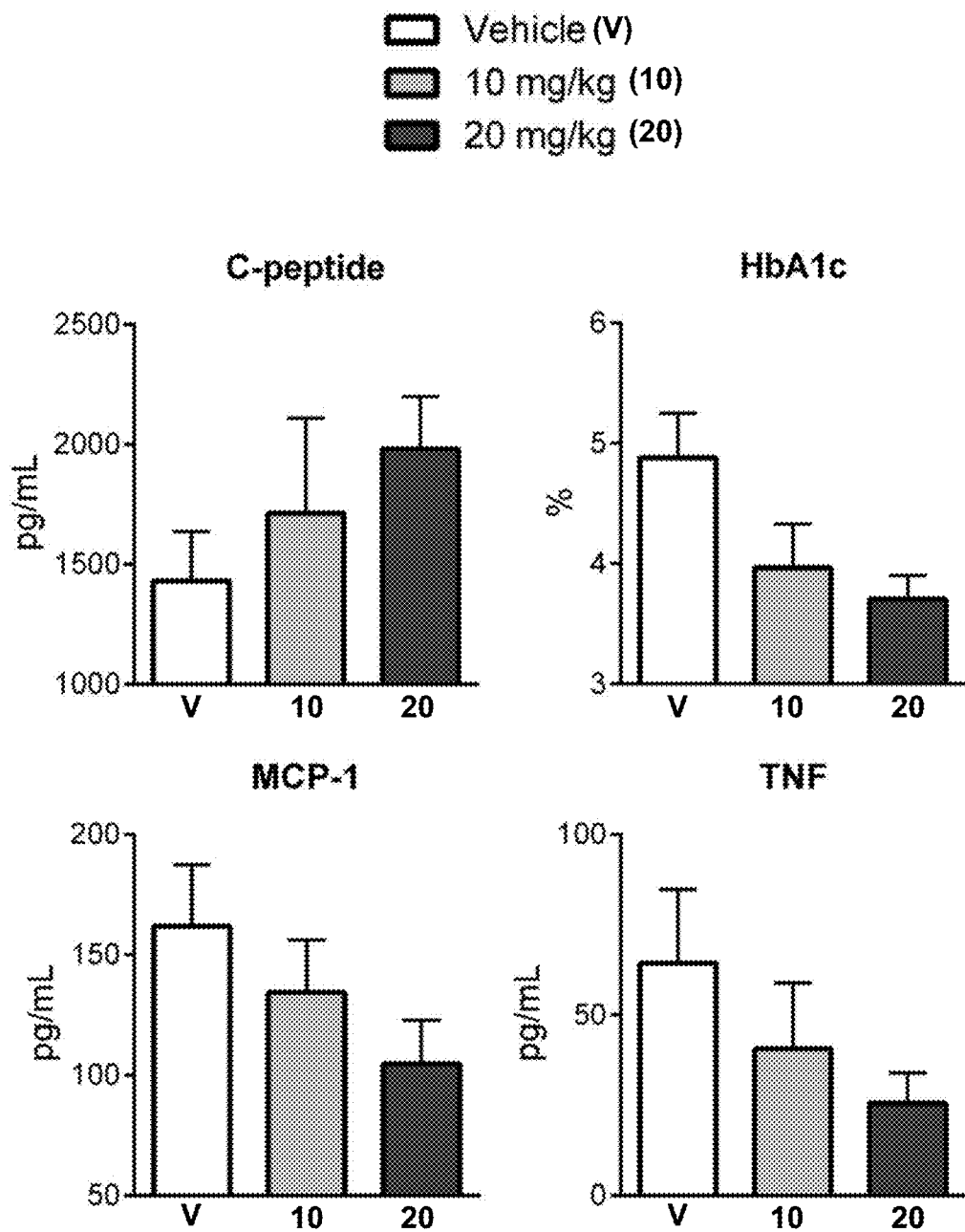
FIG. 7. Plasma biomarker evaluation of BT-63 in a NOD model of T1D. Plasma concentrations of C-peptide, HbA1c, MCP-1, and TNF at 21 weeks of age with oral treatment of vehicle or 10 or 20 mg/kg BT-63 daily.

Oral BT-63 protected against the development of hyperglycemia. Mice treated with BT-63 had significantly lower blood glucose levels from 19 weeks of age through the end of the experiment (FIG. 5). The percentage of hyperglycemic mice was reduced by 50% in the 20 mg/kg group compared to the vehicle treated group while the HbA1c at 21 weeks of age was reduced in both 10 mg/kg and 20 mg/kg dose groups. In the spleen, oral BT-63 increased the CD4+ IL10+ to CD4+ IFNγ+ ratio while decreasing T follicular helper (Tfh) cells (BCL6+IL21+) and increasing PD1+ CD4+ T cells (FIG. 6). BT-63 also increased plasma levels of insulin and C-peptide and reduced MCP-1 and TNF (FIG. 7). The data supports BT-63 as a preventative and restorative therapy in T1D.

Example 7. Use of BT-63 in a TLR-Induced Mouse Model of SLE

Introduction

Systemic lupus erythematosus (SLE) is a systemic autoimmune disease that can cause damage to kidneys, cardio-vasculature, and joints. Due to self-tolerance, standard apoptosis of cells results in the generation of nuclear antigens that are processed without immune response in non-SLE afflicted individuals. However, in SLE, the immune system responds to these antigens generating antibodies to double-stranded DNA (dsDNA) and other nuclear antigens that form immune complexes that can deposit throughout the body and cause unwarranted immune responses. Disease is currently treated with steroids, biologics and other immunosuppressants with a high likelihood of detrimental side effects and weakening of the body's immune system. Treatment through LANCL2 activating ligands could restore immunological tolerance and reduce the production of self-targeted antibodies.

Methods

Resiquimod model. Resiquimod was prepared in a 1:3 ethanol:acetone mixture to provide 85 micrograms of resiquimod to each mouse. Resiquimod solution was well mixed and applied to the ear of C57BL6 mice three times weekly over a 2-week period. Mice were monitored for signs of disease daily.

Treatment administration. BT-63 was prepared within a 0.5% methylcellulose (12-15 cP) solution. Dosage used was 20 mg/kg delivered once daily. Mice were weighed on a weekly basis to update dosage formulation. Dosage was calculated based off mean body weights for each gender. Oral dosage was delivered by orogastric gavage of dosage in 0.2 mL volume.

Immunological analysis. Blood was collected by cardiac puncture into EDTA tube. Plasma was separated following centrifugation and assayed by ELISA for anti-dsDNA antibodies. Urine was collected for assay for albumin content to test for kidney function. Spleens were excised, crushed and filtered to provide a cellular suspension. Red blood cells were lysed. Cells were labeled with mixtures of extracellular (CD45, CD3, CD4, CD8, CD19, NK1.1, CD25, F4/80, CD11b, Gr1, CX3CR1, CD64) and intracellular (Tbet, BCL6, FOXP3, IFNγ, IL6, IL10) antibodies in a sequential live staining in 96-well plates in preparation for flow cytometry. Data was captured on a BD FACS Celesta and analyzed using FacsDiva.

Results

Figure 8:
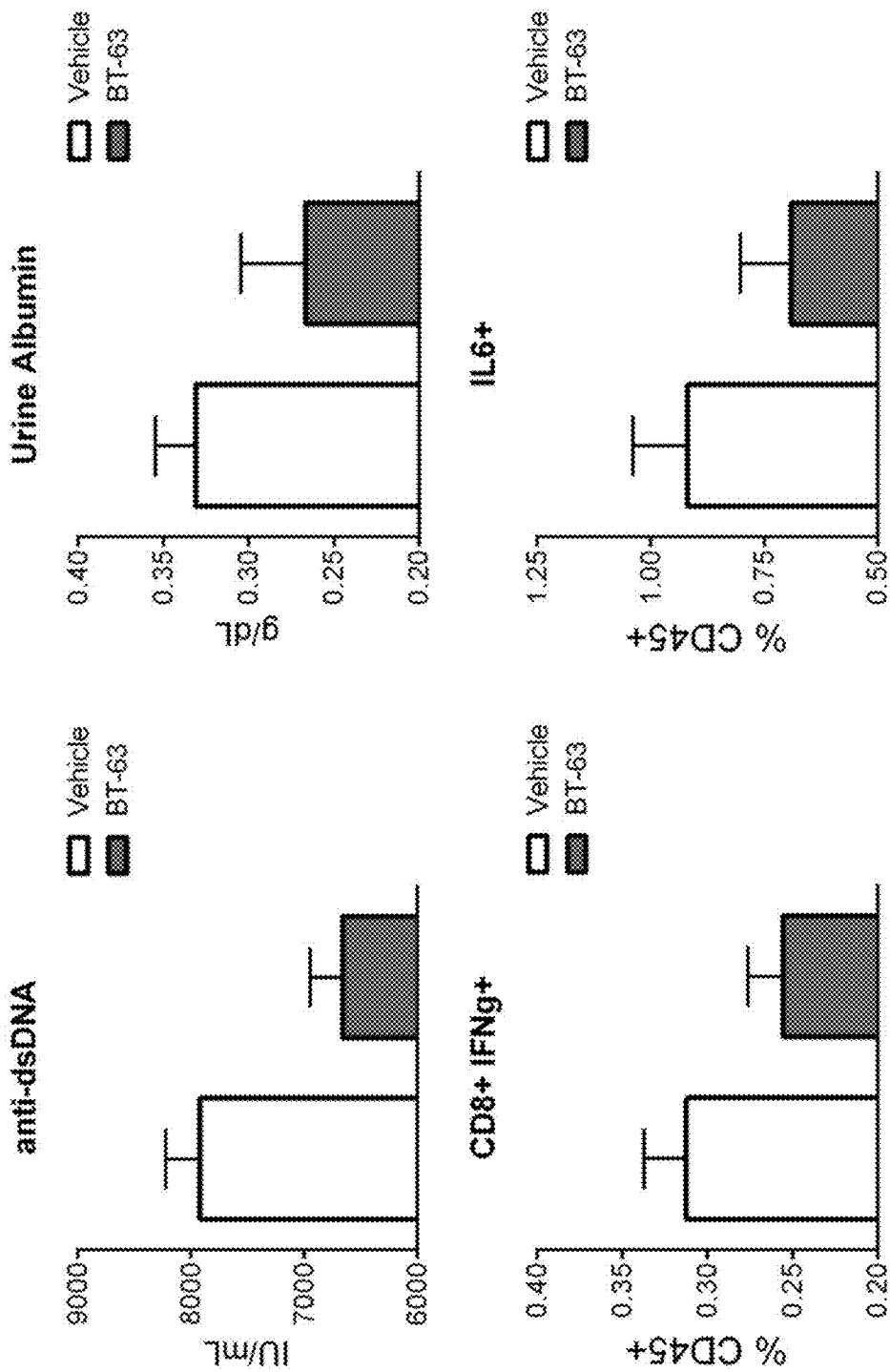
FIG. 8. Efficacy of BT-63 in a TLR7/9 induced model of SLE. Plasma antibodies to double-stranded DNA, urine albumin levels, spleen CD8+ IFNγ+ and IL6+ CD45+ cells after two weeks of oral treatment with vehicle or 20 mg/kg BT-63.

Oral BT-63 reduces the concentration of anti-dsDNA antibodies in plasma after 2 weeks of treatment and provides reduction of urine albumin content resulting in two benefits specific to the pathogenesis of SLE (FIG. 8). Immunological differences are present within the spleen in the form of reduced IFNγ+ CD8+ T cells and IL6+ cells indicating decreased inflammation.

Example 8. Use of BT-63 in a Chronic Model of IBD

Introduction

Crohn's disease and ulcerative colitis are chronic diseases with sporadic periods of unresolved inflammatory flares resulting in progressive damage to the intestinal mucosa.

The loss of Mdr1a in mice impairs the ability of epithelial cells to correctly process and efflux waste products leading to spontaneous colitis. The colitis in these mice is chronic and penetrates throughout the layers of the intestine. The Mdr1a−/− model is therefore an ideal model to test the chronic administration of a therapeutic for the induction and maintenance of decreased disease severity.

Unlike other genetic models of disease that can generate immunocompromised mice, Mdr1a−/− mice are immunocompetent, with the deletion instead impacting the cellular ability to efflux molecules and prevent cellular stress. The accumulation of waste and cellular by-products leads to a dysregulation of the epithelial cell lifecycle and increased secretion of inflammatory cytokines and chemokines. Thus, it provides a chronic and spontaneous onset of disease with primary initiating events occurring within the epithelium. Additionally, the MDR1 gene is an emerging risk allele for IBD and affect the responsiveness to glucocorticoid-based treatments. The ability of BT-63 to provide therapeutic efficacy in the absence of this gene is an important indication of robustness in the presence of genetic abnormalities and indicate an ability for human translation in a surgery-sparing context.

Methods

MDR1a−/− model. Mice deficient in MDR1a spontaneously develop colitis. MDR1a−/− began receiving BT-63 treatment (oral, 20 mg/kg) at 6 weeks of age and continued treatment until 10 weeks of age. Mice were weighed and scored weekly.

Treatment administration. BT-63 was prepared within a 0.5% methylcellulose (12-15 cP) solution. Dosage used was 20 mg/kg delivered once daily. Mice were weighed on a weekly basis to update dosage formulation. Dosage was calculated based off mean body weights for each gender. Oral dosage was delivered by orogastric gavage of dosage in 0.2 mL volume.

Flow Cytometry. Colons were collected into RPMI/FBS buffer containing collagenase (300U/mL) and DNase (50U/mL) for digestion. Tissues were digested for 60 minutes under stirring at 37° C. Resultant cellular suspensions were filtered through 100 μm strainers, centrifuged (300×g, 8 min), and washed in fresh RPMI. Following filtration of the resulting single cell suspensions, immune cells were purified by Percoll gradient of cell-containing 40% Percoll overlayed onto 70% Percoll solution. After centrifugation, interphase was collected and washed to obtain enriched colonic lamina propria cell fractions. Cells were labeled with mixtures of extracellular (CD45, CD3, CD4, CD8, CD19, NK1.1, CD25, F4/80, CD11b, Gr1, CX3CR1, CD64) and intracellular (Tbet, RORγT, FOXP3, IFNγ, IL17, IL10) antibodies in a sequential live staining in 96-well plates. Data was acquired using a FACS Celesta flow cytometer with FACSDiva software.

Results

Figure 9:
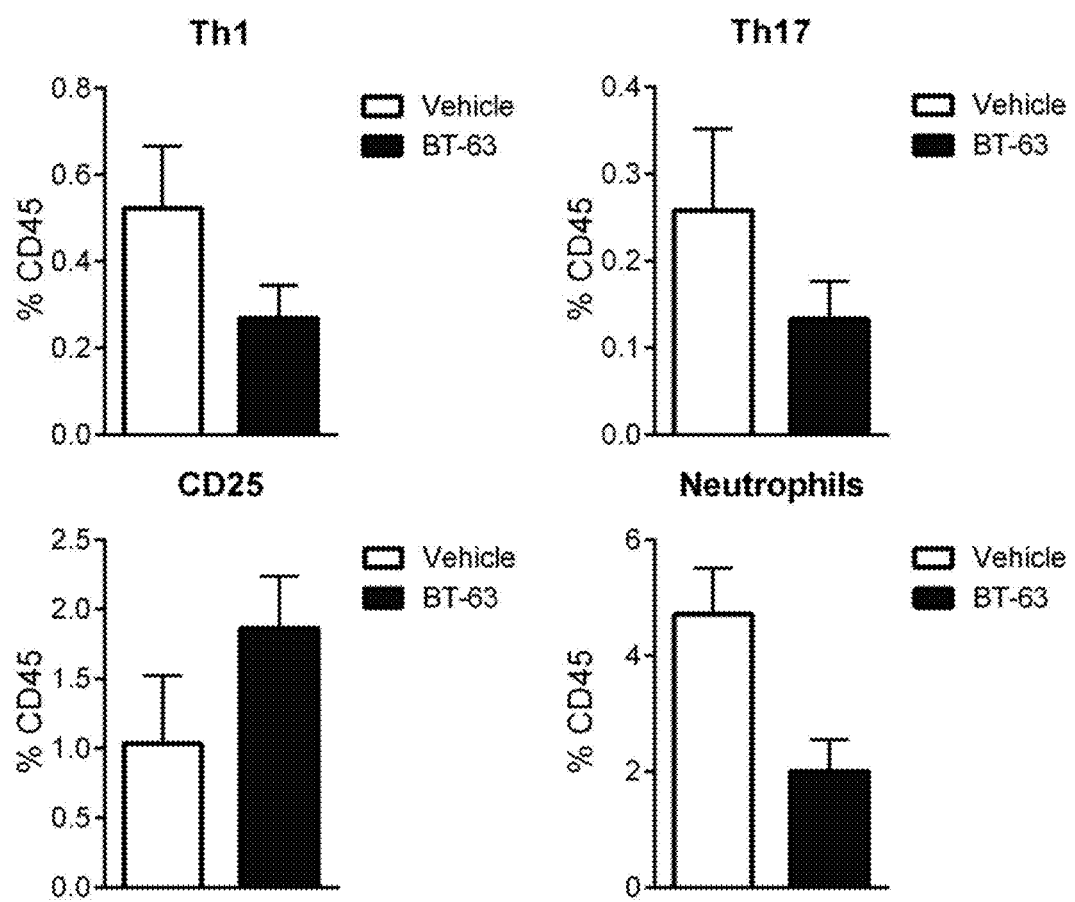
FIG. 9. Efficacy of BT-63 in an MDR1a−/− model of IBD. Colonic lamina propria Th1, Th17, CD25+ FOXP3+ CD4+ Tregs, and neutrophils after four weeks of oral treatment with vehicle or 20 mg/kg BT-63.
Figure 10:
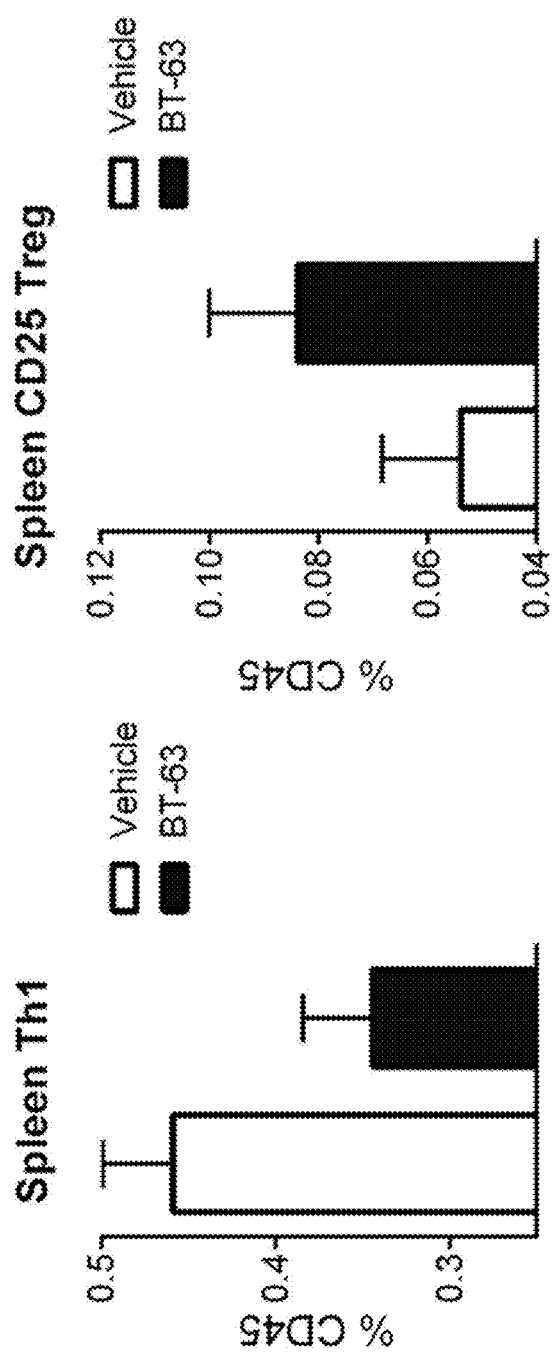
FIG. 10. Reduction of systemic inflammation in Mdr1a−/− mice treated with BT-63. Splenic Th1 and CD25+ Tregs after four weeks of oral treatment with vehicle or 20 mg/kg BT-63.

Oral BT-63 treatment decreases the disease activity of Mdr1a−/− mice. Disease activity in this model of colitis is a summarized score of the weight loss, presence and severity of rectal bleeding, fecal consistency, symptoms of pain and overall behavior of a mouse. BT-63 reduced disease activity throughout the course of the challenge with a maximal observed reduction by 90% in week four of treatment. Within the colonic lamina propria, BT-63 significantly alters the proportions of immune cells (FIG. 9). In particular, BT-63 reduces the proportions of Th1, Th17 and neutrophils, three main subsets of cells responsible for the inflammation in the colonic mucosa. Proportions of regulatory CD4+ CD25+ T cells were increased in the colon. Meanwhile, splenic Th1 cells were decreased and splenic CD25+ Tregs were increased after BT-63 treatment (FIG. 10). The efficacy of BT-63 in a highly translational mouse model of IBD highlights the use of BT-63 as an oral therapeutic for CD and UC.

Example 9. Efficacy of BT-63 in a Model Viral Infection

The activation of LANCL2 by specific ligands may modulate the immune response, prevent the entry or replication processes of the virus to reduce viral burden and promote the repair and homeostasis of the local tissue. To validate the efficacy of BT-63, we will use a mouse model of influenza virus infection.

Methods

Mouse model. Eight- to ten-week old wild type C57BL/6 mice were anesthetized by isoflurane inhalation. Mice were infected with influenza A (H1N1) intranasally at a challenge titer of 350 pfu/mouse [37]. Mice were treated daily with BT-63 at a dose of 20 mg/kg orally via gavage. Mice were weighed and scored daily over 12 days. Mice were euthanized at days 12 to measure immune responses by flow cytometry in the lungs.

Flow Cytometry. Lungs will be chopped into small pieces and collected into RPMI/FBS/CaCl$_2$) buffer containing collagenase (300U/mL) and DNase (50U/mL) for digestion. Tissues will be digested for 60 to 90 minutes under stirring at 37° C. Resultant cellular suspensions will be filtered through 100 µm strainers, centrifuged (300×g, 8 min), and washed in fresh RPMI. Red blood cells will be lysed by hypotonic lysis and removed by filtration. Cells will be washed and plated for flow cytometry staining. Cells will be labeled with mixtures of extracellular (CD45, CD3, CD4, CD8, CD19, NK1.1, CD25, F4/80, CD11b, CD11c, Gr1, CX3CR1, CD64, SiglecF, Ly6C) and intracellular (Tbet, RORγT, FOXP3, IFNγ, IL6, IL10, IFNb) antibodies in a sequential live staining in 96-well plates. Data will be acquired using a FACS Celesta flow cytometer with FACS-Diva software.

Results

Figure 11:
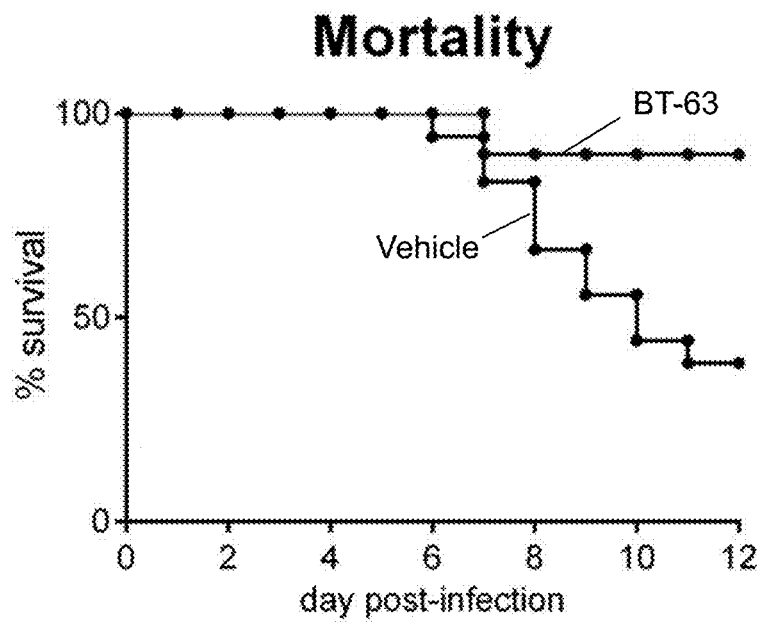
FIG. 11. Efficacy of BT-63 in a mouse model of influenza A virus infection. Survival and disease activity index over 12 days post-infection with influenza A (H1N1) with daily oral treatment with vehicle or 20 mg/kg BT-63.
Figure 11:
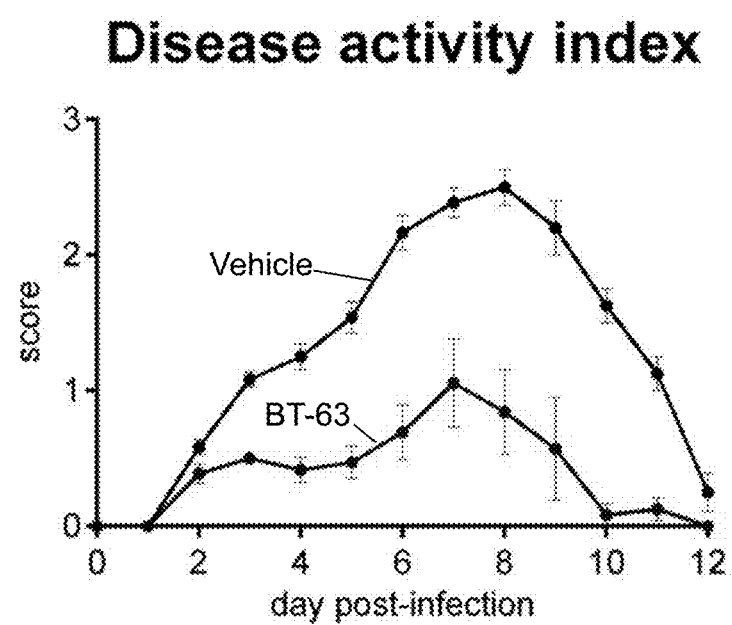
Figure 12:
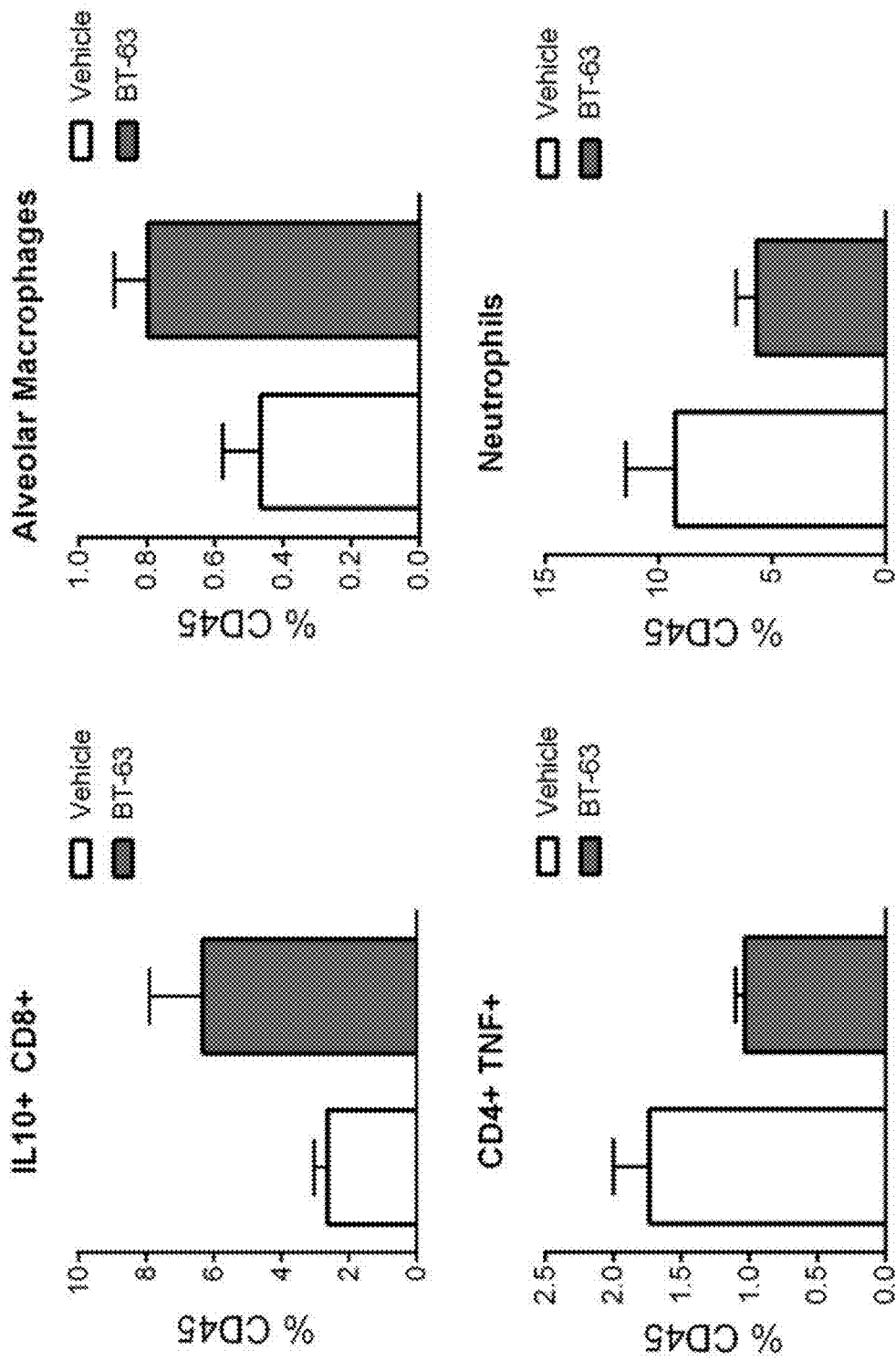
FIG. 12. Modulation of lung immune responses to influenza A infection by BT-63. Lung IL10+ CD8+ T cells, alveolar macrophages, CD4+ TNF+ T cells and neutrophils at day 12 post-infection with daily oral treatment with vehicle or 20 mg/kg BT-63.

Oral BT-63 protects against mortality and decreases the presentation of influenza-associated symptoms (FIG. 11). BT-63 significantly reduces disease activity index from day 3 post-infection through day 12 post-infection when compared to vehicle treated animals. Additionally, BT-63 increases survival by over 50% compared to vehicle. Immunologically, BT-63 increases IL10+ CD8+ T cells and alveolar macrophages at day 12 post-infection in the lung (FIG. 12). These two cell types have previously been characterized as important cells in the recovery from pulmonary viral infections. Further, BT-63 treated mice have decreased proportions of TNFα+ CD4+ T cells and neutrophils in the lungs, cell types associated with tissue damage. Together, the data confirms the protective effects of BT-63 in viral infections.

Example 10. Ex Vivo Treatment CD4+ T Cells for Treatment of Inflammatory Disease BT-63 through immunometabolic signaling changes the phenotypic profile of cells in vitro and immune responses in vivo. In particular, BT-63 shapes CD4+ T cells to increase expression of FOXP3, increase suppressive capacity, and increase stability of these regulatory cells in inflammatory conditions. Adoptive transfer of cells treated ex vivo with BT-63 is therefore beneficial in treating inflammatory diseases and disorders with inadequate CD4+ T cell responses, such as inflammatory bowel disease, graft versus host disease, and others described herein.

Methods

Naïve CD4+ T cells can be isolated from the spleens of mice by magnetic sorting. The isolated cells can be incubated in anti-CD3/anti-CD28 coated 96 well plates in Treg differentiation media. The Treg differentiation media can be Iscove's Modified Dulbecco's Medium (IMDM) media (ThermoFisher Scientific) supplemented with fetal bovine serum, HEPES, penicillin/streptomycin, L-glutamine, and differentiation agents. The Treg differentiation agents can be 10 nM all-trans-retinoic acid and 5 ng/mL TGF-β. Additional experiments can be conducted comparing differentiation in the Treg differentiation media with and without the addition of 10 ng/mL TL-2 or IL-12. Cells can be incubated with vehicle, 10 nM, or 100 nM BT-63 in differentiation media for 48 hours prior to assay. Prior to assay, cells can be stimulated with PMA and ionomycin for 6 hours.

In transfer experiments, donor spleens can be crushed and enriched for CD4+ fraction by magnetic sorting. CD4+ CD45RB$^{hi}$CD25− (Teff) and CD4+ CD45RB$^{lo}$CD25+ (Treg$_g$) cells can be sorted by a FACSAria cell sorter. Isolated Tregs can be cultured for 12 h in the presence of vehicle or BT-63 (100 nM). Isolated Teff can be cultured for 12 h in vehicle. Based on indicated experimental group, Rag2−/− recipient mice can receive 4×10$^5$ Teff and 1×10$^5$ Treg cells from vehicle or BT-63 treated groups by intraperitoneal injection. Mice can be weighed and scored weekly until euthanasia at 5 weeks post-transfer.

Colonic lamina propria lymphocytes and cultured cells can be plated in 96 well plates (6×10$^5$ cells/well) and processed for immunophenotyping by flow cytometry as previously described. Briefly, cells can be incubated with fluorochrome conjugated antibodies to extracellular markers: CD45, CD4, CD3, CD25, CD8. Samples needing a secondary staining can be incubated with secondary antibodies, or streptavidin-conjugated fluorochrome. The samples can then be fixed and permeabilized. Cells can be incubated with antibodies to intracellular markers: Tbet, IFN, IL10, FOXP3, IL17, RORγT. Data can be acquired with a BD FACS Celesta flow cytometer and analyzed using FACS Diva software (BD Pharmingen).

Results

With the importance of CD25+ FOXP3+ regulatory CD4+ T cells to the efficacy of BT-63, we aim to confirm the direct effect of BT-63 on their differentiation and ability to retain phenotype in inflammatory conditions. Naïve CD4+ T cells can be differentiated into Tregs in vitro in the presence or absence of IL-2 according to the methods described above. We predict BT-63 treatment (100 nM) will significantly increase the establishment of a CD25+ FOXP3+ subtype in the absence of IL-2, a difference that will further be accentuated by the addition of IL-2. We predict that at concentrations as low as 10 nM, BT-63 will induce significantly more CD25+ FOXP3+ cells in the presence of IL-2. We predict only low levels of a mixed CD25+ Tbet+ subtype will be observed under these differentiation conditions, and this will not be statistically altered by BT-63. We predict BT-63 will retain significantly higher levels of CD25+ FOXP3+ cells in IL-12-treated samples. This will contrast with the suppression of CD25+ FOXP3+ cells in IL-12-treated samples in the absence of BT-63. The addition of IL-12 will also induce an increase in CD25+ Tbet+ cells in all groups, though BT-63 will provide a dose-dependent protection against this mixed subset.

To identify signaling pathways modulated by BT-63 in vivo, we will isolate colonic CD4+ T cells from vehicle- and BT-63-treated Mdr1a−/− mice at presentation of colitis at 10 weeks of age. In CD4+ T cells, oral BT-63 treatment will result in significantly higher expression of Stat5a and Foxo1, two members of the IL-2 signaling pathway. Meanwhile, expression of Pten and Phlpp1 will increase. In vitro, STAT5a will be phosphorylated in a greater ratio in BT-63-treated samples in the base Treg differentiation media and also in the Treg differentiation media supplemented with either IL-2 or IL-12. FOXO1 will similarly be affected in both the base Treg differentiation media and the Treg differentiation media containing IL-2, but not in the Treg differentiation media containing IL-12. Cells will also be differentiated in the presence of inhibitors for PTEN (SF1670) or STAT5 (STAT5i). In the Treg differentiation media containing both IL-2 or IL-12, the addition of STAT5i will prevent the effects of BT-63 on CD25+ FOXP3+ and CD25+ Tbet+ cells. In contrast, SF1670 only will prevent effects of BT-63 on CD25+ Tbet+ cells in IL-2 containing media.

Rag2−/− mice lack mature T and B lymphocytes. Therefore, these mice fail to develop mechanisms of self-tolerance, microbial homeostasis, and overall immunoregulation. Transfer of naive CD4+ T cells into Rag2−/− mice induces intestinal inflammation resulting from the absence of these mechanisms through in vivo expansion of the transferred cells and differentiation into inflammatory phenotypes in a manner similar to those experienced in active inflammatory autoimmune diseases including but not limited to inflammatory bowel disease. We hypothesize that the transfer of regulatory cells treated ex vivo with BT-63 will confer mechanisms of homeostasis and immunoregulation to recipient animals.

The adoptive transfer of Tregs treated ex vivo with BT-63 (100 nM) will decrease overall disease severity and will provide maintenance of immune benefits up to the tested limit duration of 5 weeks post-transfer. In addition to overall improvement of disease, ex vivo treatment of Tregs with BT-63 will result in changed phenotypes of colonic lamina propria cells. In BT-63-treated Treg groups, IFNγ-producing and IL-17+ RORγT+ CD4+ T cells will reduce. Meanwhile, CD25+ Tregs will increased, indicating an increased stability and increased ability to serve as a founder population of regulatory cells. Further, interaction with the IL-2/STAT5 signaling axis will promote important changes in the cytokine and chemokine microenvironment that amplify the effects of transferred cells.

These results will show that the effects of BT-63 on immune cells when administered in vivo will be replicated when treating immune cells ex vivo. We predict that administering the prepared cells of the invention to an animal will be effective in treating any of the conditions described herein beyond inflammatory diseases such as IBD.

Example 11. Use of BT-63 in a Genetic Mouse Model of SLE

Introduction

Systemic lupus erythematosus (SLE) is a systemic autoimmune disease that can cause damage to kidneys, cardiovasculature, and joints. SLE is a result of a complex interaction of genetic factors that results in immunological disease manifested primarily through a generation of autoantibodies. One preclinical model aimed at captured these complex factors is the NZB/W F1 model. The F1 cross of NZB and NZW mice results in mice with autoimmunity of progressive severity. This autoimmunity shares many common features with human SLE including the generation of anti-nuclear antibodies, kidney damage and elevated type I interferon responses.

Methods

NZB/W F1 model. Twenty-four-week-old, female NZB/W F1 mice were randomized into vehicle or BT-63-treated arms based on baseline urine protein levels (n=10). BT-63 was orally administered daily at 20 mg/kg for 12 weeks. Mice were weighed on a weekly basis to update dosage formulation. Dosage was calculated based off mean body weights.

Immunological analysis. Blood was collected by cardiac puncture into EDTA tube. Plasma was separated following centrifugation and assayed by ELISA for anti-dsDNA antibodies and IFN-α. Urine was collected to assay for protein content to test for kidney function. Spleens were excised, crushed and filtered to provide a cellular suspension. Red blood cells were lysed. Cells were labeled with mixtures of extracellular (CD45, CD3, CD4, CD8, CD19, CD138, CD25, MHCII, CD11b, CD11c, CXCR3, IgD, IgM) and intracellular (BCL6, FOXP3, IL21, IL6, IL10) antibodies in a sequential live staining in 96-well plates in preparation for flow cytometry. Data was captured on a BD FACS Celesta and analyzed using FacsDiva.

Results

Figure 13:
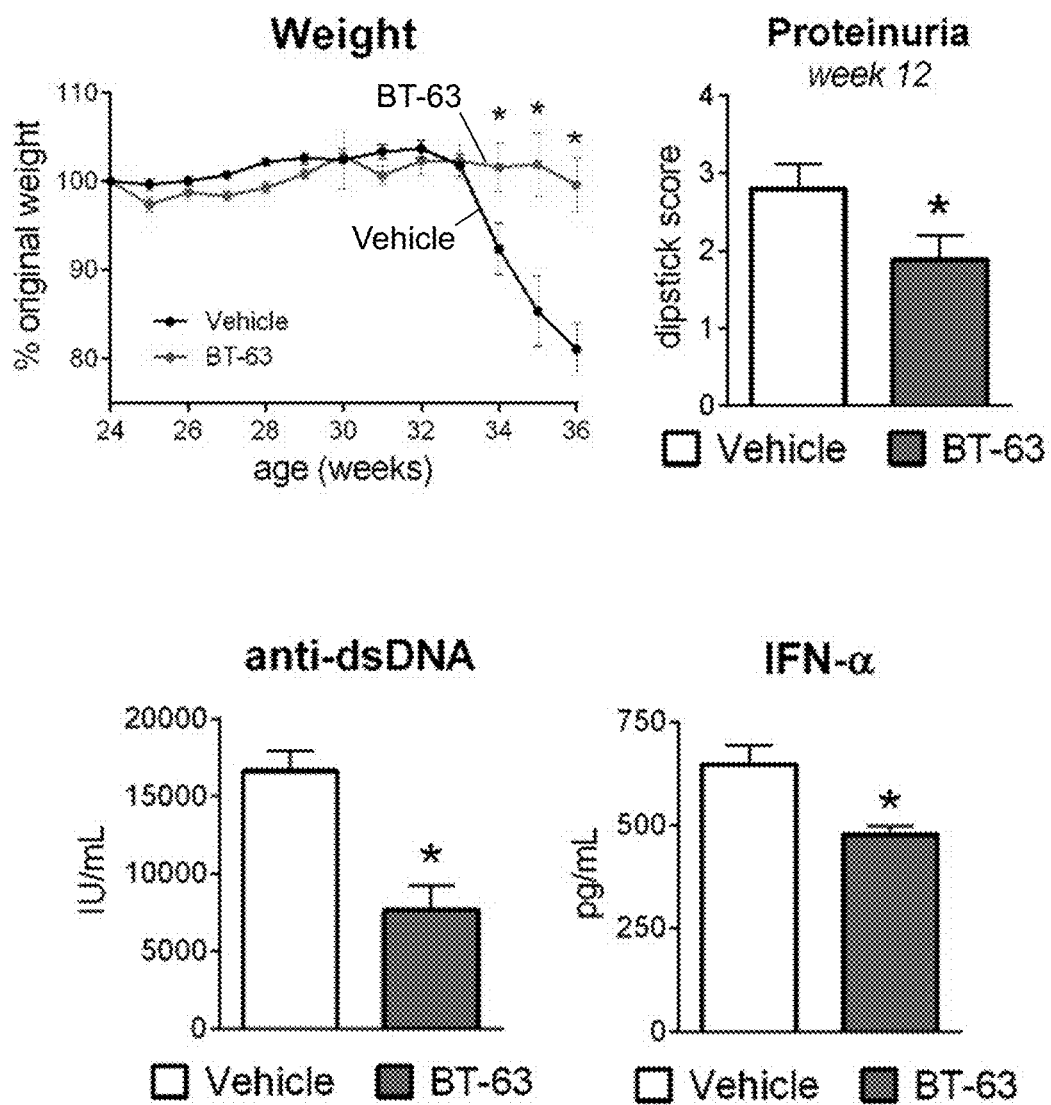
FIG. 13. Efficacy of BT-63 in an NZB/W F1 model of SLE. Body weight changes from baseline over 12 weeks of vehicle or 20 mg/kg BT-63 treatment. Urine protein score, plasma anti-dsDNA antibodies and plasma IFN-α concentration after 12 weeks of oral treatment with vehicle or BT-63 (20 mg/kg).
Figure 14:
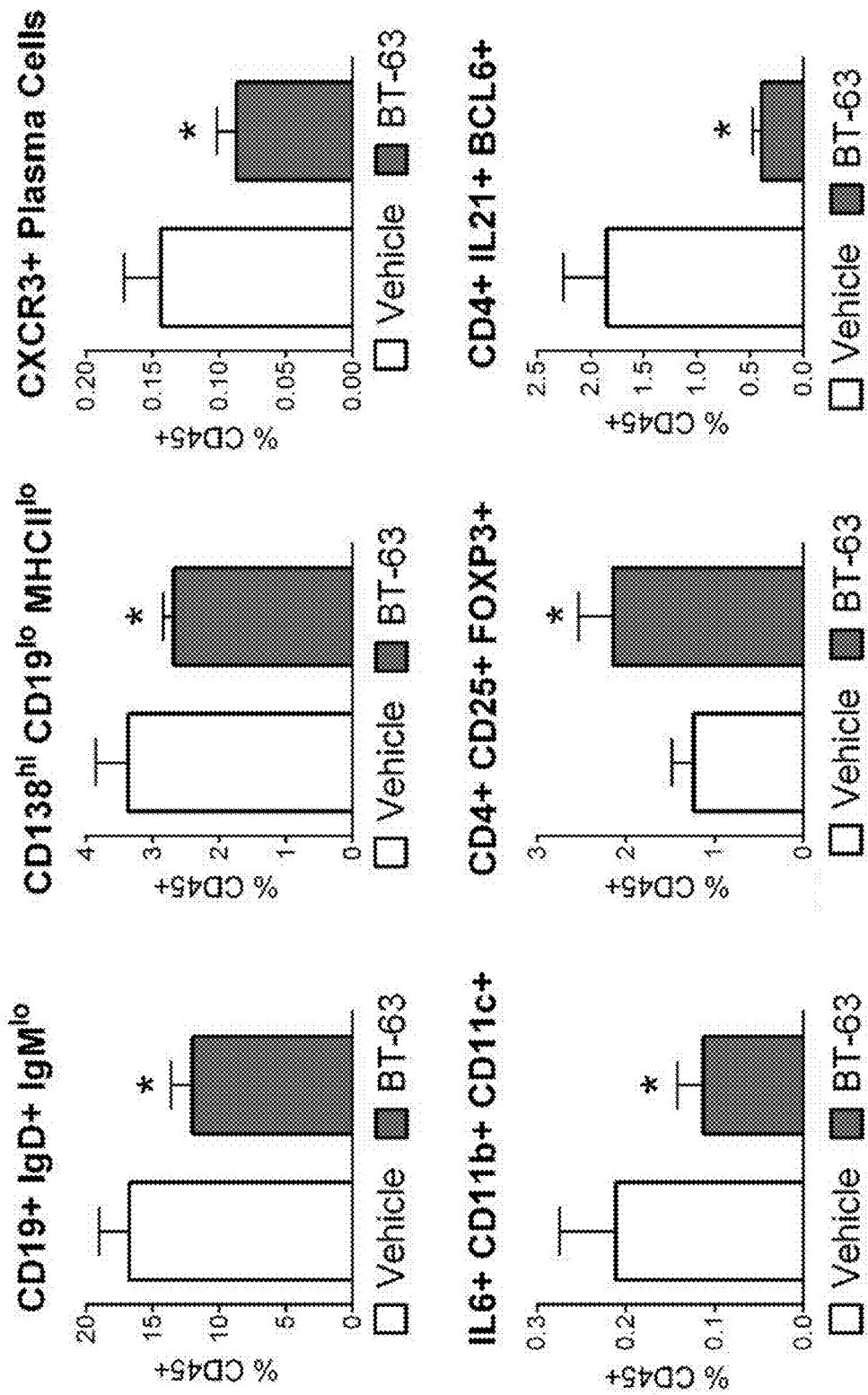
FIG. 14. Immunological responses to BT-63 in an NZB/W F1 model. Splenic CD19+ IgD+ IgM$^{lo}$ follicular B cells, CD138$^{hi}$ CD19$^{lo}$ MHCII$^{lo}$ plasma cells, CXCR3+ plasma cells, IL6+ CD11b+ CD11c+ myeloid cells, CD4+ CD25+ FOXP3+ Tregs, CD4+IL21+ BCL6+ follicular helper T cells after 12 weeks of oral treatment with vehicle or BT-63 (20 mg/kg).

Orally administered BT-63 protected mice from weight loss and prevented worsening of proteinuria score from baseline (FIG. 13). BT-63-treated mice had reduced levels of plasma anti-dsDNA and IFN-α levels at 36 weeks of age (12 weeks of treatment). BT-63 treatment resulted in moderate reduction of follicular B cells and plasma cells in the spleen, in particular CXCR3+ plasma cells, a main pathogenic subset in lupus. However, greater reductions in IL6+ myeloid cells, CD25+ FOXP3+ regulatory CD4+ T cells and IL21+ BCL6+ follicular helper T cells were observed relative to vehicle (FIG. 14).

Example 12. Use of BT-104-B in a Model of Nonalcoholic Steatohepatitis (NASH)

Introduction

NASH is a progressive chronic liver disease that afflicts over 140 million people worldwide with total health care costs exceeding $8 billion annually in the US alone. No current therapeutics are approved for NASH. While a reversible condition, failure to effectively treat NASH results in higher risk of hepatocellular carcinoma, liver failure, and cardiac death. With a multitude of hepatic and extrahepatic factors, NASH is a complex disease. Yet, many therapeutics in development fail to address all three main areas of dysregulation, comprised of metabolic, inflammatory, and fibrotic factors.

Methods

WD-induced model. C57BL/6 mice were administered bi-weekly intraperitoneal injections of 0.5 μL/g $CCl_4$ to induce steatohepatitis for 4 weeks. Mice were treated daily, in a therapeutic manner after 2 weeks of injections. Treatment with BT-104-B (20 mg/kg) or vehicle control occurred by oral gavage. Dosage was calculated based off mean body weights.

Analysis. Livers were excised and weighed. Sections of livers were excised and stored in buffered formalin for Sirius red staining or snap frozen for assessment of fibrosis. Severity of fibrosis was assessed by scoring of Sirius red stained liver by microscopic examination.

Results

Figure 16A:
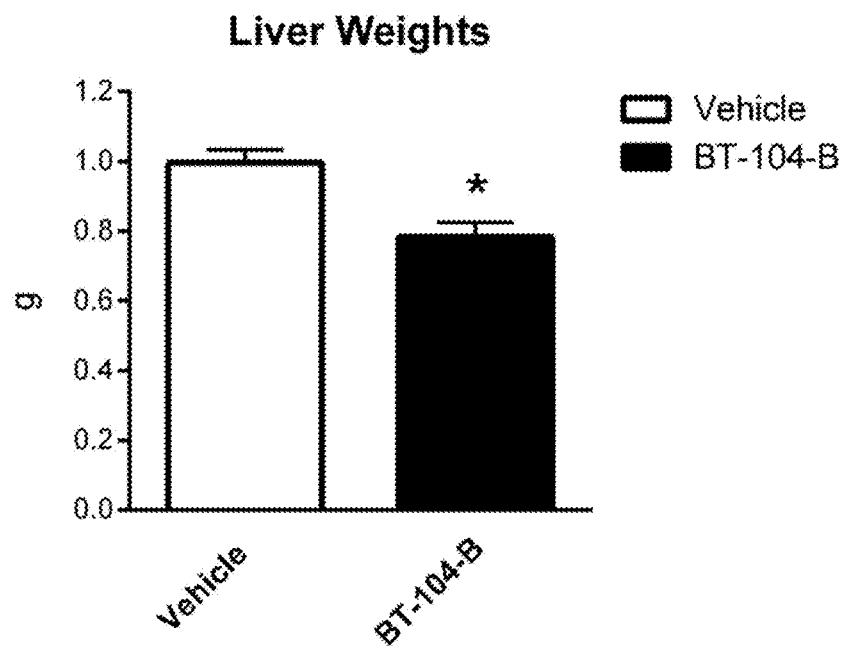
FIGS. 16A and 16B. In vivo validation of BT-104-B efficacy in a $CCl_4$ model of nonalcoholic steatohepatitis. Liver weight (FIG. 16A) and fibrosis score (FIG. 16B) after 4 weeks of bi-weekly carbon tetrachloride injections in vehicle and BT-104-B (20 mg/kg) treated mice. Statistical significance (P<0.05) is marked by asterisks.
Figure 16B:
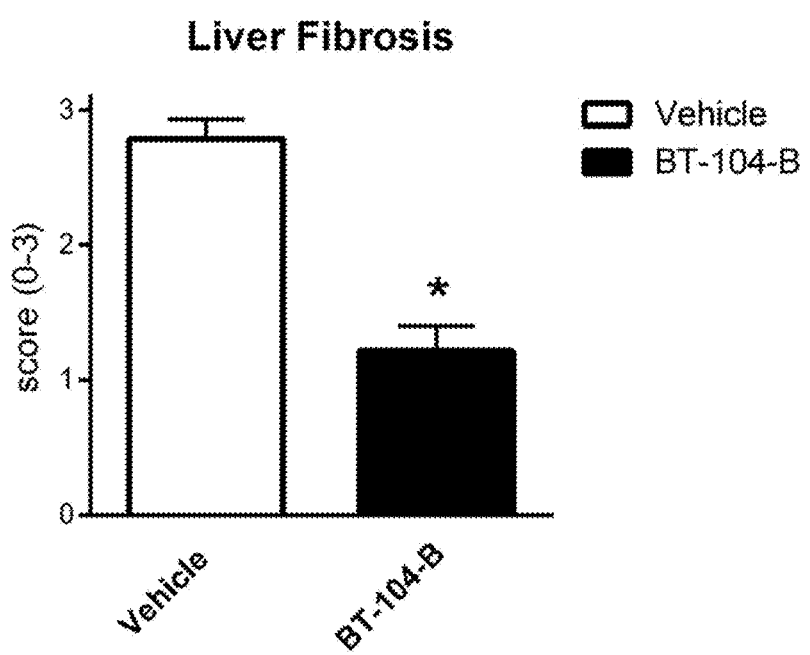

Oral BT-104-B reduced liver weights (FIG. 16A) and fibrotic scoring (FIG. 16B) after 2 weeks of treatment, indicating the ability to improve liver inflammation and fibrosis in the context of NASH.

Example 13. Use of BT-104-B in a Mouse Model of Rheumatoid Arthritis

Introduction

Rheumatoid arthritis (RA) causes severe inflammation of joints leading to loss of mobility and intense pain. The underlying immunology of synovial inflammation is complex, involving the interplay of myeloid cells, T cells, fibroblasts and other structural cells of the synovium. High expression of TNF and IL-6 are central to the pathogenesis of RA, with additional contributions by IL-1β, IL-12, IL-17, IL-21, IL-23, MCP1, and TGF-β. Together these cytokines can lead to leukocytic recruitment, bone remodeling, pannus formation, oxidative stress and hyperplasia of the joint lining.

Methods

Models. Six-week-old C57Bl/6 mice were immunized with 200 μg of chicken collagen emulsified in complete Freund's adjuvant by intradermal injections at the base of the tail. Mice were treated with 20 mg/kg of BT-104-B or vehicle, daily for four weeks.

Immunological analysis. Spleens were excised from mice. Tissues were crushed and filtered to provide a cellular suspension. Red blood cells were lysed. Cells were labeled with mixtures of extracellular (CD45, CD3, CD4, CD8, CD11b, CD11c) and intracellular (IFNγ, IL17, TNF) antibodies in a sequential live staining in 96-well plates in preparation for flow cytometry. Data was captured on a BD FACS Celesta and analyzed using FACSDiva.

Results

Figures 17A, 17B, 17C:
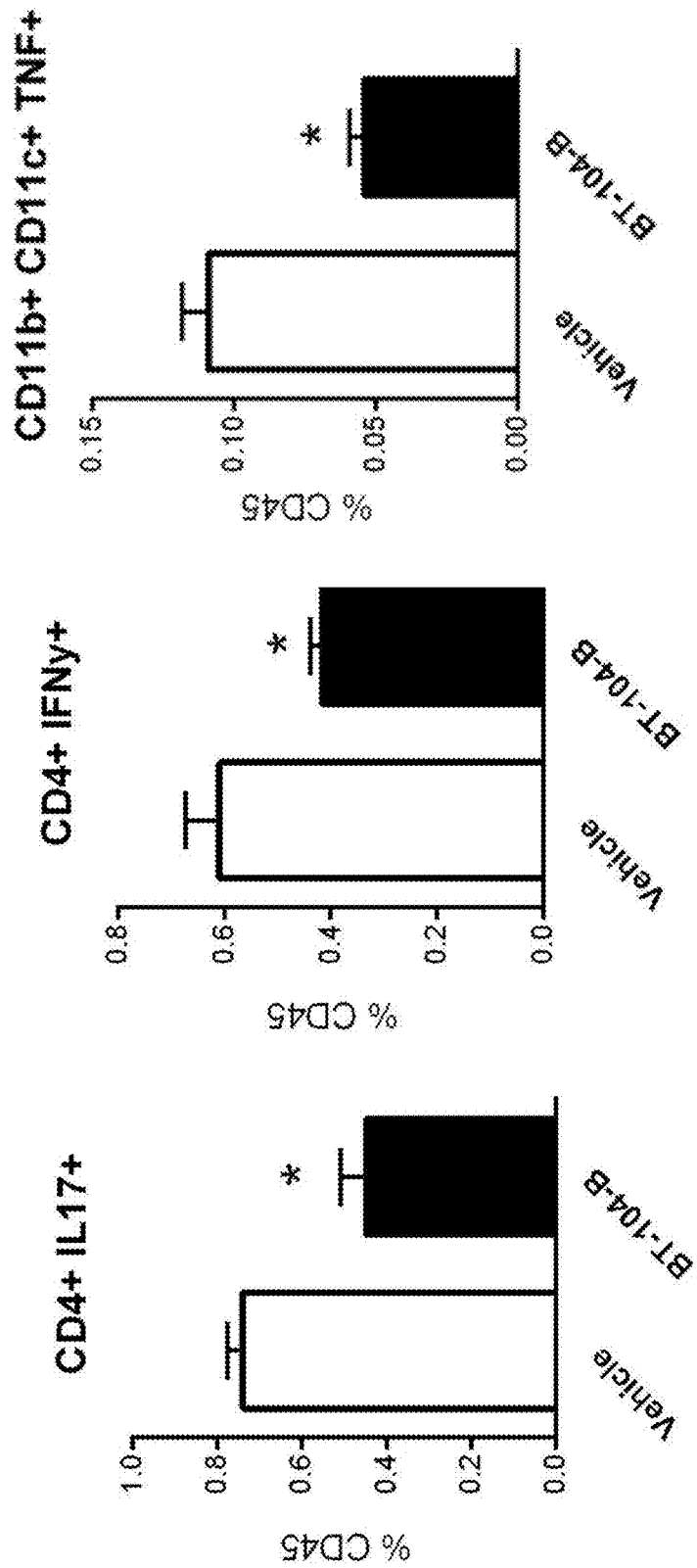
FIGS. 17A-17C. In vivo validation of BT-104-B efficacy in a collagen induced model of arthritis. Percentages of IL17+(FIG. 17A), IFNγ+ CD4+ T cells (FIG. 17B), and TNF+ CD11b+ CD11c+ myeloid cells (FIG. 17C) in the spleens of collagen induced arthritis mice after 4 weeks of daily oral treatment with vehicle or BT-104-B (20 mg/kg). Statistical significance (P<0.05) is marked by asterisks.

Oral BT-104-B significantly reduced the proportion of IL-17+ CD4+ T cells (FIG. 17A), IFNγ+ CD4+ T cells (FIG. 17B), and TNF+ CD11b+ CD11c+ myeloid cells (FIG. 17C) in the spleens of mice with collagen induced arthritis in comparison to vehicle treated controls. This indicates the ability to BT-104-B and related compounds in the treatment of rheumatoid arthritis.

Example 14. Use of BT-104-B in a Genetic Mouse Model of SLE

Introduction

Systemic lupus erythematosus (SLE) is a systemic autoimmune disease that can cause damage to kidneys, cardiovasculature, and joints. SLE is a result of a complex interaction of genetic factors that results in immunological disease manifested primarily through a generation of auto-antibodies. One preclinical model aimed at captured these complex factors is the NZB/W F1 model. The F1 cross of NZB and NZW mice results in mice with autoimmunity of progressive severity. This autoimmunity shares many common features with human SLE including the generation of anti-nuclear antibodies, kidney damage, and elevated type I interferon responses.

Methods

NZB/W F1 model. Twenty-four-week-old, female NZB/W F1 mice were randomized into vehicle or BT-104-B treated arms based on baseline urine protein levels. BT-104-B was administered daily at 20 mg/kg for 12 weeks. Mice were weighed on a weekly basis to update dosage formulation. Dosage was calculated based off mean body weights.

Immunological analysis. Spleens were excised, crushed and filtered to provide a cellular suspension. Red blood cells were lysed. Cells were labeled with mixtures of extracellular (CD45, CD3, CD4, CD8, CD25) and intracellular (IL21, IL17, FOXP3) antibodies in a sequential live staining in 96-well plates in preparation for flow cytometry. Data was captured on a BD FACS Celesta and analyzed using FACSDiva.

Results

Oral BT-104-B significantly reduced the proportion of IL-17+ CD4+ T cells (FIG. 18A) and IL21+ CD4+ T cells (FIG. 18B) while significantly increasing the proportion of CD25+ FOXP3+ CD4+ T cells (FIG. 18C) in the spleens of NZB/W F1 mice in comparison to vehicle treated controls. This indicates the ability to BT-104-B and related compounds in the treatment of SLE.

What is claimed is:

1. A compound of formula Z—Y-Q-Y' or a pharmaceutically acceptable salt or ester thereof, wherein:
Z—Y-Q-Y' is:

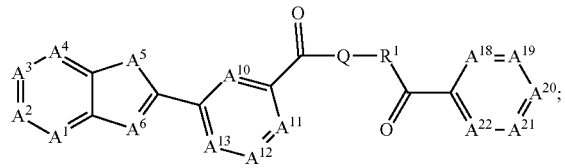

Q is piperazine-1,4-diyl or substituted piperazine-1,4-diyl;
$A^1$, $A^2$, $A^3$, $A^{11}$, $A^{12}$, $A^{13}$, $A^{18}$, $A^{20}$, and $A^{22}$ are each independently $C(R^3)$;
$A^4$, $A^6$, $A^{10}$, $A^{19}$, and $A^{21}$ are each independently $C(R^3)$ or N;
$A^5$ is $N(R^3)$, $C(R^3)_2$, O, or S;
$R^1$ is optionally substituted alkylene optionally containing one or two heteroatom(s); and
$R^3$ in each instance is independently a hydrogen atom, a halogen atom, optionally substituted alkyl, optionally substituted alkenyl, optionally substituted alkynyl, optionally substituted cycloalkyl, optionally substituted cycloalkenyl, hydroxy, carboxy, optionally substituted alkyloxy, optionally substituted alkenyloxy, optionally substituted alkynyloxy, optionally substituted cycloalkyloxy, optionally substituted cycloalkenyloxy, mercapto, optionally substituted alkylthio, optionally substituted alkenylthio, optionally substituted alkynylthio, optionally substituted alkylsulfinyl, optionally substituted alkylsulfonyl, optionally substituted alkylsulfonyloxy, optionally substituted cycloalkylthio, optionally substituted cycloalkylsulfinyl, optionally substituted cycloalkylsulfonyl, optionally substituted cycloalkylsulfonyloxy, optionally substituted cycloalkenylthio, optionally substituted cycloalkenylsulfinyl, optionally substituted cycloalkenylsulfonyl, optionally substituted cycloalkenylsulfonyloxy, optionally substituted amino, acyl, optionally substituted alkyloxycarbonyl, optionally substituted alkenyloxycarbonyl, optionally substituted alkynyloxycarbonyl, optionally substituted aryloxycarbonyl, optionally substituted carbamoyl, optionally substituted sulfamoyl, cyano, nitro, optionally substituted aryl, optionally substituted aryloxy, optionally substituted arylthio, optionally substituted arylsulfinyl, optionally substituted arylsulfonyl, optionally substituted arylsulfonyloxy, optionally substituted heteroaryl, optionally substituted heteroaryloxy, optionally substituted heteroarylthio, optionally substituted heteroarylsulfinyl, optionally substituted heteroarylsulfonyl, optionally substituted heteroarylsulfonyloxy, or an optionally substituted non-aromatic heterocyclic group;
each optionally substituted alkyl, optionally substituted alkyloxy, optionally substituted alkylthio, optionally substituted alkylsulfinyl, optionally substituted alkylsulfonyl, optionally substituted alkylsulfonyloxy, and optionally substituted alkyloxycarbonyl, when substituted, is independently substituted with one to three substituent(s) selected from the group consisting of cycloalkyl, alkylene optionally containing one or two heteroatom(s), hydroxy, oxo, alkyloxy optionally substituted with a substituent group A at one to three position(s), mercapto, alkylthio, a halogen atom, nitro, cyano, carboxy, alkyloxycarbonyl, optionally substituted amino, optionally substituted carbamoyl, acyl, aryl optionally substituted with a substituent group B at one to three position(s), heteroaryl optionally substituted with a substituent group C at one to three position(s), an optionally substituted non-aromatic heterocyclic ring group optionally substituted with a substituent group C at one to three position(s), aryloxy optionally substituted with a substituent group B at one to three position(s), and alkylsulfonyl;

each optionally substituted alkenyl, optionally substituted alkynyl, optionally substituted alkenyloxy, optionally substituted alkynyloxy, optionally substituted alkenylthio, optionally substituted alkynylthio, optionally substituted alkenyloxycarbonyl, optionally substituted alkynyloxycarbonyl, optionally substituted cycloalkyl, optionally substituted cycloalkenyl, optionally substituted cycloalkyloxy, optionally substituted cycloalkenyloxy, optionally substituted cycloalkylthio, optionally substituted cycloalkenylthio, optionally substituted cycloalkylsulfinyl, optionally substituted cycloalkenylsulfinyl, optionally substituted cycloalkylsulfonyl, optionally substituted cycloalkenylsulfonyl, optionally substituted cycloalkylsulfonyloxy, optionally substituted cycloalkenylsulfonyloxy, and optionally substituted alkylene optionally containing one or two heteroatom(s), when substituted, is independently substituted with one or more substituent(s) selected from the group consisting of alkyl optionally substituted with a substituent group D at one to three position(s), cycloalkyl, hydroxy, oxo, alkyloxy optionally substituted with a substituent group A at one to three position(s), mercapto, alkylthio, a halogen atom, nitro, cyano, carboxy, alkyloxycarbonyl, optionally substituted amino, optionally substituted carbamoyl, acyl, acyloxy, aryl optionally substituted with a substituent group B at one to three position(s), heteroaryl optionally substituted with a substituent group C at one to three position(s), non-aromatic heterocyclic group optionally substituted with a substituent group C at one to three position(s), aryloxy optionally substituted with a substituent group C at one to three position(s), and alkylsulfonyl;

the substituted piperazine-1,4-diyl and each optionally substituted aryl, optionally substituted aryloxy, optionally substituted aryloxycarbonyl, optionally substituted arylthio, optionally substituted arylsulfinyl, optionally substituted arylsulfonyl, optionally substituted arylsulfonyloxy, optionally substituted heteroaryl, optionally substituted heteroaryloxy, optionally substituted heteroarylthio, optionally substituted heteroarylsulfinyl, optionally substituted heteroarylsulfonyl, optionally substituted heteroarylsulfonyloxy, optionally substituted non-aromatic heterocyclic group, and optionally substituted piperazine-1,4-diyl, when substituted, are each independently substituted with one or more substituent(s) selected from the group consisting of alkyl optionally substituted with a substituent group D at one to three position(s), oxo, cycloalkyl, alkenyl, alkynyl, hydroxy, alkyloxy optionally substituted with a substituent group A at one to three position(s), aryloxy optionally substituted with a substituent group B at one to three position(s), mercapto, alkylthio, a halogen atom, nitro, cyano, carboxy, alkyloxycarbonyl, acyl, alkylsulfonyl, optionally substituted amino, optionally substituted carbamoyl, aryl optionally substituted with a substituent group B at one to three position(s), heteroaryl optionally substituted with a substituent group C at one to three position(s), and non-aromatic heterocyclic group optionally substituted with a substituent group C at one to three position(s);

each optionally substituted amino, optionally substituted carbamoyl, and optionally substituted sulfamoyl, when substituted, is independently substituted with one or two substituent(s) selected from the group consisting of alkyl, alkenyl, alkynyl, cycloalkyl, cycloalkynyl, aryl, heteroaryl, acyl, alkyloxycarbonyl, alkenyloxycarbonyl, alkynyloxycarbonyl, alkyl sulfonyl, alkenylsulfonyl, alkynylsulfonyl, arylsulfonyl, and heteroarylsulfonyl;

each substituent group A is independently selected from the group consisting of a halogen atom and phenyl optionally substituted with one to three substituent(s) selected from substituent group B;

each substituent group B is independently selected from the group consisting of a halogen atom, alkyl, alkyloxy, cyano, and nitro;

each substituent group C is independently selected from the group consisting of a halogen atom and alkyl; and each substituent group D is independently selected from the group consisting of a halogen atom and alkyloxy.

2. The compound of claim 1, wherein:

$A^5$ is $N(R^3)$; and $A^6$ is N.

3. The compound of claim 1, wherein R is optionally substituted alkylene, which, when substituted, is substituted with one or more substituent(s) selected from the group consisting of alkyl optionally substituted with a substituent group D at one to three position(s), cycloalkyl, hydroxy, oxo, alkyloxy optionally substituted with a substituent group A at one to three position(s), mercapto, alkylthio, a halogen atom, nitro, cyano, carboxy, alkyloxycarbonyl, optionally substituted amino, optionally substituted carbamoyl, acyl, acyloxy, aryl optionally substituted with a substituent group B at one to three position(s), heteroaryl optionally substituted with a substituent group C at one to three position(s), non-aromatic heterocyclic group optionally substituted with a substituent group C at one to three position(s), aryloxy optionally substituted with a substituent group C at one to three position(s), and alkylsulfonyl.

4. The compound of claim 1, wherein:

$A^4$ is $C(R^3)$;

$A^5$ is $N(R^3)$;

$A^6$ and $A^{10}$ are N; and $R^1$ is optionally substituted alkylene, which, when substituted, is substituted with one or more substituent(s) selected from the group consisting of alkyl optionally substituted with a substituent group D at one to three position(s), cycloalkyl, hydroxy, oxo, alkyloxy optionally substituted with a substituent group A at one to three position(s), mercapto, alkylthio, a halogen atom, nitro, cyano, carboxy, alkyloxycarbonyl, optionally substituted amino, optionally substituted carbamoyl, acyl, acyloxy, aryl optionally substituted with a substituent group B at one to three position(s), heteroaryl optionally substituted with a substituent group C at one to three position(s), non-aromatic heterocyclic group optionally substituted with a substituent group C at one to three position(s), aryloxy optionally substituted with a substituent group C at one to three position(s), and alkylsulfonyl.

5. The compound of claim 4, wherein $R^1$ is optionally substituted C1, C2, or C3 alkylene, which, when substituted, is substituted with one or more substituent(s) selected from the group consisting of alkyl optionally substituted with a substituent group D at one to three position(s), cycloalkyl, hydroxy, oxo, alkyloxy optionally substituted with a substituent group A at one to three position(s), mercapto, alkylthio, a halogen atom, nitro, cyano, carboxy, alkyloxycarbonyl, optionally substituted amino, optionally substituted carbamoyl, acyl, acyloxy, aryl optionally substituted with a substituent group B at one to three position(s), heteroaryl optionally substituted with a substituent group C at one to three position(s), non-aromatic heterocyclic group optionally substituted with a substituent group C at one to three position(s), aryloxy optionally substituted with a substituent group C at one to three position(s), and alkylsulfonyl.

6. The compound of claim 4, wherein $R^1$ is unsubstituted C1, C2, or C3 alkylene.

7. The compound of claim 4, wherein $R^1$ is unsubstituted C1 alkylene.

8. The compound of claim 4, wherein $R^1$ is C1, C2, or C3 alkylene substituted with one or more alkyl groups.

9. The compound of claim 4, wherein $R^1$ is C1 alkylene substituted with one or two alkyl groups.

10. The compound of claim 4, wherein Q is substituted piperazine-1,4-diyl.

11. The compound of claim 4, wherein:
Q is:

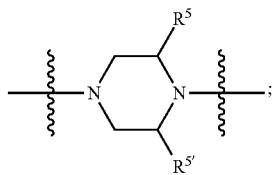

and
$R^5$ and $R^{5'}$ are independently alkyl optionally substituted at one to three position(s) with a substituent independently selected from a halogen atom and alkyloxy; oxo; cycloalkyl; alkenyl; alkynyl; hydroxy; alkyloxy optionally substituted at one to three position(s) with a substituent independently selected from a halogen atom and phenyl optionally substituted with one to three substituent(s) independently selected from a halogen atom, alkyl, alkyloxy, cyano, and nitro; aryloxy optionally substituted at one to three position(s) with a substituent independently selected from a halogen atom, alkyl, alkyloxy, cyano, and nitro; mercapto; alkylthio; a halogen atom; nitro; cyano; carboxy; alkyloxycarbonyl; acyl; alkylsulfonyl; optionally substituted amino; optionally substituted carbamoyl; aryl optionally substituted with one to three substituent(s) independently selected from a halogen atom, alkyl, alkyloxy, cyano, and nitro; heteroaryl optionally substituted at one to three position(s) with a substituent independently selected from a halogen atom and alkyl; and non-aromatic heterocyclic group optionally substituted at one to three position(s) with a substituent independently selected from a halogen atom and alkyl.

12. The compound of claim 11, wherein one or both of $R^5$ and $R^{5'}$ are independently oxo, hydroxy, or alkyloxy.

13. The compound of claim 11, wherein $R^5$ and $R^{5'}$ are each oxo.

14. The compound of claim 4, wherein one or both of $A^{19}$ and $A^{21}$ is N.

15. The compound of claim 4, wherein the $R^3$ on $A^{20}$ is a halogen atom, optionally substituted alkyl, optionally substituted alkenyl, optionally substituted alkynyl, optionally substituted cycloalkyl, optionally substituted cycloalkenyl, hydroxy, carboxy, optionally substituted alkyloxy, optionally substituted alkenyloxy, optionally substituted alkynyloxy, optionally substituted cycloalkyloxy, optionally substituted cycloalkenyloxy, mercapto, optionally substituted alkylthio, optionally substituted alkenylthio, optionally substituted alkynylthio, optionally substituted alkylsulfinyl, optionally substituted alkylsulfonyl, optionally substituted alkylsulfonyloxy, optionally substituted cycloalkylthio, optionally substituted cycloalkylsulfinyl, optionally substituted cycloalkylsulfonyl, optionally substituted cycloalkylsulfonyloxy, optionally substituted cycloalkenylthio, optionally substituted cycloalkenylsulfinyl, optionally substituted cycloalkenylsulfonyl, optionally substituted cycloalkenylsulfonyloxy, optionally substituted amino, acyl, optionally substituted alkyloxycarbonyl, optionally substituted alkenyloxycarbonyl, optionally substituted alkynyloxycarbonyl, optionally substituted aryloxycarbonyl, optionally substituted carbamoyl, optionally substituted sulfamoyl, cyano, nitro, optionally substituted aryl, optionally substituted aryloxy, optionally substituted arylthio, optionally substituted arylsulfinyl, optionally substituted arylsulfonyl, optionally substituted arylsulfonyloxy, optionally substituted heteroaryl, optionally substituted heteroaryloxy, optionally substituted heteroarylthio, optionally substituted heteroarylsulfinyl, optionally substituted heteroarylsulfonyl, optionally substituted heteroarylsulfonyloxy, or an optionally substituted non-aromatic heterocyclic group.

16. The compound of claim 4, wherein the $R^3$ on $A^{20}$ is cyano.

17. The compound of claim 1, wherein the compound is selected from:

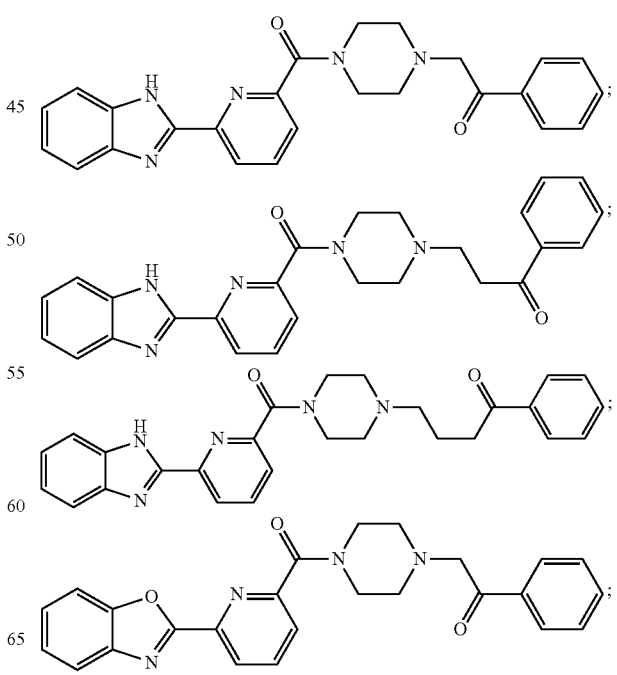

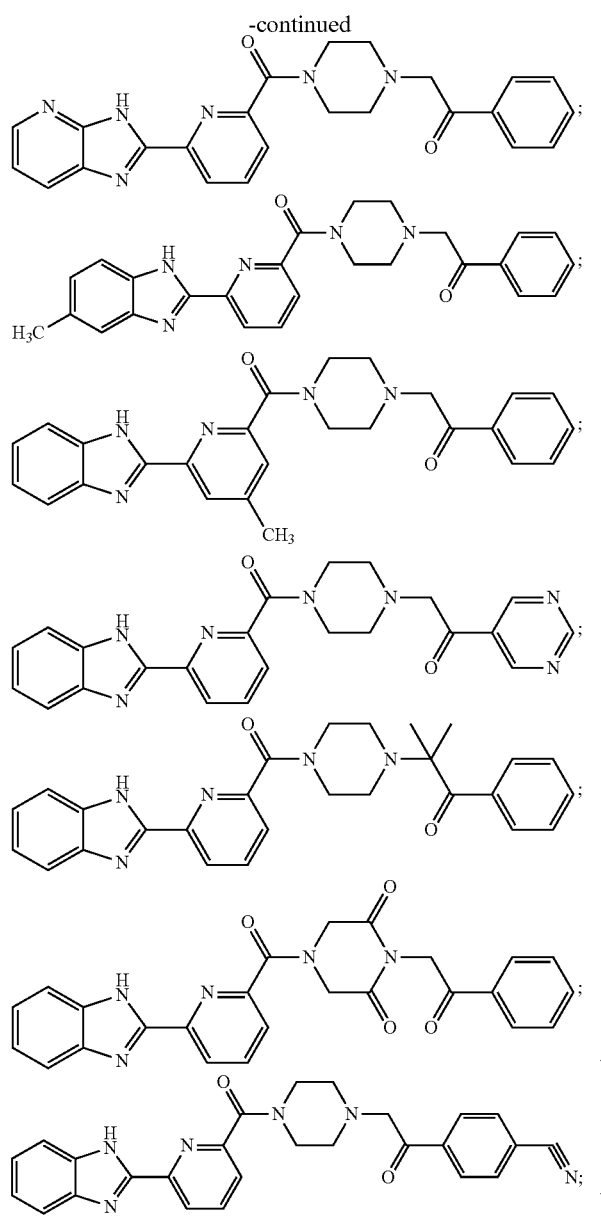

or a pharmaceutically acceptable salt of any of the foregoing.

18. A method of treating a condition in an animal with a compound as recited in claim 1, comprising administering an effective amount of the compound to the animal, wherein the condition comprises at least one of lupus, Sjögren's syndrome, rheumatoid arthritis, type 1 diabetes, psoriasis, inflammatory bowel disease, a viral disease, and nonalcoholic steatohepatitis.

19. The compound of claim 1, wherein $R^1$ is optionally substituted C1, C2, or C3 alkylene, which, when substituted, is substituted with one or more substituent(s) selected from the group consisting of alkyl optionally substituted with a substituent group D at one to three position(s), cycloalkyl, hydroxy, oxo, alkyloxy optionally substituted with a substituent group A at one to three position(s), mercapto, alkylthio, a halogen atom, nitro, cyano, carboxy, alkyloxycarbonyl, optionally substituted amino, optionally substituted carbamoyl, acyl, acyloxy, aryl optionally substituted with a substituent group B at one to three position(s), heteroaryl optionally substituted with a substituent group C at one to three position(s), non-aromatic heterocyclic group optionally substituted with a substituent group C at one to three position(s), aryloxy optionally substituted with a substituent group C at one to three position(s), and alkylsulfonyl.

20. The compound of claim 1, wherein $R^1$ is unsubstituted C1, C2, or C3 alkylene.

21. The compound of claim 1, wherein $R^1$ is unsubstituted C1 alkylene.

22. The compound of claim 1, wherein $R^1$ is C1, C2, or C3 alkylene substituted with one or more alkyl groups.

23. The compound of claim 1, wherein $R^1$ is C1 alkylene substituted with one or two alkyl groups.

24. The compound of claim 1, wherein Q is substituted piperazine-1,4-diyl.

25. The compound of claim 1, wherein:
Q is:

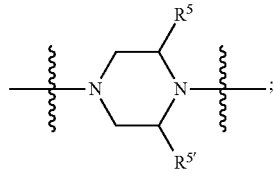

$R^5$ and $R^{5'}$ are independently alkyl optionally substituted at one to three position(s) with a substituent independently selected from a halogen atom and alkyloxy; oxo; cycloalkyl; alkenyl; alkynyl; hydroxy; alkyloxy optionally substituted at one to three position(s) with a substituent independently selected from a halogen atom and phenyl optionally substituted with one to three substituent(s) independently selected from a halogen atom, alkyl, alkyloxy, cyano, and nitro; aryloxy optionally substituted at one to three position(s) with a substituent independently selected from a halogen atom, alkyl, alkyloxy, cyano, and nitro; mercapto; alkylthio; a halogen atom; nitro; cyano; carboxy; alkyloxycarbonyl; acyl; alkylsulfonyl; optionally substituted amino; optionally substituted carbamoyl; aryl optionally substituted with one to three substituent(s) independently selected from a halogen atom, alkyl, alkyloxy, cyano, and nitro; heteroaryl optionally substituted at one to three position(s) with a substituent independently selected from a halogen atom and alkyl; and non-aromatic heterocyclic group optionally substituted at one to three position(s) with a substituent independently selected from a halogen atom and alkyl.

26. The compound of claim 25, wherein one or both of $R^5$ and $R^{5'}$ are independently oxo, hydroxy, or alkyloxy.

27. The compound of claim 25, wherein $R^5$ and $R^{5'}$ are each oxo.

28. The compound of claim 1, wherein one or both of $A^{19}$ and $A^{21}$ is N.

29. The compound of claim 1, wherein the $R^3$ on $A^{20}$ is a halogen atom, optionally substituted alkyl, optionally substituted alkenyl, optionally substituted alkynyl, optionally substituted cycloalkyl, optionally substituted cycloalkenyl, hydroxy, carboxy, optionally substituted alkyloxy, optionally substituted alkenyloxy, optionally substituted alkynyloxy, optionally substituted cycloalkyloxy, optionally substituted cycloalkenyloxy, mercapto, optionally substituted alkylthio, optionally substituted alkenylthio, optionally substituted alkynylthio, optionally substituted alkylsulfinyl, optionally substituted alkylsulfonyl, optionally substituted alkylsulfonyloxy, optionally substituted cycloalkylthio, optionally substituted cycloalkylsulfinyl, optionally substituted cycloalkylsulfonyl, optionally substituted cycloalkylsulfonyloxy, optionally substituted cycloalkenylthio, optionally substituted cycloalkenylsulfinyl, optionally substituted cycloalkenylsulfonyl, optionally substituted cycloalkenylsulfonyloxy, optionally substituted amino, acyl, optionally substituted alkyloxycarbonyl, optionally substituted alkenyloxycarbonyl, optionally substituted alkynyloxycarbonyl, optionally substituted aryloxycarbonyl, optionally substituted carbamoyl, optionally substituted sulfamoyl, cyano, nitro, optionally substituted aryl, optionally substituted aryloxy, optionally substituted arylthio, optionally substituted arylsulfinyl, optionally substituted arylsulfonyl, optionally substituted arylsulfonyloxy, optionally substituted heteroaryl, optionally substituted heteroaryloxy, optionally substituted heteroarylthio, optionally substituted heteroarylsulfinyl, optionally substituted heteroarylsulfonyl, optionally substituted heteroarylsulfonyloxy, or an optionally substituted non-aromatic heterocyclic group.

30. The compound of claim 1, wherein the $R^3$ on $A^{20}$ is cyano.

31. The compound of claim 1, wherein:
Q is piperazine-1,4-diyl or:

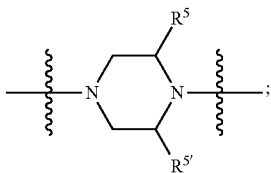

$R^5$ and $R^{5'}$ are each oxo;
$R^1$ is C1 alkylene optionally substituted with one or two alkyl groups; and
$R^3$ in each instance is independently a hydrogen atom, a halogen atom, unsubstituted alkyl, unsubstituted alkenyl, unsubstituted alkynyl, unsubstituted cycloalkyl, unsubstituted cycloalkenyl, hydroxy, carboxy, unsubstituted alkyloxy, unsubstituted alkenyloxy, unsubstituted alkynyloxy, unsubstituted cycloalkyloxy, unsubstituted cycloalkenyloxy, mercapto, unsubstituted alkylthio, unsubstituted alkenylthio, unsubstituted alkynylthio, unsubstituted alkylsulfinyl, unsubstituted alkylsulfonyl, unsubstituted alkylsulfonyloxy, unsubstituted cycloalkylthio, unsubstituted cycloalkylsulfinyl, unsubstituted cycloalkylsulfonyl, unsubstituted cycloalkylsulfonyloxy, unsubstituted cycloalkenylthio, unsubstituted cycloalkenylsulfinyl, unsubstituted cycloalkenylsulfonyl, unsubstituted cycloalkenylsulfonyloxy, unsubstituted amino, acyl, unsubstituted alkyloxycarbonyl, unsubstituted alkenyloxycarbonyl, unsubstituted alkynyloxycarbonyl, unsubstituted aryloxycarbonyl, unsubstituted carbamoyl, unsubstituted sulfamoyl, cyano, nitro, unsubstituted aryl, unsubstituted aryloxy, unsubstituted arylthio, unsubstituted arylsulfinyl, unsubstituted arylsulfonyl, unsubstituted arylsulfonyloxy, unsubstituted heteroaryl, unsubstituted heteroaryloxy, unsubstituted heteroarylthio, unsubstituted heteroarylsulfinyl, unsubstituted heteroarylsulfonyl, unsubstituted heteroarylsulfonyloxy, or an unsubstituted non-aromatic heterocyclic group.

32. The compound of claim 31, wherein each $R^3$ is hydrogen with the exception that the $R^3$ on $A^{20}$ is hydrogen or cyano.

33. The compound of claim 31, wherein:
$A^4$ is $C(R^3)$;
$A^5$ is $N(R^3)$; and
$A^6$ and $A^{10}$ are each N.

34. The compound of claim 33, wherein each $R^3$ is hydrogen with the exception that the $R^3$ on $A^{20}$ is hydrogen or cyano.

35. The compound of claim 1, wherein the compound is:

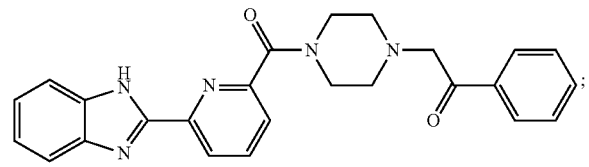

or a pharmaceutically acceptable salt thereof.

36. The compound of claim 1, wherein the compound is:

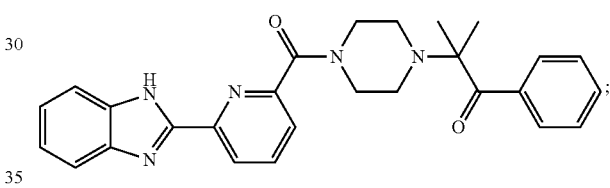

or a pharmaceutically acceptable salt thereof.

37. The compound of claim 1, wherein the compound is:

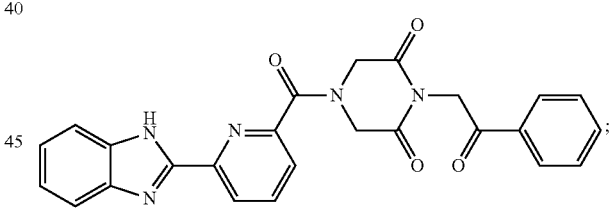

or a pharmaceutically acceptable salt thereof.

38. The compound of claim 1, wherein the compound is:

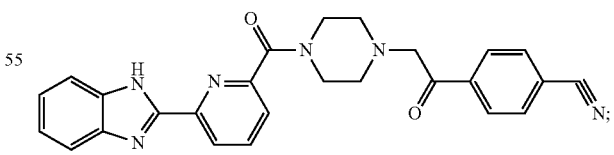

or a pharmaceutically acceptable salt thereof.

* * * * *

UNITED STATES PATENT AND TRADEMARK OFFICE
CERTIFICATE OF CORRECTION

Page 1 of 1

PATENT NO. : 11,117,881 B2
APPLICATION NO. : 17/127119
DATED : September 14, 2021
INVENTOR(S) : Bassaganya-Riera et al.

It is certified that error appears in the above-identified patent and that said Letters Patent is hereby corrected as shown below:

In the Claims

Claim 3 Column 52, Line 30, delete "R" and insert --$R^1$--.

Signed and Sealed this
Nineteenth Day of October, 2021

Drew Hirshfeld
*Performing the Functions and Duties of the*
*Under Secretary of Commerce for Intellectual Property and*
*Director of the United States Patent and Trademark Office*